(12) United States Patent
Watanabe et al.

(10) Patent No.: US 12,227,517 B2
(45) Date of Patent: Feb. 18, 2025

(54) PYRIDAZINYL-THIAZOLECARBOXAMIDE COMPOUND

(71) Applicants: Astellas Pharma Inc., Tokyo (JP); Kotobuki Pharmaceutical Co., Ltd., Nagano (JP)

(72) Inventors: Hideyuki Watanabe, Tokyo (JP); Yohei Seki, Tokyo (JP); Keiichiro Okuyama, Tokyo (JP); Kazuo Kurosawa, Tokyo (JP); Osamu Ikeda, Tokyo (JP); Hiroshi Tomiyama, Nagano (JP); Yoshinori Iwai, Nagano (JP); Akihiko Nakamura, Nagano (JP); Kozo Miyasaka, Nagano (JP)

(73) Assignees: Astellas Pharma Inc., Tokyo (JP); KOTOBUKI PHARMACEUTICAL CO., LTD., Nagano (JP)

( * ) Notice: Subject to any disclaimer, the term of this patent is extended or adjusted under 35 U.S.C. 154(b) by 741 days.

(21) Appl. No.: 17/427,426

(22) PCT Filed: Dec. 24, 2020

(86) PCT No.: PCT/JP2020/048337
§ 371 (c)(1),
(2) Date: Jul. 30, 2021

(87) PCT Pub. No.: WO2021/132422
PCT Pub. Date: Jul. 1, 2021

(65) Prior Publication Data
US 2022/0315603 A1    Oct. 6, 2022

(30) Foreign Application Priority Data
Dec. 25, 2019    (JP) ................. 2019-233673

(51) Int. Cl.
| | | |
|---|---|---|
| C07D 498/10 | (2006.01) | |
| A61P 35/00 | (2006.01) | |
| C07D 417/14 | (2006.01) | |
| C07D 471/10 | (2006.01) | |
| C07D 487/04 | (2006.01) | |

(52) U.S. Cl.
CPC ............ *C07D 498/10* (2013.01); *A61P 35/00* (2018.01); *C07D 417/14* (2013.01); *C07D 471/10* (2013.01); *C07D 487/04* (2013.01)

(58) Field of Classification Search
CPC ........ A61P 35/00; A61P 43/00; C07D 417/14; C07D 471/10; C07D 487/04; C07D 498/10; A61K 31/501; A61K 31/5377
See application file for complete search history.

(56) References Cited

U.S. PATENT DOCUMENTS

| | | |
|---|---|---|
| 7,381,401 B2 | 6/2008 | Gajewski |
| 12,077,519 B2 | 9/2024 | Watanabe et al. |
| 2005/0266510 A1 | 12/2005 | Gajewski |
| 2009/0286766 A1 | 11/2009 | Sugasawa et al. |
| 2024/0043403 A1 | 2/2024 | Watanabe |

FOREIGN PATENT DOCUMENTS

| | | | |
|---|---|---|---|
| EP | 4253373 A1 | 10/2023 | |
| JP | 2008-528520 A | 7/2008 | |
| JP | 2009-524677 A | 7/2009 | |
| JP | 2014-221840 A | 11/2014 | |
| JP | 2020-532561 A | 11/2020 | |
| WO | 2006/081391 A2 | 8/2006 | |
| WO | 2007/087427 A2 | 8/2007 | |
| WO | WO-2007123269 A1 * | 11/2007 | ........... C07D 263/34 |
| WO | WO-2008054702 A1 * | 5/2008 | ........... C07D 277/56 |
| WO | 2019/046944 A1 | 3/2019 | |
| WO | 2020/006018 A1 | 1/2020 | |
| WO | 2021/132422 A1 | 7/2021 | |
| WO | 2021/214019 A1 | 10/2021 | |
| WO | 2021/214020 A1 | 10/2021 | |

OTHER PUBLICATIONS

Bardhan et al., The PD1:PD-L1/2 Pathway from Discovery to Clinical Implementation. Front Immunol. Dec. 12, 2016;7:550, 7 pages.
Gharbi et al., Transient PKCalpha shuttling to the immunological synapse is governed by DGKzeta and regulates L-selectin shedding. J Cell Sci. May 15, 2013;126(Pt 10):2176-86.
Jing et al., T Cells Deficient in Diacylglycerol Kinase zeta Are Resistant to PD-1 Inhibition and Help Create Persistent Host Immunity to Leukemia. Cancer Res. Oct. 15, 2017;77(20):5676-5686.
Joshi et al., Diacylglycerol kinases: regulated controllers of T cell activation, function, and development. Int J Mol Sci. Mar. 26, 2013;14(4):6649-73.
Krishna et al., Role of diacylglycerol kinases in T cell development and function. Crit Rev Immunol. 2013;33(2):97-118.

(Continued)

*Primary Examiner* — Jean P Cornet
(74) *Attorney, Agent, or Firm* — McCarter & English, LLP; Wei Song; James M. Alburger

(57) ABSTRACT

A compound useful as an active ingredient of a pharmaceutical composition for treatment of cancer related to activation of immune cells or cancer having resistance to anti-PD-1 antibody/anti-PD-L1 antibody therapy is provided.

The present inventors have conducted studies on a compound useful as an active ingredient of a pharmaceutical composition for treatment of cancer related to activation of immune cells or cancer having resistance to anti-PD-1 antibody/anti-PD-L1 antibody therapy, and found that a pyridazinyl-thiazolecarboxamide compound has DGK ξ (DGKzeta) inhibitory effect, leading to completion of the present invention. The pyridazinyl-thiazolecarboxamide compound of the present invention has DGK ξ inhibitory effect, and can be used as a therapeutic agent for treatment of cancer related to activation of immune cells or cancer having resistance to anti-PD-1 antibody/anti-PD-L1 antibody therapy.

24 Claims, No Drawings

(56) References Cited

OTHER PUBLICATIONS

O'Donnell et al., Resistance to PD1/PDL1 checkpoint inhibition. Cancer Treat Rev. Jan. 2017;52:71-81.
Riese et al., Diacylglycerol Kinases (DGKs): Novel Targets for Improving T Cell Activity in Cancer. Front Cell Dev Biol. Oct. 17, 2016;4:108, 7 pages.
Yang et al., Diacylglycerol Kinase ? Is a Target To Enhance NK Cell Function. J Immunol. Aug. 1, 2016;197(3):934-41.
Zhong et al., Diacylglycerol kinases in immune cell function and self-tolerance. Immunol Rev. Aug. 2008;224:249-64.
International Search Report and Written Opinion for Application No. PCT/JP2020/048337, dated Feb. 22, 2021, 14 pages.
International Preliminary Report on Patentability for Application No. PCT/JP2020/048337, dated Jul. 7, 2022, 6 pages.
International Search Report and Written Opinion for Application No. PCT/JP2021/043540, dated Jan. 11, 2022, 12 pages.
1 European Office Action for Application No. 20906466.6, dated Nov. 22, 2023, 5 pages.
Ruger et al., Synthesis of tetra-substituted pyrazoles. Tetrahedron. 2012;68:8823-8829.
Velnati et al., Identification of a novel DGKalpha inhibitor for XLP-1 therapy by virtual screening. Eur J Med Chem. Feb. 15, 2019;164:378-390.
European Office Action for Application No. 21898136.3, dated Oct. 16, 2024, 8 pages.
U.S. Appl. No. 18/254,829, filed May 26, 2023.
U.S. Appl. No. 18/521,400, filed Nov. 28, 2023.

\* cited by examiner

PYRIDAZINYL-THIAZOLECARBOXAMIDE COMPOUND

CROSS-REFERENCE TO RELATED APPLICATIONS

This application is a U.S. national stage filing, under 35 U.S.C. § 371 (c), of International Application No. PCT/JP2020/048337, filed on Dec. 24, 2020, which claims priority to Japanese Patent Application No. 2019-233673, filed on Dec. 25, 2019.

TECHNICAL FIELD

The present invention relates to a pyridazinyl-thiazolecarboxamide compound which is useful as a pharmaceutical composition, for example, a diacylglycerol kinase ξ (DGKzeta) inhibitor, and is expected to be useful as an active ingredient of, for example, a pharmaceutical composition for treatment of cancer related to activation of immune cells or cancer having resistance to anti-PD-1 antibody/anti-PD-L1 antibody therapy, particularly a pharmaceutical composition for treatment of cancer related to activation of immune cells, which has resistance to anti-PD-1 antibody/anti-PD-L1 antibody therapy.

BACKGROUND ART

Cancer immunotherapy has drawn attention as the fourth mainstay cancer treatment method following conventional surgical treatment, radiation therapy and cancer drug therapy (chemotherapy and molecular targeted drugs). It is an anti-cytotoxic T-lymphocyte antigen (CTLA)-4 antibody (ipilimumab) and an anti-PD-1 antibody (nivolumab or pembrolizumab) that have paved the way for the cancer immunotherapy. CTLA-4 and PD-1 are called immune checkpoint molecules, and function as "inhibitory checkpoint molecules". Currently, the anti-PD-1 antibody is proven to be effective in clinical practice against many cancers including melanoma and non-small cell lung cancer, and application of the anti-PD-1 antibody is expanding. In recent years, development of antibodies targeting checkpoint molecules other than CTLA-4 and PD-1 has become active throughout the world.

DGK is an enzyme which converts diacylglycerol (DAG) into phosphatidic acid (PA) by phosphorylation. In mammals, DGK has ten isoforms, which are classified broadly into five types according to structural characteristics. These five types of isoforms are type I (α, β, γ), type II (δ, η, κ), type III (e), type IV (ξ, ι) and type V (θ). All the isoforms have a catalytic domain, which is highly homologous among them, in the C-terminal portion, and a C1 domain, which has a homology with protein kinase C (PKC), in the molecule. The C1 domain is considered to be a domain to which phorbol ester/DAG binds (Int. J. Mol. Sci. 2013, 14: 6649-6673).

In T cells, phospholipase Cγ1 (PLCγ1) activated by antigenic stimulation produces DAG and inositol triphosphate (IP3) from phosphatidylinositol 4,5-bisphosphate (PIP2). The produced DAG activates a plurality of downstream signals including RAS, NF-κB and AKT pathways, leading to activation of T cells. On the other hand, IP3 activates nuclear factor of activated T cells (NFAT) signals via discharge of $Ca^{2+}$ from the endoplasmic reticulum, and is involved in not only activation of T cells but also induction of anergy. The anergy of T cells is an incomplete activated state caused by depression of costimulatory (CD28 signal) or inhibition of costimulatory during antigen recognition, and in this state, no response is produced even by restimulation.

DGK α and DGK ξ are two main isoforms in T cells, and each of these isoforms adjusts the intensity of the DAG signal down stream of antigenic stimulation to prevent excessive activation of T cells. Further, DGK α and DGK ξ promote anergy of T cells, and play an important role in immune tolerance of T cells (J Cell Sci. 2013, 126:2176-2186, Crit Rev Immunol. 2013, 33: 97-118, Immunol rev. 2008, 224: 249-264).

Further, activation of T cells lacking DGK ξ has been reported to produce resistance to inhibitory signals from PD-1, and resistance to a transforming growth factor (TGF)-β and PD-1 independent immunosuppressive factors such as Adenosine and PGE2 (Cancer Res. 2017, 77: 5676-5686, Front Cell Dev Biol. 2016, 4: 108). It has been reported that T cells having overexpressed PD-1 molecules are extremely exhausted, and that in this state, the anti-PD-1 antibody has no effect. Immunosuppressive factors such as TGF-β are considered to be one of resistance mechanisms of anti-PD-1 therapy (Cancer treatment Reviews 2017, 52: 71-81). It has been reported that in NK cells, DGK ξ negatively controls activation of NK cells by activated receptor stimulation, and that in DGK ξ KO mice, growth of a major histocompatibility complex (MHC) class I-deficient tumor is suppressed (J Immunol. 2016, 197: 934-941).

Therefore, a DGK ξ inhibitor to be produced is expected to have antitumor effect through activation of immune cells, particularly activation of T cells. Further, it has been reported that the response rate of anti-PD-1 antibody therapy varies depending on a type of cancer, but is approximately 30% in general, (Front Immunol. 2016, 7: 550), and the DGK ξ inhibitor is also expected to be useful for patients with resistance to anti-PD-1 antibody therapy.

Patent Document 1 discloses that R59022 and R59499 have DGK inhibitory effect, alleviate anergy of T cells, and upregulate the immune response.

[Chemical Formula 1]

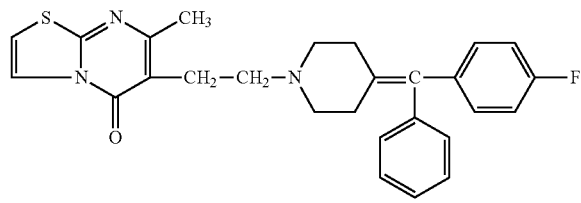

(R59022)

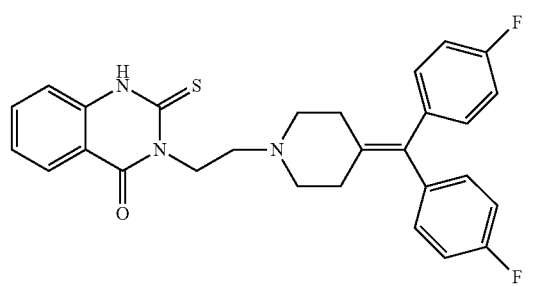

(R59499)

Patent Document 2 discloses that the compound of the following formula has trkA receptor inhibitory effect, and is useful for treatment or prevention of frequent urination and urge to urinate associated with the hyperactive bladder, etc.

[Chemical Formula 2]

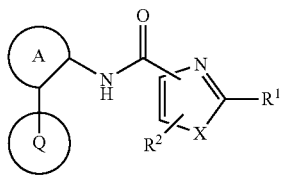

(A)

(See the publication for the meanings of the symbols in the formula)

In Patent Document 2, however, there is no specific disclosure of the use in a treatment of cancer and the compound of the present invention comprising a phenyl group having a sequence of four adjacent substituents as an indispensable constituent feature.

Patent Document 3 discloses that the compound of the following formula is useful for treatment or prevention of proliferative disorders, etc. as a protein kinase inhibitor against a cyclin dependent kinase (CDK) etc. Patent Document 3 also discloses the compound of Example 199 (hereinafter, referred to as Compound C).

[Chemical Formula 3-1]

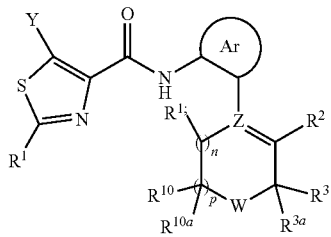

(B)

[Chemical Formula 3-2]

Example 199

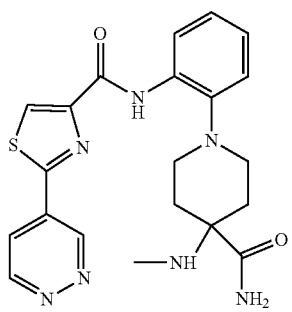

(See the publication for the meanings of the symbols in the formula)

In Patent Document 3, however, there is no specific disclosure of DGK and the compound of the present invention comprising a phenyl group having a sequence of four adjacent substituents as an indispensable constituent feature.

RELATED ART DOCUMENT

Patent Document

Patent Document 1: U.S. Pat. No. 7,381,401
Patent Document 2: International Publication No. WO 02007/123269

Patent Document 3: International Publication No. WO 02008/054702

SUMMARY OF INVENTION

Technical Problem

A compound which is useful as a pharmaceutical composition, for example, a DGK ξ inhibitor, and is expected to be useful as an active ingredient of a pharmaceutical composition for treatment of cancer related to activation of immune cells or cancer having resistance to anti-PD-1 antibody/anti-PD-L1 antibody therapy, particularly a pharmaceutical composition for treatment of cancer related to activation of immune cells, which has resistance to anti-PD-1 antibody/anti-PD-L1 antibody therapy is provide.

Solution to Problem

The present inventors have extensively conducted studies on a compound useful as an active ingredient of a pharmaceutical composition for treatment of cancer related to activation of immune cells or cancer having resistance to anti-PD-1 antibody/anti-PD-L1 antibody therapy, particularly a pharmaceutical composition for treatment of cancer related to activation of immune cells, which has resistance to anti-PD-1 antibody/anti-PD-L1 antibody therapy. As a result, the present inventors have found that a pyridazinyl-thiazolecarboxamide compound of formula (1) has excellent DGK ξ inhibitory effect, leading to completion of the present invention. The pyridazinyl-thiazolecarboxamide compound of formula (1) comprises a phenyl group having a sequence of four adjacent substituents, which is generally considered difficult of be synthesized, as an indispensable constituent feature.

That is, the present invention relates to a compound of formula (I) or a salt thereof, and a pharmaceutical composition containing a compound of formula (I) or a salt thereof, and one or more pharmaceutically acceptable excipients:

[Chemical Formula 4]

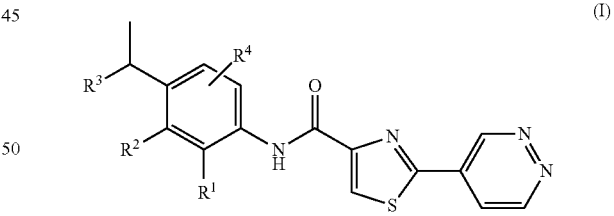

(I)

wherein
$R^1$ is a group of formula (i), (ii), (iii) (iv) or (v):

[Chemical Formula 5]

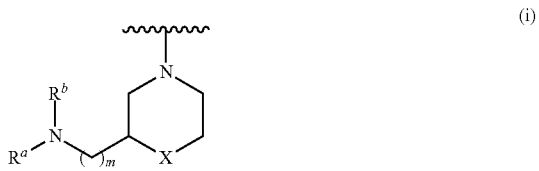

(i)

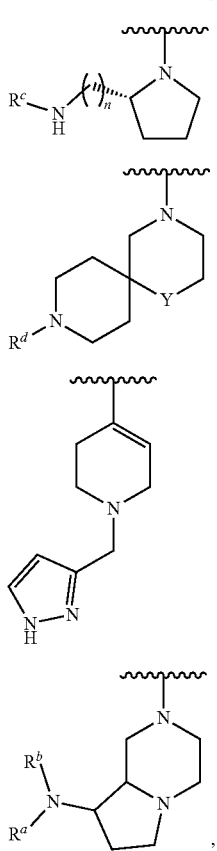

$R^2$ is a $C_{1-6}$ alkyl, a $C_{3-5}$ cycloalkyl, an —O—($C_{1-6}$ alkyl), methanesulphonyl, a halogeno-$C_{1-6}$ alkyl or a halogen, $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulphonyl and a halogen, ii) a $C_{3-8}$ cycloalkyl optionally substituted with a group selected from the group consisting of a $C_{1-6}$ alkyl and a halogen, iii) a pyridyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulphonyl and a halogen, iv) a pyrazolyl optionally substituted with a group selected from the group consisting of a $C_{1-6}$ alkyl and a halogen, or v) a pyrrolidinyl optionally substituted with a $C_{1-6}$ alkyl, $R^4$ is H or F, L is a bond, CO, $SO_2$, O or NH, X is $CH_2$, O or N-methyl, Y is $CH_2$ or O, $R^a$ is H or methyl, $R^b$ is H, methyl, ethyl or —$(CH_2)_2$O—$CH_3$, $R^c$ is H, methyl or oxetanyl, $R^d$ is H, methyl, —$(CH_2)_2$OH, —$(CH_2)_2$O—$CH_3$ or oxetanyl, m is 1 or 2, and n is 1 or 2.

When symbols in a chemical formula are used in other chemical formulae in the present description, the same symbols have the same meanings unless otherwise specified.

In addition, the present invention relates to a pharmaceutical composition for treatment of cancer related to activation of immune cells or cancer having resistance to anti-PD-1 antibody/anti-PD-L1 antibody therapy, containing a compound of formula (I) or a salt thereof, particularly a pharmaceutical composition for treatment of cancer related to activation of immune cells, which has resistance to anti-PD-1 antibody/anti-PD-L1 antibody therapy. Note that, the pharmaceutical composition includes a therapeutic agent for treatment of cancer related to activation of immune cells or cancer having resistance to anti-PD-1 antibody/anti-PD-L1 antibody therapy, containing a compound of formula (I) or a salt thereof, particularly a therapeutic agent for treatment of cancer related to activation of immune cells, which has resistance to anti-PD-1 antibody/anti-PD-L1 antibody therapy.

In addition, the present invention relates to a compound of formula (I) or a salt thereof which is a DGK ξ inhibitor; a compound of formula (I) or a salt thereof which is used as a DGK ξ inhibitor; a DGK ξ inhibitor comprising a compound of formula (I) or a salt thereof; use of a compound of formula (I) or a salt thereof for the manufacture of a pharmaceutical composition for treatment of cancer related to activation of immune cells or cancer having resistance to anti-PD-1 antibody/anti-PD-L1 antibody therapy, particularly for treatment of cancer related to activation of immune cells, which has resistance to anti-PD-1 antibody/anti-PD-L1 antibody therapy; use of a compound of formula (I) or a salt thereof for treatment of cancer related to activation of immune cells or cancer having resistance to anti-PD-1 antibody/anti-PD-L1 antibody therapy, particularly for treatment of cancer related to activation of immune cells, which has resistance to anti-PD-1 antibody/anti-PD-L1 antibody therapy; a compound of formula (I) or a salt thereof which is used for treatment of cancer related to activation of immune cells or cancer having resistance to anti-PD-1 antibody/anti-PD-L1 antibody therapy, particularly for treatment of cancer related to activation of immune cells, which has resistance to anti-PD-1 antibody/anti-PD-L1 antibody therapy; and a method for treatment of cancer related to activation of immune cells or cancer having resistance to anti-PD-1 antibody/anti-PD-L1 antibody therapy, comprising administering an effective amount of a compound of formula (I) or a salt thereof to a subject, particularly a method for treatment of cancer related to activation of immune cells, which has resistance to anti-PD-1 antibody/anti-PD-L1 antibody therapy. The "subject" is a human or another animal in need of prevention or treatment of the cancer. In an embodiment, the "subject" is a human in need of prevention or treatment of the cancer.

Advantageous Effects of Invention

A compound of formula (I) or a salt thereof has a DGK ξ inhibitory effect, and can be used as a therapeutic agent for treatment of cancer related to activation of immune cells or cancer having resistance to anti-PD-1 antibody/anti-PD-L1 antibody therapy, particularly a therapeutic agent for treatment of cancer related to activation of immune cells, which has resistance to anti-PD-1 antibody/anti-PD-L1 antibody therapy.

DESCRIPTION OF EMBODIMENTS

Hereinafter, the present invention will be described in detail.

In the present description, the following terms have the following meanings unless otherwise specified. The following definitions are intended to clarify the defined terms rather than limiting the terms. If a term used herein is not specifically defined, such a term is used with a meaning which is commonly accepted by those skilled in the art.

In the present description, the "$C_{1-6}$ alkyl" is a linear or branched alkyl having 1 to 6 carbon atoms (hereinafter, abbreviated as $C_{1-6}$). Examples thereof include methyl, ethyl, n-propyl, isopropyl, n-butyl, isobutyl, sec-butyl, tert-butyl, n-pentyl and n-hexyl. In an embodiment, the "$C_{1-6}$ alkyl" is a $C_{1-3}$ alkyl. In an embodiment, the "$C_{1-6}$ alkyl" is methyl or ethyl. In an embodiment, the "$C_{1-6}$ alkyl" is methyl. In an embodiment, the "$C_{1-6}$ alkyl" is ethyl.

The "halogeno-$C_{1-6}$ alkyl" is a $C_{1-6}$ alkyl substituted with one or more halogens. In an embodiment, the "halogeno-$C_{1-6}$ alkyl" is a $C_{1-6}$ alkyl substituted with one to five halogens. In an embodiment, the "halogeno-$C_{1-6}$ alkyl" is a halogeno-$C_{1-3}$ alkyl substituted with one to five halogens. In an embodiment, the "halogeno-$C_{1-6}$ alkyl" is difluoromethyl or trifluoromethyl. In an embodiment, the "halogeno-$C_{1-6}$ alkyl" is trifluoromethyl.

The "$C_{3-8}$ cycloalkyl" is a saturated hydrocarbon ring group of $C_{3-8}$, and may be crosslinked, or may form a spiro-ring. Examples thereof include cyclopropyl, cyclobutyl, cyclopentyl, cyclohexyl, cycloheptyl, cyclooctyl, bicyclo[2,2,1]heptyl, bicyclo[3,10]hexyl, bicyclo[3,1,1]heptyl and spiro[2,5]octyl. In an embodiment, the "$C_{3-8}$ cycloalkyl" is a "$C_{3-5}$ cycloalkyl". In an embodiment, the "$C_{3-5}$ cycloalkyl" is cyclopropyl, cyclobutyl or cyclopentyl. In an embodiment, the "$C_{3-5}$ cycloalkyl" is cyclopropyl. In an embodiment, the "$C_{3-5}$ cycloalkyl" is cyclobutyl. In an embodiment, the "$C_{3-5}$ cycloalkyl" is cyclopentyl.

The "halogen" is F, Cl, Br or I. In an embodiment, the "halogen" is F or Cl. In an embodiment, the "halogen" is Cl.

The term "optionally substituted" means being unsubstituted, or being "substituted with one or more substituents (e.g. substituents as defined below)". The substituent may occur at any position as long as hydrogen is normally present at the position. In an embodiment, the term "optionally substituted" means being "optionally substituted with one to five substituents". In another embodiment, the term "optionally substituted" means being "optionally substituted with one to three substituents". When there are a plurality of substituents, these substituents may be the same or different.

One or more embodiments can be combined with another embodiment even though a specific combination is not described. That is, all embodiments can be freely combined.

The "activation of immune cells" means that immune cells having the capability of suppressing growth of cancer cells or shrinking or eliminating cancer cells (hereinafter, referred to as antitumor activity), particularly T cells are reactivated, and/or that the number of immune cells, particularly activated T cells is increased. In an embodiment, the term "activation of immune cells" means activation of immune cells based on DGK ξ inhibitory effect.

The "cancer related to activation of immune cells" is a cancer having immune responsiveness. In an embodiment, the "cancer related to activation of immune cells" is a cancer in which growth of cancer cells is suppressed or cancer cells are shrunk or eliminated by activation of immune cells. In an embodiment, the "cancer related to activation of immune cells" is a cancer in which growth of cancer cells is suppressed by activation of immune cells. In an embodiment, the "cancer related to activation of immune cells" is a cancer in which growth of cancer cells are shrunk or eliminated by activation of immune cells. In an embodiment, the "cancer related to activation of immune cells" is a cancer in which growth of cancer cells is suppressed or cancer cells are shrunk or eliminated by activation of immune cells based on DGK ξ inhibitory effect. In an embodiment, the "cancer related to activation of immune cells" is a cancer in which growth of cancer cells is suppressed by activation of immune cells based on DGK ξ inhibitory effect. In an embodiment, the "cancer related to activation of immune cells" is a cancer in which growth of cancer cells are shrunk or eliminated by activation of immune cells based on DGK ξ inhibitory effect.

Examples of cancers to which the subject invention can be applied include, but are not limited to small cell lung cancer, head and neck cancer, kidney cancer, ovary cancer, non-small cell lung cancer, mismatch repair-deficient bowel cancer, urothelial cancer, melanoma, hepatocyte cancer, stomach cancer and bladder cancer.

The term "resistant to anti-PD-1 antibody/anti-PD-L1 antibody therapy" means "resistant to an anti-PD-1 antibody therapy and/or an anti-PD-L1 antibody therapy". In an embodiment, the term "resistant to anti-PD-1 antibody/anti-PD-L1 antibody therapy" means "resistant to an anti-PD-1 antibody therapy and an anti-PD-L1 antibody therapy". In an embodiment, the term "resistant to anti-PD-1 antibody/anti-PD-L1 antibody therapy" means "resistant to an anti-PD-1 antibody therapy". In an embodiment, the term "resistant to anti-PD-1 antibody/anti-PD-L1 antibody therapy" means "resistant to an anti-PD-L1 antibody therapy". In particular, the term "resistant to anti-PD-1 antibody/anti-PD-L1 antibody therapy" means that immunotherapy with an anti-PD-1 antibody and/or an anti-PD-L1 antibody becomes ineffective soon after the start of treatment (primary resistance), or acquires resistance to treatment from the middle of the treatment (acquired resistance), so that cancer cells grow again.

The "cancer resistant to anti-PD-1 antibody/anti-PD-L1 antibody therapy" means a cancer resistant to an anti-PD-1 antibody therapy and/or an anti-PD-L1 antibody therapy. In an embodiment, the "cancer resistant to anti-PD-1 antibody/anti-PD-L1 antibody therapy" means a cancer resistant to an anti-PD-1 antibody therapy and an anti-PD-L1 antibody therapy. In an embodiment, the "cancer resistant to anti-PD-1 antibody/anti-PD-L1 antibody therapy" means a cancer resistant to an anti-PD-1 antibody therapy. In an embodiment, the "cancer resistant to anti-PD-1 antibody/anti-PD-L1 antibody therapy" means a cancer resistant to an anti-PD-L1 antibody therapy. In particular, the "cancer resistant to anti-PD-1 antibody/anti-PD-L1 antibody therapy" means a cancer in which immunotherapy with an anti-PD-1 antibody and/or an anti-PD-L1 antibody becomes ineffective soon after the start of treatment (primary resistance), or acquires resistance to treatment from the middle of the treatment (acquired resistance), so that cancer cells grow again.

Examples of cancers to which the subject invention can be applied include cancers resistant to anti-PD-1 antibody/anti-PD-L1 antibody therapy, which include, but are not limited to, small cell lung cancer, head and neck cancer, kidney cancer, ovary cancer, non-small cell lung cancer, mismatch repair-deficient bowel cancer, urothelial cancer, melanoma, hepatocyte cancer, stomach cancer and bladder cancer.

Examples of "anti-PD-1 antibody/anti-PD-L1 antibody" include, but are not limited to, an antibody selected from Nivolumab, Pembrolizumab, Atezolizumab, Pidilizumab, Avelumab and Durvalumab.

An embodiment of the compound of formula (I) or a salt thereof of the present invention will be shown below:

(1-1) A compound or a salt thereof in which $R^1$ is a group of the following formula (i), (ii), (iii) (iv) or (v):

[Chemical Formula 6]

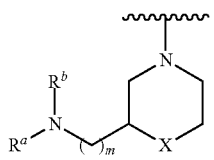
(i)

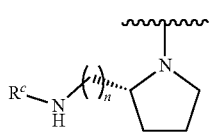
(ii)

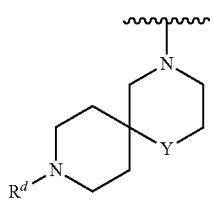
(iii)

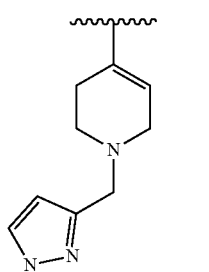
(iv)

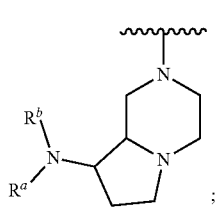
(v)

(1-2) A compound or a salt thereof in which $R^1$ is a group of the following formula (i-a), (ii-a), (iii-a) or (v):

[Chemical Formula 7]

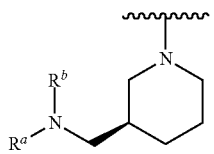
(i-a)

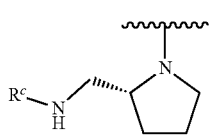
(ii-a)

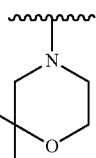
(iii-a)

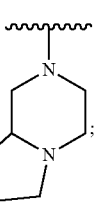
(v)

(1-3) A compound or a salt thereof in which $R^1$ is a group of the following formula (i), (ii), (iii) or (iv):

[Chemical Formula 8]

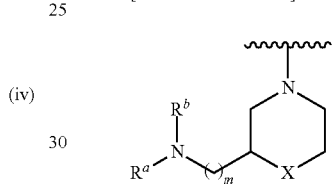
(i)

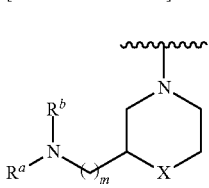
(ii)

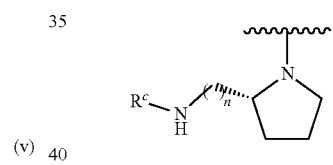
(iii)

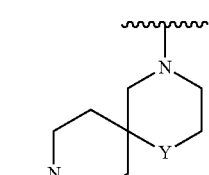
(iv)

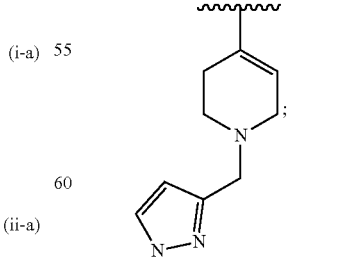

(1-4) A compound or a salt thereof in which $R^1$ is a group of the following formula (i-a), (ii-a) or (iii-a):

[Chemical Formula 9]

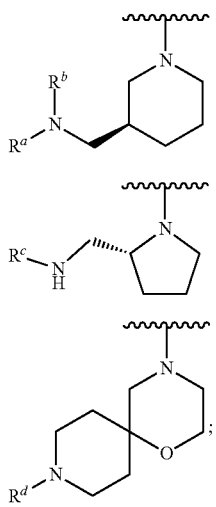

(2) A compound or a salt thereof in which $R^2$ is a $C_{1-6}$ alkyl, a $C_{3-5}$ cycloalkyl, an —O—($C_{1-6}$ alkyl), methanesulphonyl, a halogeno-$C_{1-6}$ alkyl or a halogen; in an embodiment, a compound or a salt thereof in which $R^2$ is a halogeno-$C_{1-6}$ alkyl or a halogen; in an embodiment, a compound or a salt thereof in which $R^2$ is a halogeno-$C_{1-3}$ alkyl, F, Cl or Br; in an embodiment, a compound or a salt thereof in which $R^2$ is $CF_3$, F or Cl; in an embodiment, a compound or a salt thereof in which $R^2$ is $CF_3$; in an embodiment, a compound or a salt thereof in which $R^2$ is F; or in an embodiment, a compound or a salt thereof in which $R^2$ is Cl;

(3-1) A compound or a salt thereof in which $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulphonyl and a halogen, ii) a $C_{3-8}$ cycloalkyl optionally substituted with a group selected from the group consisting of a $C_{1-6}$ alkyl and a halogen, iii) a pyridyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulphonyl and a halogen, iv) a pyrazolyl optionally substituted with a group selected from the group consisting of a $C_{1-6}$ alkyl and a halogen, or v) a pyrrolidinyl optionally substituted with a $C_{1-6}$ alkyl;

(3-2) A compound or a salt thereof in which $R^3$ is i) a phenyl optionally substituted with a group selected from the group consisting of a $C_{1-6}$ alkyl, cyano, nitro and a halogen, ii) a $C_{3-8}$ cycloalkyl, iii) a pyridyl, iv) a pyrazolyl optionally substituted with a $C_{1-6}$ alkyl, or v) a pyrrolidinyl;

(3-3) A compound or a salt thereof in which $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulphonyl and a halogen, or ii) a $C_{3-8}$ cycloalkyl optionally substituted with a group selected from the group consisting of a $C_{1-6}$ alkyl and a halogen;

(3-4) A compound or a salt thereof in which $R^3$ is a phenyl optionally substituted with a group selected from the group consisting of a $C_{1-6}$ alkyl and a halogen, or a $C_{3-5}$ cycloalkyl;

(4) A compound or a salt thereof in which $R^4$ is H or F; in an embodiment, a compound or a salt thereof in which $R^4$ is H; or in an embodiment, a compound or a salt thereof in which $R^4$ is F;

(5) A compound or a salt thereof in which L is a bond, CO, $SO_2$, O or NH; in an embodiment, a compound or a salt thereof in which L is a bond, O or NH; in an embodiment, a compound or a salt thereof in which L is O or NH; in an embodiment, a compound or a salt thereof in which L is O; or in an embodiment, a compound or a salt thereof in which L is NH;

(6) A compound or a salt thereof in which X is $CH_2$, O or N-methyl; in an embodiment, a compound or a salt thereof in which X is $CH_2$ or N-methyl; in an embodiment, a compound or a salt thereof in which X is $CH_2$; or in an embodiment, a compound or a salt thereof in which X is N-methyl;

(7) A compound or a salt thereof in which Y is $CH_2$ or O; in an embodiment, a compound or a salt thereof in which Y is $CH_2$; or in an embodiment, a compound or a salt thereof in which Y is O;

(8) A compound or a salt thereof in which $R^a$ is H or methyl; in an embodiment, a compound or a salt thereof in which $R^a$ is H; or in an embodiment, a compound or a salt thereof in which $R^a$ is methyl;

(9) A compound or a salt thereof in which $R^b$ is H, methyl, ethyl or —($CH_2)_2$O—$CH_3$; in an embodiment, a compound or a salt thereof in which $R^b$ is H or methyl; in an embodiment, a compound or a salt thereof in which $R^b$ is H; or in an embodiment, a compound or a salt thereof in which $R^b$ is methyl;

(10) A compound or a salt thereof in which $R^c$ is H, methyl or oxetanyl; in an embodiment, a compound or a salt thereof in which $R^c$ is H or methyl; in an embodiment, a compound or a salt thereof in which $R^c$ is H; or in an embodiment, a compound or a salt thereof in which $R^c$ is methyl;

(11) A compound or a salt thereof in which $R^d$ is H, methyl, —($CH_2)_2$OH, —($CH_2)_2$O—$CH_3$ or oxetanyl; in an embodiment, a compound or a salt thereof in which $R^d$ is —($CH_2)_2$OH or —($CH_2)_2$O—$CH_3$; in an embodiment, a compound or a salt thereof in which $R^d$ is —($CH_2)_2$OH; or in an embodiment, a compound or a salt thereof in which $R^d$ is —($CH_2)_2$O—$CH_3$;

(12) A compound or a salt thereof in which m is 1 or 2; in an embodiment, a compound or a salt thereof in which m is 1; or in an embodiment, a compound or a salt thereof in which m is 2;

(13) A compound or a salt thereof in which n is 1 or 2; in an embodiment, a compound or a salt thereof in which n is 1; or in an embodiment, a compound or a salt thereof in which n is 2; or

(14) A compound or a salt thereof that is a combination of arbitrary two or more of embodiments (1-1) to (13), which does not cause a contradiction.

Specific examples of the combination described in (14) include the following embodiments:

(15) A compound or a salt thereof in which $R^1$ is a group of the following formula (i), (ii), (iii) (iv) or (v):

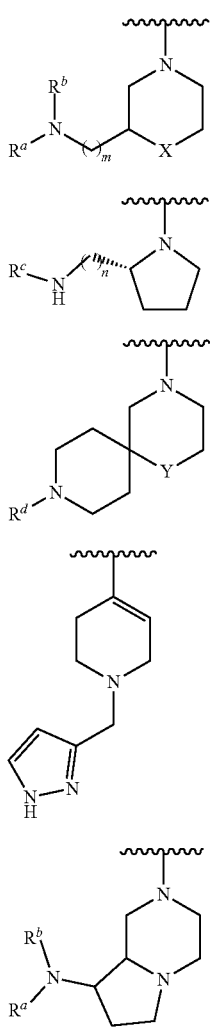

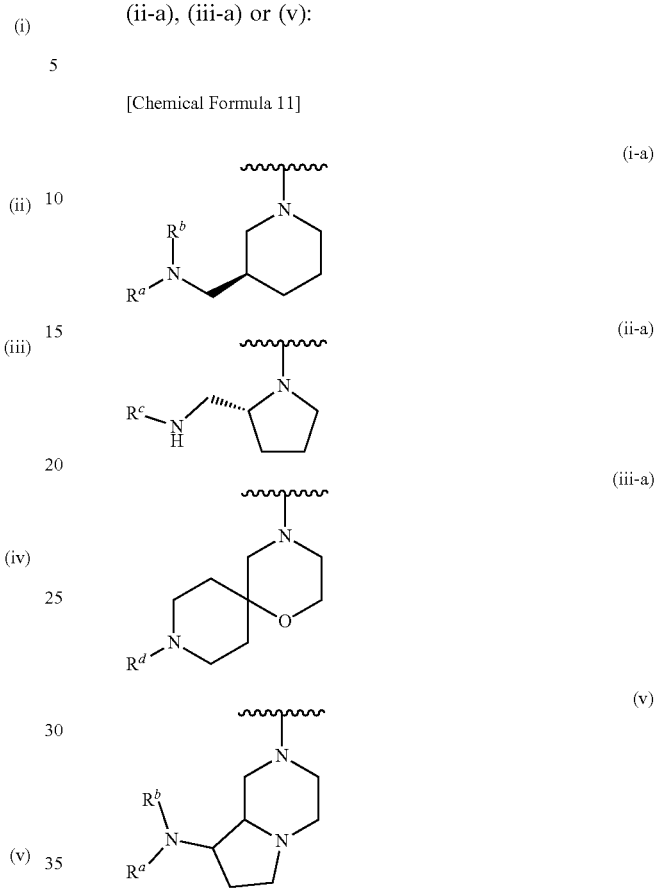

wherein R² is a C₁₋₆ alkyl, a C₃₋₅ cycloalkyl, an —O—(C₁₋₆ alkyl), methanesulphonyl, a halogeno-C₁₋₆ alkyl or a halogen; R³ is i) a phenyl optionally substituted with a group selected from the group consisting of a C₁₋₆ alkyl, a halogeno-C₁₋₆ alkyl, a C₃₋₅ cycloalkyl, an —O—(C₁₋₆ alkyl), an —O-(halogeno-C₁₋₆ alkyl), cyano, nitro, methanesulphonyl and a halogen, ii) a C₃₋₈ cycloalkyl optionally substituted with a group selected from the group consisting of a C₁₋₆ alkyl and a halogen, iii) a pyridyl optionally substituted with a group selected from the group consisting of a C₁₋₆ alkyl, a halogeno-C₁₋₆ alkyl, a C₃₋₅ cycloalkyl, an —O—(C₁₋₆ alkyl), an —O-(halogeno-C₁₋₆ alkyl), cyano, nitro, methanesulphonyl and a halogen, iv) a pyrazolyl optionally substituted with a group selected from the group consisting of a C₁₋₆ alkyl and a halogen, or v) a pyrrolidinyl optionally substituted with a C₁₋₆ alkyl; R⁴ is H or F; L is a bond, CO, SO₂, O or NH; X is CH₂, O or N-methyl; Y is CH₂ or O; Rᵃ is H or methyl; Rᵇ is H, methyl, ethyl or —(CH₂)₂O—CH₃; Rᶜ is H, methyl or oxetanyl; Rᵈ is H, methyl, —(CH₂)₂OH, —(CH₂)₂O—CH₃ or oxetanyl; m is 1 or 2; n is 1 or 2;

(16) The compound or the salt thereof described in (15) in which R² is a halogeno-C₁₋₆ alkyl or a halogen; L is a bond, O or NH; X is CH₂ or N-methyl; Rᶜ is H or methyl; m is 1;

(17) The compound or the salt thereof described in (16) in which R¹ is a group of the following formula (i-a), (ii-a), (iii-a) or (v):

[Chemical Formula 11]

(18) The compound or the salt thereof described in (17) in which R³ is a phenyl optionally substituted with a group selected from the group consisting of a C₁₋₆ alkyl and a halogen, or a C₃₋₅ cycloalkyl;

(19) The compound or the salt thereof described in (18) in which R² is CF₃, R⁴ is H, Rᵇ is H or methyl and Rᶜ is H.

Specific examples of the combination described in (14) include the following embodiments:

(20) A compound or a salt thereof in which R¹ is a group of the following formula (i), (ii), (iii) or (iv):

[Chemical Formula 12]

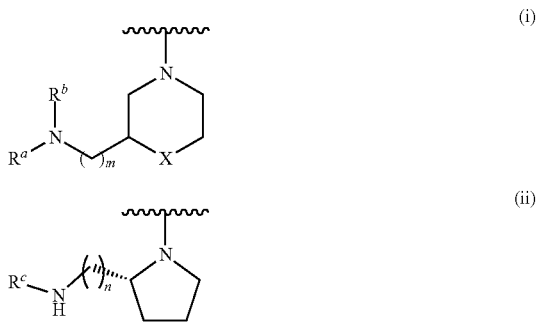

-continued (iii)

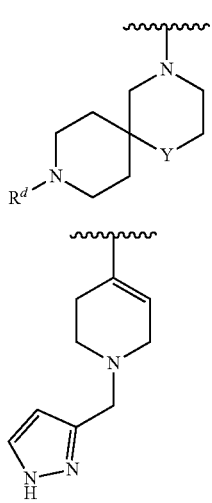

(iv)

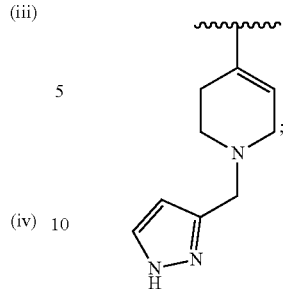

(iv)

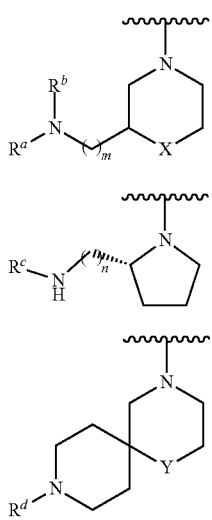

wherein $R^2$ is a halogeno-$C_{1-6}$ alkyl or a halogen; $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulphonyl and a halogen, ii) a $C_{3-8}$ cycloalkyl optionally substituted with a group selected from the group consisting of a $C_{1-6}$ alkyl and a halogen, iii) a pyridyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulphonyl and a halogen, iv) a pyrazolyl optionally substituted with a group selected from the group consisting of a $C_{1-6}$ alkyl and a halogen, or v) a pyrrolidinyl optionally substituted with a $C_{1-6}$ alkyl; $R^4$ is H or F; L is a bond, O or NH; X is $CH_2$, O or N-methyl; Y is $CH_2$ or O; $R^a$ is H or methyl; $R^b$ is H, methyl, ethyl or —$(CH_2)_2$O—$CH_3$; $R^c$ is H, methyl or oxetanyl; $R^d$ is H, methyl, —$(CH_2)_2$OH, —$(CH_2)_2$O—$CH_3$ or oxetanyl; m is 1 or 2; and n is 1 or 2;

(21) A compound or the salt thereof described in according to (20), in which $R^1$ is a group of formula (i), (ii), (iii) or (iv):

[Chemical Formula 13]

(i)

(ii)

(iii)

wherein $R^2$ is a halogeno-$C_{1-6}$ alkyl or a halogen; $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulphonyl and a halogen, ii) a $C_{3-8}$ cycloalkyl optionally substituted with a group selected from the group consisting of a $C_{1-6}$ alkyl and a halogen, iii) a pyridyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulphonyl and a halogen, iv) a pyrazolyl optionally substituted with a group selected from the group consisting of a $C_{1-6}$ alkyl and a halogen, or v) a pyrrolidinyl optionally substituted with a $C_{1-6}$ alkyl; $R^4$ is H or F; L is O or NH; X is $CH_2$ or N-methyl; Y is $CH_2$ or O; $R^a$ is H; $R^b$ is H, methyl, ethyl or —$(CH_2)_2$O-methyl; $R^c$ is H or methyl; $R^d$ is H, methyl, —$(CH_2)_2$OH, —$(CH_2)_2$O—$CH_3$ or oxetanyl; m is 1; and n is 1 or 2;

(22) The compound or the salt thereof described in (21) in which $R^1$ is a group of formula (i-a), (ii-a) or (iii-a):

[Chemical Formula 14]

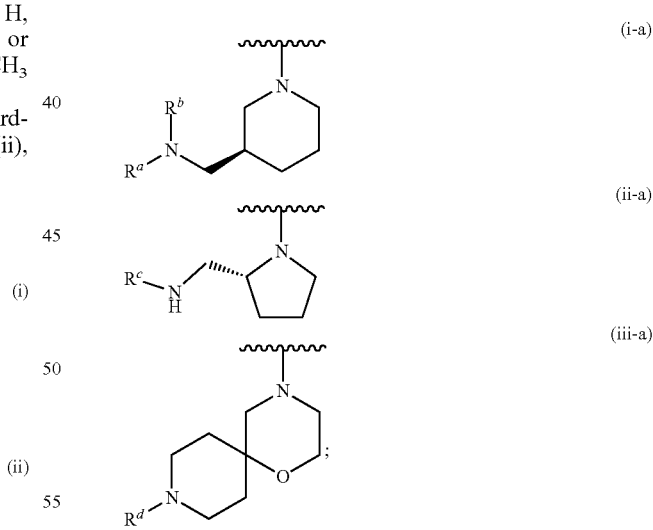

(23) The compound or the salt thereof described in (22) in which $R^3$ is a phenyl optionally substituted with a group selected from the group consisting of a $C_{1-6}$ alkyl and a halogen, or a $C_{3-5}$ cycloalkyl;

(24) The compound or the salt thereof described in (23) in which $R^2$ is $CF_3$, $R^4$ is H, $R^b$ is H or methyl and $R^c$ is H.

Examples of specific compounds encompassed by the present invention include the following compounds or salts thereof:

N-{2-[(3S)-3-(aminomethyl)piperidin-1-yl]-4-phenoxy-3-(trifluoromethyl)phenyl}-2-(pyridazin-4-yl)-1,3-thiazole-4-carboxamide;

N-{2-[(3S)-3-(aminomethyl)piperidin-1-yl]-4-(3-fluorophenoxy)-3-(trifluoromethyl)phenyl}-2-(pyridazin-4-yl)-1,3-thiazole-4-carboxamide;

N-{2-[9-(2-methoxyethyl)-1-oxa-4,9-diazaspiro[5.5]undecan-4-yl]-4-phenoxy-3-(trifluoromethyl) phenyl}-2-(pyridazin-4-yl)-1,3-thiazole-4-carboxamide;

N-{2-[(3S)-3-(aminomethyl)piperidin-1-yl]-4-(2-fluorophenoxy)-3-(trifluoromethyl)phenyl}-2-(pyridazin-4-yl)-1,3-thiazole-4-carboxamide;

N-[4-(2-fluorophenoxy)-2-{(3S)-3-[(methylamino)methyl]piperidin-1-yl}-3-(trifluoromethyl) phenyl]-2-(pyridazin-4-yl)-1,3-thiazole-4-carboxamide;

N-{2-[(2R)-2-(aminomethyl)pyrrolidin-1-yl]-4-phenoxy-3-(trifluoromethyl)phenyl}-2-(pyridazin-4-yl)-1,3-thiazole-4-carboxamide;

N-{2-[(8R,8aS)-8-aminohexahydropyrrolo[1,2-a]pyrazine-2(1H)-yl]-4-phenoxy-3-(trifluoromethyl)phenyl}-2-(pyridazin-4-yl)-1,3-thiazole-4-carboxamide; and N-{2-[(8R,8aS)-8-(dimethylamino)hexahydropyrrolo[1,2-a]pyrazine-2(1H)-yl]-4-phenoxy-3-(trifluoromethyl)phenyl}-2-(pyridazin-4-yl)-1,3-thiazole-4-carboxamide.

Examples of specific compounds encompassed by the present invention include the following compounds or salts thereof:

N-{2-[(3S)-3-(aminomethyl)piperidin-1-yl]-4-phenoxy-3-(trifluoromethyl)phenyl}-2-(pyridazin-4-yl)-1,3-thiazole-4-carboxamide;

N-{2-[(3S)-3-(aminomethyl)piperidin-1-yl]-4-(3-fluorophenoxy)-3-(trifluoromethyl)phenyl}-2-(pyridazin-4-yl)-1,3-thiazole-4-carboxamide;

N-{2-[9-(2-methoxyethyl)-1-oxa-4,9-diazaspiro[5.5]undecan-4-yl]-4-phenoxy-3-(trifluoromethyl) phenyl}-2-(pyridazin-4-yl)-1,3-thiazole-4-carboxamide;

N-{2-[(3S)-3-(aminomethyl)piperidin-1-yl]-4-(2-fluorophenoxy)-3-(trifluoromethyl)phenyl}-2-(pyridazin-4-yl)-1,3-thiazole-4-carboxamide;

N-[4-(2-fluorophenoxy)-2-{(3S)-3-[(methylamino)methyl]piperidin-1-yl}-3-(trifluoromethyl) phenyl]-2-(pyridazin-4-yl)-1,3-thiazole-4-carboxamide; and N-{2-[(2R)-2-(aminomethyl)pyrrolidin-1-yl]-4-phenoxy-3-(trifluoromethyl)phenyl}-2-(pyridazin-4-yl)-1,3-thiazole-4-carboxamide.

Examples of specific compounds encompassed by the present invention include the following compounds or salts thereof:

N-{2-[(3S)-3-(aminomethyl)piperidin-1-yl]-4-phenoxy-3-(trifluoromethyl)phenyl}-2-(pyridazin-4-yl)-1,3-thiazole-4-carboxamide mono[(2E)-but-2-enedioate];

N-{2-[(3S)-3-(aminomethyl)piperidin-1-yl]-4-(3-fluorophenoxy)-3-(trifluoromethyl)phenyl}-2-(pyridazin-4-yl)-1,3-thiazole-4-carboxamide mono[(2E)-but-2-enedioate];

N-{2-[(3S)-3-(aminomethyl)piperidin-1-yl]-4-(2-fluorophenoxy)-3-(trifluoromethyl)phenyl}-2-(pyridazin-4-yl)-1,3-thiazole-4-carboxamide mono[(2E)-but-2-enedioate];

N-[4-(2-fluorophenoxy)-2-{(3S)-3-[(methylamino)methyl]piperidin-1-yl}-3-(trifluoromethyl) phenyl]-2-(pyridazin-4-yl)-1,3-thiazole-4-carboxamide mono[(2E)-but-2-enedioate]; and N-{2-[(2R)-2-(aminomethyl)pyrrolidin-1-yl]-4-phenoxy-3-(trifluoromethyl)phenyl}-2-(pyridazin-4-yl)-1,3-thiazole-4-carboxamide mono[(2E)-but-2-enedioate].

The compound of formula (I) can have tautomers and geometric isomers depending on the type of a substituent. In the present description, the compound of formula (I) or a salt thereof may be described in only one isomer form, but the present invention encompasses other isomers, isolated forms of isomers, or mixtures thereof.

The compound of formula (I) or a salt thereof may have an asymmetric center or axial chirality, based on which enantiomers (optical isomers) can be present. The compound of formula (I) or a salt thereof encompass all of isolated individual enantiomers such as (R) and (S) configurations and mixtures thereof (including racemic mixtures or non-racemic mixtures). In an embodiment, the enantiomer is "stereochemically pure". The term "stereochemically pure" refers to a purity with which those skilled in the art can recognize the enantiomer as being substantially stereochemically pure. In another embodiment, the enantiomer is a compound having a stereochemical purity of, for example, 90% ee (enantiomeric excess) or more, 95% ee or more, 98% ee or more or 99% ee or more.

The salt of the compound of formula (I) is a pharmaceutically acceptable salt of the compound of formula (I), and an acid addition salt or a salt with a base may be formed depending on the type of a substituent. Specific examples thereof include acid addition salts with inorganic acids such as hydrochloric acid, hydrobromic acid, hydroiodic acid, sulfuric acid, nitric acid and phosphoric acid, and organic acids such as formic acid, acetic acid, propionic acid, oxalic acid, malonic acid, succinic acid, fumaric acid ((2E)-but-2-enedioic acid), maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid and glutamic acid; and salts with inorganic bases such as sodium, potassium, magnesium, calcium and aluminum, various amino acids such as acetylleucine, and amino acid derivatives.

Further, the present invention encompasses various hydrates, solvates and substances of crystalline polymorphism of the compounds of formula (I) and salts thereof.

Furthermore, the present invention encompasses pharmaceutically acceptable prodrugs of the compounds of formula (I). The pharmaceutically acceptable prodrug is a compound having a group which can be converted into an amino group, a hydroxyl group, a carboxyl group or the like by solvolysis or under physiological conditions. Examples of the group that forms the prodrug include groups as described in Prog. Med., 5, 2157-2161 (1985) and "Pharmaceutical research and development" (Hirokawa Shoten Co., 1990), Vol. 7, Molecular Design, 163-198.

The present invention encompasses all of compounds of formula (I) which are labeled with one or more pharmaceutically acceptable radioactive or non-radioactive isotopes, or salts thereof. Examples of preferred isotopes used for isotope labels for the compound of the present invention include isotopes of hydrogen (e.g. $^2H$ and $^3H$), carbon (e.g. $^{11}C$, $^{13}C$ and $^{14}C$), nitrogen (e.g. $^{13}N$ and $^{15}N$), oxygen (e.g. $^{15}O$, $^{17}O$ and $^{18}O$), fluorine (e.g. $^{18}F$), chlorine (e.g. $^{36}Cl$), iodine (e.g. $^{123}I$ and $^{125}I$), phosphorus (e.g. $^{32}P$) and sulfur (e.g. $^{35}S$).

The isotopically labeled compound of the invention of the present application can be used for studies on histological distributions of drugs and/or substrates. For example, radioactive isotopes such as tritium ($^3H$) and carbon 14 ($^{14}C$) can be used for this purpose from the viewpoint of ease of labeling and convenience of detection.

Replacement by a heavier isotope, for example replacement of hydrogen by deuterium ($^2H$) may be therapeutically advantageous because metabolic stability is improved (e.g. increased in vivo half-life, decreased necessary dose or declined drug interaction).

Replacement by positron-emitting isotopes (e.g. $^{11}$C, $^{18}$F, $^{15}$O and $^{13}$N) can be applied in positron emission tomography (PET) tests for examining the substrate acceptor occupancy rate.

The isotopically labeled compound of the present invention can be generally prepared by a conventional method known to those skilled in the art, or by the same production method as in Examples or Production Examples using appropriate isotopically labeled reagents instead of non-labeled reagents.

In powder X-ray diffraction described in the subject specification, the crystal lattice distance and the entire pattern are important for the identification of crystals in view of the characteristics of the data. A diffraction angle and intensity may slightly vary depending on the direction of crystal growth, the particle size, and the measuring conditions, and should not be interpreted strictly. As used herein, the diffraction angle (2θ) in the powder X-ray diffraction pattern is interpreted with a margin of error generally acceptable in the measurement, for example, a margin of error of ±0.2°. Moreover, for example, a peak which is nearby a peak derived from excipients and on a tilted baseline of the peak can visually shift by ±0.3° in the case that powder X-ray measurement is performed in the state of a mixture with excipients.

(Preparing Method)

The compound of formula (I) and a salt thereof can be prepared by applying various known synthesis methods by making use of characteristics based on the basic structure or the type of a substituent of the compound. Here, depending on the type of a functional group, replacement of the functional group by an appropriate protective group (group easily convertible into the functional group) during formation of an intermediate from a raw material may be effective as a production technique. Examples of the protective group include protective groups as described in P. G. M. Wuts and T. W. Greene, "Greene's Protective Groups in Organic Synthesis (Vol. 4, 2006)", and according to the reaction conditions, an appropriate protective group may be selected and used. In this method, such a protective group is introduced, and a reaction is carried out, followed by removing the protective group if necessary to obtain a desired compound.

The prodrug for the compound of formula (I) can be prepared by introducing a specific group during formation of an intermediate from a raw material as in the case of the above-described protective group, or by further carrying out a reaction using the resulting compound of formula (I). The reaction can be carried out by applying a method known to those skilled in the art, such as common esterification, amidation or dehydration.

Hereinafter, a typical method for preparing the compound of formula (I) will be described. Each production method can be carried out by referring to the references cited in the description. The production method according to the present invention is not limited to the example shown below.

In the present description, the following abbreviations may be used.

DMF=N,N-dimethylformamide, DMSO=dimethyl sulfoxide, EtOAc=ethyl acetate, EtOH=ethanol, Hex=hexane, MeCN=acetonitrile, MeOH=methanol, THF=tetrahydrofuran, DMI=1,3-dimethylimidazolidin-2-one, NMP=N-methyl-2-pyrrolidone, CH$_2$Cl$_2$=dichloromethane.

Boc=tert-butoxycarbonyl, Ph=phenyl, tBu=tert-butyl, Et=ethyl, Me=methyl, Ac=acetyl, Ns=2-nitrobenzenesulfonyl.

CDI=1,1'-carbonylbis(1H-imidazole), DCC=N,N'-dicyclohexylcarbodiimide, TEA=triethylamine, DIPEA=N,N-diisopropylethylamine, DABCO=1,4-diazabicyclo[2.2.2]octane, DPPA=diphenylphosphoryl azide, HATU=O-(7-azabenzotriazol-1-yl)-N,N,N',N'-tetramethyluronium hexafluorophosphate, HOBt=1-hydroxybenzotriazole, KOtBu=potassium tert-butoxide, NaOtBu=sodium tert-butoxide, NMO=N-methylmorpholine, Pd/C=palladium-carrying carbon, TFA=trifluoroacetic acid, TFAA=trifluoroacetic anhydride, WSC·HCl=N-[3-(dimethylamino)propyl]-N'-ethylcarbodiimide hydrochloride.

Pd(PPh$_3$)$_4$=tetrakis(triphenylphosphine)palladium, PdCl$_2$(PPh$_3$)$_2$=bis(triphenylphosphine)palladium (II) dichloride, Pd(dppf)Cl$_2$·CH$_2$Cl$_2$=[1,1'-bis(diphenylphosphino)ferrocene]palladium (II) dichloride dichloromethane adduct, Pd$_2$(dba)$_3$=(1E,4E)-1,5-diphenylpenta-1,4-dien-3-one/palladium (3:2).

brine=saturated NaCl aqueous solution, MgSO$_4$=anhydrous magnesium sulfate, Na$_2$SO$_4$=anhydrous sodium sulfate, NaHCO$_3$=sodium hydrogencarbonate, NH$_4$Cl=ammonium chloride, NaBH(OAc)$_3$=sodium triacetoxyborohydride.

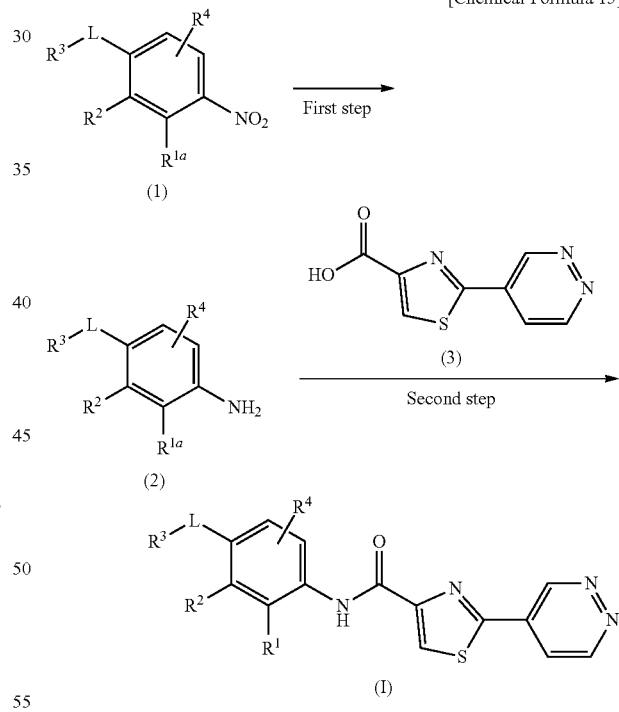

[Chemical Formula 15]

(wherein R$^{1a}$ represents R$^1$ or a protecting group-adduct of R$^1$)

First Step

This step is a method in which compound (1) is subjected to a reduction reaction to obtain compound (2).

This reaction can be carried out by stirring compound (1) and a metal at room temperature or under reflux by heating under acidic conditions in a mixed solvent of methanol, ethanol, 1,4-dioxane or the like and water for 1 hour to 5 days. As the acid, NH$_4$Cl, AcOH, HCl or the like is used. As the metal, Fe, Zn, Sn or the like is used.

In addition, this reaction can be carried out by stirring compound (1) in the presence of a metal catalyst under cooling or heating, preferably at room temperature, in a solvent inactive to the reaction, such as MeOH, EtOH or EtOAc, and a mixed solvent thereof, in a hydrogen atmosphere for 1 hour to 5 days. As the metal catalyst, palladium catalysts such as Pd/C, palladium black and palladium hydroxide-carrying carbon, platinum catalysts such as platinum-carrying carbon and platinum oxide, nickel catalysts such as reduced nickel and Raney nickel, and the like are used.

Second Step

This step is a method in which compound (2) and compound (3) are subjected to an amidation reaction, and substituents are then appropriately converted to obtain the compound of formula (I).

POCl$_3$ or SOCl$_2$, mixed acid anhydrides obtained by reaction of the compound with isobutyl chloroformate or the like, and active esters obtained by condensing the compound with HOBt or the like. This reaction can be carried out under cooling or under reflux by heating, preferably at −20° C. to 120° C., in a solvent inactive to the reaction, such as a halogenated hydrocarbon, an aromatic hydrocarbon or an ether.

After the amidation reaction, a protective group is introduced and/or removed if necessary, and substituents are appropriately converted to obtain the compound of formula (I). For example, if R$^{1a}$ of compound (3) is a protecting group-adduct of R$^1$, the protective group can be removed under appropriate reaction conditions to obtain the compound of formula (I).

Synthesis of Raw Material

[Chemical Formula 16]

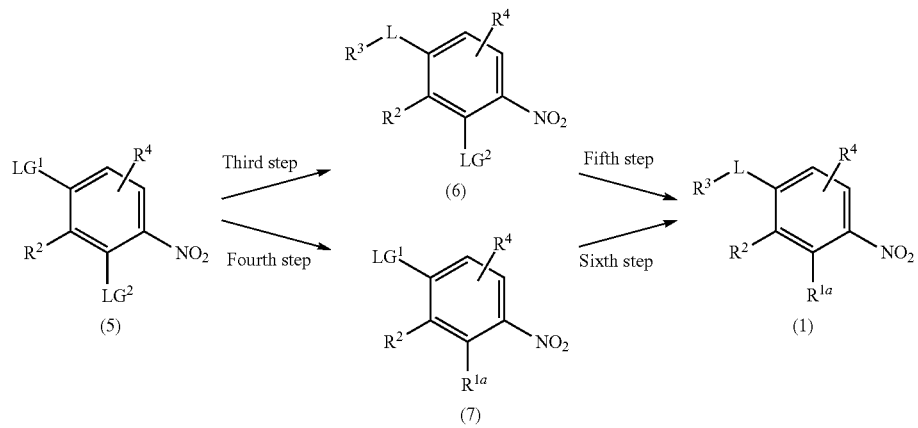

(wherein LG$^1$ and LG$^2$ each represent a leaving group. LG$^1$ and LG$^2$ are different from each other, which may be halogens etc.)

This production method is a method for preparing raw material compound (1).

Third Step

This step is a method in which compound (6) is prepared from compound (5) through an ipso-substitution reaction.

In this reaction, the compound is stirred under cooling or under reflux by heating, preferably at 0° C. to 120° C., in a solvent inactive to the reaction or under a solvent-free condition, typically for 0.1 hours to 5 days. The solvent used here is not particularly limited, and examples thereof include halogenated hydrocarbons such as CH$_2$Cl$_2$, 1,2-dichloroethane and chloroform, aromatic hydrocarbons such as benzene, toluene and xylene, ethers such as diethyl ether, THF, 1,4-dioxane and 1,2-dimethoxyethane, DMF, DMSO, NMP, EtOAc, MeCN, and mixtures thereof. It may be advantageous to carry out the reaction in the presence of an organic base such as TEA, DIPEA, NMO or DABCO or an inorganic base such as NaH, K$_2$CO$_3$, Na$_2$CO$_3$, Cs$_2$CO$_3$ or NaOtBu for causing the reaction to smoothly proceed.

In the amidation reaction, compound (2) and compound (3) are used in such a manner that the amounts of the compounds are equal to each other, or the amount of one of the compounds is excessive, and a mixture of the compounds is stirred in the presence of a condensing agent under cooling or heating, preferably at −20° C. to 60° C., in a solvent inactive to the reaction, typically for 0.1 hours to 5 days. The solvent used here is not particularly limited, and examples thereof include aromatic hydrocarbons such as benzene, toluene and xylene, halogenated hydrocarbons such as CH$_2$Cl$_2$, 1,2-dichloroethane and chloroform, ethers such as diethyl ether, THF, 1,4-dioxane and 1,2-dimethoxyethane, DMF, DMSO, EtOAc, MeCN, water, and mixtures thereof. Examples of the condensing agent include, but are not limited to, WSC·HCl, DCC, CDI, DPPA, POCl$_3$ and HATU. Use of an additive (e.g. HOBt) may be favorable to the reaction. It may be advantageous to carry out the reaction in the presence of an organic base such as TEA, DIPEA or NMO or an inorganic base such as K$_2$CO$_3$, Na$_2$CO$_3$ or KOH for causing the reaction to smoothly proceed.

In addition, an amidation reaction can be used in which compound (3) is converted into a reactive derivative, and then reacted with compound (2). Examples of the reactive derivative of compound (3) include acid halides obtained by reaction of the compound with a halogenating agent such as

Fourth Step

This step is a method in which compound (7) is prepared through a Suzuki coupling reaction using compound (5) and an organoboron compound, or a method in which compound (7) is prepared through a Buchwald-Hartwig reaction using compound (5) and an amine compound.

In this reaction, the compound is stirred at room temperature or under reflux by heating in the presence of a base and a palladium catalyst in a solvent inactive to the reaction typically for 0.1 hours to 5 days. The solvent used here is not particularly limited, and examples thereof include halogenated hydrocarbons such as $CH_2Cl_2$, 1,2-dichloroethane and chloroform, aromatic hydrocarbons such as benzene, toluene and xylene, ethers such as diethyl ether, THF, 1,4-dioxane and 1,2-dimethoxyethane, alcohols such as methanol, ethanol, isopropyl alcohol and butanol, DMF, DMSO, MeCN, DMI, water, and mixtures thereof. Examples of the base include inorganic bases such as NaH, $K_2CO_3$, $Na_2CO_3$, $Cs_2CO_3$, $K_3PO_4$ and CsF. Examples of the palladium catalyst include $Pd(PPh_3)_4$, $PdCl_2(PPh_3)_2$, $Pd(dppf)Cl_2 \cdot CH_2Cl_2$ and $Pd_2(dba)_3$. It may be advantageous to carry out the reaction in the presence of a ligand such as dicyclohexyl(2', 6'-dimethoxybiphenyl-2-yl)phosphine (SPhos) for causing the reaction to smoothly proceed. It may be advantageous to heat the reaction mixture by microwave irradiation for causing the reaction to smoothly proceed. As references for this reaction, for example, it is possible to refer to the following.

J. Am. Chem. Soc. 127, 4685-4696, 2005

Angew. Chem., Int. Ed. Engl. 34, 1384-1350, 1995

In addition, this step is a method in which compound (7) is prepared from compound (5) through an ipso-substitution reaction. The reaction conditions are the same as in the third step.

Fifth and Sixth Steps

This step is a method in which compound (1) is prepared from compound (6) or (7) through an ipso-substitution reaction.

The reaction conditions are the same as in the third step.

In an alternative method for preparing compound (1), compound (5a) in which $R^2$ of compound (5) is substituted with a leaving group such as halogens, can be used as a raw material (the leaving group such as halogens is referred to as $LG^3$, which differs from $LG^1$ and $LG^2$). Compound (7a) in which $R^2$ of compound (7) is substituted with $LG^3$, is prepared from compound (5a), as in the fourth step. Then, compound (1a) in which $R^2$ of compound (1) is substituted with $LG^3$, is prepared as in the sixth step, and compound (1) is prepared as in the fourth step.

The compound of formula (I) is isolated as a free compound, or a salt, a hydrate, a solvate or a crystal-polymorphic substance thereof, and purified. The salt of the compound of formula (I) can be prepared by subjecting the compound to a conventional salt formation reaction.

The isolation and purification is performed by applying normal chemical operations such as extraction, fractional crystallization and various kinds of chromatography.

Various isomers can be prepared by selection of an appropriate raw material compound, or separated by making use of a difference in physicochemical properties between isomers. For example, optical isomers can be obtained by a general method for optically resolving racemates (e.g. fractional crystallization to derive a diastereomer salt with an optically active base or acid, or chromatography using a chiral column), or prepared from an appropriate optically active raw material compound.

The pharmacological activity of the compound of formula (I) can be confirmed through the following test, or a known improvement test. In the present description, the dose of a test compound is shown in terms of a weight in a free form. When a commercially available reagent, kit or the like is used, the test can be conducted in accordance with the instructions of the commercially available product.

Test Example 1: Evaluation of DGK ξ Inhibitory Effect

The inhibitory effect of a test compound on human recombinant DGK ξ (Carna Biosciences, Inc., 12-410-20N) was examined by the following method in which detection is performed with ADP-Glo™ Kinase Assay (Promega Corporation).

To a 384-well plate (Greiner Bio-One Co., Ltd.), 3 μL of a DGK Δ enzyme dissolved in an assay buffer (40 mM Tris-HCl pH 7.5, 10 mM $MgCl_2$, 1 mM dithiothreitol (DTT) and 0.1 mg/mL bovine serum albumin (BSA)) (90 ng/mL) was added, and 3 μL of the test compound diluted with the same assay buffer was added so that an intended final concentration was obtained. The mixture was left standing at room temperature for 15 minutes, 3 μL of a substrate (150 μM 1-oleoyl-2-acetyl-sn-glycerol (Sigma-Aldrich Co. LLC.), 480 μM phosphatidylserine (Avanti Polar Lipids, Inc.) and 150 μM UltraPure-ATP (attached to ADP-Glo)) was then added, and the mixture was left standing at room temperature for 30 minutes to react. Thereafter, 3 μL of an ADP-Glo Reagent was added, and the mixture was left standing at room temperature for 40 minutes to stop the enzyme reaction. Further, 6 μL of a Kinase-Detection Reagent was added, the mixture was left standing at room temperature for 30 minutes, and the luminescence was then measured using ARVO X3 (PerkinElmer, Inc.). The half maximal inhibitory concentration ($IC_{50}$) was calculated by Sigmoid-Emax model non-linear regression analysis, where the signal value in solvent treatment was set to 0% inhibition and the signal value without addition of the DGK ξ enzyme was set to 100% inhibition. Table 1 shows the results for some test compounds of formula (I). In the table, Ex represents the number of each Example described below. Also, in the table, compound C (cpd. C) represents the test compound of the Example 199 described in the international publication WO 2008/054702.

TABLE 1

| Ex | $IC_{50}$ (nM) |
|---|---|
| 1 | 3 |
| 2 | 53 |
| 3 | 20 |
| 4 | 50 |
| 5 | 48 |
| 6 | 3 |
| 7 | 110 |
| 8 | 9 |
| 9 | 8 |
| 10 | 8 |
| 11 | 19 |
| 12 | 17 |
| 13 | 13 |
| 14 | 13 |
| 15 | 7 |
| 16 | 41 |
| 17 | 13 |

TABLE 1-continued

| Ex | IC$_{50}$ (nM) |
|---|---|
| 18 | 19 |
| 19 | 15 |
| 20 | 44 |
| 21 | 6 |
| 22 | 5 |
| 23 | 10 |
| 24 | 11 |
| 25 | 42 |
| 26 | 46 |
| 27 | 90 |
| 28 | 42 |
| 29 | 426 |
| 30 | 39 |
| 31 | 23 |
| 32 | 31 |
| 33 | 5 |
| 34 | 12 |
| 35 | 2 |
| 36 | 13 |
| 37 | 26 |
| 38 | 3 |
| 39 | 7 |
| 40 | 50 |
| 41 | 11 |
| 42 | 23 |
| 43 | 36 |
| 44 | 19 |
| 45 | 24 |
| 46 | 40 |
| 47 | 147 |
| 48 | 8 |
| 49 | 10 |
| 50 | 23 |
| 51 | 16 |
| 52 | 23 |
| 53 | 27 |
| 54 | 17 |
| 55 | 99 |
| 56 | 29 |
| 57 | 240 |
| 58 | 144 |
| 59 | 2 |
| 60 | 3 |
| 61 | 3 |
| 62 | 10 |
| 63 | 429 |
| 64 | 30 |
| 65 | 12 |
| 66 | 32 |
| 67 | 12 |
| 68 | 5 |
| 69 | 13 |
| 70 | 7 |
| 71 | 44 |
| 72 | 18 |
| 73 | 0.7 |
| 74 | 41 |
| 75 | 6 |
| 76 | 6 |
| 77 | 2 |
| 78 | 5 |
| 79 | 47 |
| 80 | 0.7 |
| 81 | 152 |
| 82 | 3 |
| 83 | 5 |
| 84 | 6 |
| 85 | 15 |
| 86 | 3 |
| 87 | 20 |
| cpd. C | >2000 |

Test Example 2: Evaluation of IL-2 Production in Human T Cell Leukemia Cell Line Jurkat E6.1

The effect of the test compound on the IL-2 production by T cell receptor (TCR) stimulation (anti-CD3/anti-CD28) in Jurkat E6.1 cells (ECACC, 88042803) was evaluated.

A 5 μg/mL anti-CD3 antibody (eBioscience, Inc., OKT3 clone) diluted with phosphate buffer saline (PBS) was added to a 96-well plate (Iwaki & Co., Ltd.) at 50 μL/well, and left standing at 4° C. for 12 hours or more to provide an anti-CD3 antibody-coated plate in advance. When the plate was used for experiments, the plate was washed with 200 μL of PBS once, an anti-CD28 antibody (eBioscience, Inc., 28.2 clone) diluted to a concentration of g/mL with a culture medium (RPMI1640 (Sigma-Aldrich Co. LLC.) containing 10% fetal bovine serum (Hyclone Laboratories, Inc.)) was then added at 10 μL/well, and the plate was used for assay as a culture plate for TCR stimulation.

Subsequently, the test compound was mixed with Jurkat E6.1 cells in such a manner that an intended final concentration was obtained, and the mixture was plated at 90 μL/well so that the number of cells per well was 1×10$^5$ (that is, finally the culture was performed at 1×10$^5$ cells/100 μL/well). For culture cell conditions, the culture was performed at 37° C. in the presence of 5% $CO_2$ using RPMI1640 medium containing 10% fatal bovine serum.

After 24 hours, the culture supernatant was collected, and IL-2 was quantitatively determined using AlphaLISA human IL2 Immunoassay Research Kit (PerkinElmer, Inc.). The IL-2 measurement was performed under Alpha Screen standard setting conditions (the fluorescence intensity at 570 nm was measured with an excitation wavelength of 680 nm) using EnVision 2104-0010 and EnVision 2104-0020 (PerkinElmer, Inc.). The IL-2 quantitative value of the solvent treatment control was set to 1, and the test compound concentration at which the IL-2 quantitative value of the test compound treatment sample increased to 10 times the IL-2 quantitative value of the control ($EC_{10fold}$) was calculated by inverse estimation with the aid of Sigmoid-Emax model non-linear regression analysis. Table 2 shows the results for some test compounds of formula (I). In the table, Ex represents the number of each Example described below.

TABLE 2

| Ex | $EC_{10fold}$ (nM) |
|---|---|
| 9 | 18 |
| 10 | 173 |
| 11 | 32 |
| 33 | 9 |
| 34 | 30 |
| 59 | 36 |
| 78 | 27 |
| 80 | 5 |

Test Example 3: Evaluation of Antitumor Effect in Syngeneic Mouse Model Bearing Mouse Colon Adenocarcinoma Cell Line MC38

A cell suspension liquid prepared by suspending MC38 cells (supplied from National Cancer Institute) in PBS at 4.0×10$^6$ cells/mL was subcutaneously inoculated into 6-week-old female mice ($C_{57}BL/6J$ from Charles River Laboratories Japan, Inc.) in a volume of 50 μL. 4 days after the inoculation, the mice were grouped in such a manner that there was substantially no difference in tumor volume between groups, and administration of the test compound was started. The test was conducted with a solvent group and a test compound administration group each having 10 mice. 0.5% methylcellulose (Shin-Etsu Chemical Co., Ltd.) was orally administered to the solvent group, and 0.5% methylcellulose mixed with the test compound was orally administered to the test compound administration group. The administration was performed twice a day from day 1 to day 10 and once a day on day 11, and the tumor diameter and the body weight were measured twice a week. The following expression was used for calculation of the tumor volume.

[tumor volume (mm$^3$)]=[tumor major diameter (mm)]×[tumor minor diameter (mm)]$^2$×0.5

The relative tumor growth inhibition (%) of the test compound was calculated, where the tumor volume of the test compound administration group immediately before the start of administration was set to 100% inhibition, and the tumor volume of the solvent group on the last day of administration was set to 0% inhibition. Table 3 shows the results for some test compounds of formula (I). In the table, Ex represents the number of each Example described below.

TABLE 3

| Ex | Dose (mg/kg) | Antitumor effect |
|----|--------------|------------------|
| 9  | 5            | 64% Inhibition   |
| 10 | 4.7          | 60% Inhibition   |
| 11 | 5            | 63% Inhibition   |
| 33 | 5            | 36% Inhibition   |
| 34 | 5            | 55% Inhibition   |

Test Example 4: Evaluation of Antitumor Effect in Syngeneic Mouse Model Bearing Mouse Melanoma Cell Line B16-F1

A cell suspension liquid prepared by suspending B16-F1 cells (ATCC, CRL-6323) in PBS at 2.0×10$^6$ cells/mL or 1.0×10$^7$ cells/mL was subcutaneously inoculated into 5-week-old female mice (C$_{57}$BL/6J from Charles River Laboratories Japan, Inc.) in a volume of 50 μL. 5 days after the inoculation, the mice were grouped in such a manner that there was substantially no difference in tumor volume between groups, and administration of the test compound was started. The test was conducted with a solvent group and a test compound administration group each having 10 mice. 0.5% methylcellulose was orally administered to the solvent group, and 0.5% methylcellulose mixed with the test compound was orally administered to the test compound administration group. The administration was performed according to the regimen described in Table 4, and the tumor diameter and the body weight were measured twice a week. The following expression was used for calculation of the tumor volume.

[tumor volume (mm$^3$)]=[tumor major diameter (mm)]×[tumor minor diameter (mm)]$^2$×0.5

The relative tumor growth inhibition (%) of the test compound was calculated, where the tumor volume of the test compound administration group immediately before the start of administration was set to 100% inhibition, and the tumor volume of the solvent group on the day after the last administration was set to 0% inhibition. Table 4 shows the results for some test compounds of formula (I). In the table, Ex represents the number of each Example described below.

TABLE 4

| Ex | Dose (mg/kg) | Frequency of administration | Duration of administration (day) | Number of cells for inoculation (cell number) | Antitumor effect |
|----|--------------|-----------------------------|----------------------------------|-----------------------------------------------|------------------|
| 9  | 0.5          | 2/day                       | 10                               | 5 × 10$^5$                                    | 36% Inhibition   |
| 10 | 0.1          | 1/day                       | 8                                | 1 × 10$^5$                                    | 42% Inhibition   |
| 34 | 1.5          | 2/day                       | 10                               | 5 × 10$^5$                                    | 48% Inhibition   |
| 59 | 0.1          | 1/day                       | 8                                | 1 × 10$^5$                                    | 46% Inhibition   |
| 78 | 0.3          | 1/day                       | 10                               | 1 × 10$^5$                                    | 30% Inhibition   |
| 80 | 0.03         | 1/day                       | 10                               | 1 × 10$^5$                                    | 30% Inhibition   |

The results of the above test showed that some compounds of formula (I) had DGK ξ inhibitory effect (Test Example 1). It was also confirmed that some compounds of formula (I) had the capacity to produce IL-2 in human T cell leukemia cell line (Test Example 2). Further, it was confirmed that some compounds of formula (I) had an antitumor effect in the mouse model (Test Examples 3 and 4). In particular, it was confirmed that some compounds of formula (I) showed an antitumor effect in the mice bearing B16-F1 cells, which were used in the Test Example 4, although it is generally known that anti-PD-1 antibody/anti-PD-L1 antibody does not show a pharmacological efficacy in B16-F1 cells. Therefore, the compound of formula (I) can be used for treatment etc. of a cancer related to activation of immune cells or a cancer having resistance to anti-PD-1 antibody/anti-PD-L1 antibody therapy, particularly a cancer related to activation of immune cells, which has resistance to anti-PD-1 antibody/anti-PD-L1 antibody therapy, etc.

A pharmaceutical composition containing one or more of the compounds of formula (I) or salts thereof as active ingredients can be prepared by a commonly used method with an excipient commonly used in the art, i.e. an excipient for pharmaceutical use, a carrier for pharmaceutical use, or the like.

The administration may be either oral administration with tablets, pills, capsules, granules, powders, solutions or the like, or parenteral administration with injection preparations for intraarticular injection, intravenous injection, intramuscular injection or the like, suppositories, eye-drops, eye ointments, transdermal solutions, ointments, transdermal patches, transmucosal solutions, transmucosal patches, inhalations or the like.

As a solid composition for oral administration, a tablet, a powder, a granule or the like is used. In such a solid composition, one or more active ingredients are mixed with at least one inactive excipient. The composition may conventionally contain inactive additives, for example a lubricant, a disintegrant, a stabilizer and a solubilizing agent. The tablet, powder, granule or pill may be coated with a wax, a sugarcoating or a stomach-soluble or enteric substance film.

Liquid compositions for oral administration include pharmaceutically acceptable emulsions, solutions, suspensions, syrups or elixirs, and contain a commonly used inactive diluents, for example purified water or ethanol. Such a liquid composition may contain adjuvants such as a solubilizer, a wetting agent and a suspension, a sweetening agent, a flavor, a fragrance and a preservative in addition to the inactive diluent.

The injection preparation for parenteral administration contains a sterile aqueous or nonaqueous solution, a suspension or an emulsion. Examples of the aqueous solvent include distilled water for injection of physiological saline solutions. Examples of the nonaqueous solvent include alcohols such as ethanol. Such a composition may further contain a tonicity agent, a preservative, a wetting agent, an emulsifier, a dispersant, a stabilizer or a solubilizing agent. The composition is sterilized by, for example, filtration involving passage through a bacteria retention filter, addition of a bactericide or irradiation. In addition, a sterile solid composition can be prepared, and dissolved or suspended in sterile water or a sterile solvent for injection before use.

The external preparation encompasses ointments, plasters, creams, gelatinous preparations, cataplasms, sprays, lotions, eye-drops, and eye ointments. The external preparation contains a commonly used ointment base, lotion base, aqueous or nonaqueous solution, suspension, emulsion or the like.

The transmucosal preparation such as an inhalation or a nasal preparation is solid, liquid or semisolid, and can be prepared in accordance with a known conventional method. For example, a known excipient, and a pH adjuster, a preservative, a surfactant, a lubricant, a stabilizer, a thickener and the like may be added to the transmucosal preparation, as appropriate. For administration, an appropriate device for inhalation or insufflation can be used. For example, using a known device such as a metered administration/inhalation device, or a sprayer, the compound can be administered alone, as powder of a prescribed mixture, or a solution or suspension liquid obtained by combining the compound with a pharmaceutically acceptable carrier. The dry powder inhaler or the like may be one for single-dose administration or multi-dose administration, and enables use of dry powder or a dry powder-containing capsule, or may be in the form of a press aerosol spray using an appropriate ejection agent, for example a suitable gas such as a chlorofluoroalkane or carbon dioxide.

Normally, in the case of oral administration, the appropriate daily dose per body weight is about 0.001 to 100 mg/kg, preferably 0.1 to 30 mg/kg, more preferably 0.1 to 10 mg/kg, in a single dose or 2 to 4 divided doses. In the case of intravenous administration, the appropriate daily dose per body weight is about 0.0001 to 10 mg/kg in a single dose or two or more divided doses. In the case of transmucosal administration, the daily dose per body weight is about 0.001 to 100 mg/kg in a single dose or two or more divided doses. The dose is appropriately determined with consideration given to a symptom, an age, a sex and the like.

Depending on an administration route, a dosage form, an administration site, and types of excipients and additives, the pharmaceutical composition according to the present invention contains one or more compounds of formula (I) or salts thereof as active ingredients in an amount of 0.01 to 100 wt %, or 0.01 to 50 wt % in an embodiment.

The compound of formula (I) can be used in combination with various therapeutic agents or prophylactic agents for diseases against which the compound of formula (I) may be effective. The combined use may be simultaneous administration, separate and sequential administration, or administration at a desired time interval. Preparations for simultaneous administration may be in the form of a combination preparation, or may be separately formulated preparations.

EXAMPLES

Hereinafter, the method for preparing the compound of formula (I) will be described in more detail by way of Examples. The present invention is not limited to the compounds described in Examples. Methods for preparing raw material compounds will be shown in production examples. The method for preparing the compound of formula (I) is not limited to the specific methods of Examples shown below, and the compound of formula (I) can be also prepared by a combination of these production methods, or methods obvious to those skilled in the art.

In the present description, naming software such as ACD/Name (registered trademark)(Advanced Chemistry Development, Inc.) may be used for naming a compound.

For convenience, mol/l as a unit of concentration is represented by M. For example, the 1 M sodium hydroxide aqueous solution means a sodium hydroxide aqueous solution at 1 mol/l.

In the present description, results of powder X-ray diffraction were measured using Empyrean under the following conditions:
tube: Cu; tube current: 40 mA; tube voltage: 45 kV; step width: 0.013°; wave length: 1.5418 Å; measurement range of diffraction angle (2θ): 2.5-40°.

Preparation Example 1

To a mixture of 2-bromo-4-fluoro-1-nitro-3-(trifluoromethyl)benzene (15 g), phenol (4.91 g) and NMP (150 mL) was added $K_2CO_3$ (14.4 g), and the reaction mixture was stirred at 50° C. for 16 hours. The reaction mixture was cooled to room temperature, EtOAc and water were then added, and the aqueous layer was separated. The aqueous layer was extracted with EtOAc, and the combined organic layers were washed with water and brine, dried with $MgSO_4$, and concentrated under reduced pressure. The residue was purified by silica gel column chromatography (Hex/EtOAc) to give 2-bromo-1-nitro-4-phenoxy-3-(trifluoromethyl)benzene (18.4 g).

Preparation Example 13

To a mixture of 2-chloro-4-fluoro-1-nitro-3-(trifluoromethyl)benzene (4.3 g), 1-(tert-butoxycarbonyl)-1,2,3,6-tetrahydro-4-(4,4,5,5-tetramethyl-1,3,2-dioxaborolan-2-yl)pyridine (4.5 g), Pd(dppf)$Cl_2 \cdot CH_2Cl_2$ (590 mg) and $K_2CO_3$ (4 g) were added 1,4-dioxane (45 mL) and water (9 mL), and the reaction mixture was stirred under an argon atmosphere at 100° C. for 20 hours. The reaction mixture was cooled to room temperature, water and EtOAc were then added, and the resulting mixture was filtered through celite, and then extracted with EtOAc. The organic layer was dried over $MgSO_4$, and concentrated under reduced pressure. The residue was purified by silica gel column chromatography (Hex/EtOAc) to give tert-butyl 4-[3-fluoro-6-nitro-2-(trifluoromethyl)phenyl]-3,6-dihydropyridine-1(2H)-carboxylate (4.65 g).

Preparation Example 16

Under a nitrogen atmosphere, to a mixture of 2-bromo-4-fluoro-1-nitro-3-(trifluoromethyl)benzene (2 g), tert-butyl {[(3R)-piperidin-3-yl]methyl}carbamate (1.63 g), $K_2CO_3$ (2.87 g) and 1,4-dioxane (20 mL) was added PdCl$_2$(PPh$_3$)$_2$ (487 mg), and the reaction mixture was stirred at 100° C. for 3 hours. The reaction mixture was cooled to room temperature, water was then added, the resulting mixture was extracted with EtOAc, and the extract was concentrated under reduced pressure. The residue was purified by silica gel column chromatography (Hex/EtOAc) to give tert-butyl ({(3S)-1-[3-fluoro-6-nitro-2-(trifluoromethyl)phenyl]piperidin-3-yl}methyl)carbamate (1.70 g) as a solid.

Preparation Example 17

To a mixture of tert-butyl 4-[3-fluoro-6-nitro-2-(trifluoromethyl)phenyl]-3,6-dihydropyridine-1(2H)-carboxylate (4.6 g), phenol (1.3 g) and NMP (23 mL) was added sodium hydride (60% oil dispersion, 570 mg) under ice cooling, and the resulting mixture was stirred under ice cooling under an argon atmosphere for 1 hour. Under ice cooling, water was added, and the resulting mixture was extracted with EtOAc. The organic layer was dried over $MgSO_4$, and concentrated under reduced pressure. The residue was purified by silica gel column chromatography (Hex/EtOAc) to give tert-butyl 4-[6-nitro-3-phenoxy-2-(trifluoromethyl)phenyl]-3,6-dihydropyridine-1(2H)-carboxylate (5.18 g).

Preparation Example 21

Under ice cooling, to a mixture of cyclopropanol (0.10 mL), NaOtBu (205 mg) and DMF (6 mL) was added tert-butyl ({(3S)-1-[3-fluoro-6-nitro-2-(trifluoromethyl)phenyl]piperidin-3-yl}methyl)carbamate (300 mg), and the reaction mixture was stirred at room temperature for 1 hour. The reaction was quenched with water, the mixture was extracted with EtOAc, and the organic layer was concentrated under reduced pressure. The residue was purified by silica gel column chromatography (Hex/EtOAc) to give tert-butyl ({(3S)-1-[3-(cyclopropyloxy)-6-nitro-2-(trifluoromethyl)phenyl]piperidin-3-yl}methyl)carba mate (250 mg) as a solid.

Preparation Example 30

To a mixture of tert-butyl (3S)-3-[(1,3-dioxo-1,3-dihydro-2H-isoindol-2-yl)methyl]piperidine-1-carboxylate (8.106 g) and ethanol (60 mL) was added 4 M HCl/1,4-dioxane solution (30 mL), and the reaction mixture was stirred at room temperature for 11 hours. The reaction mixture was concentrated under reduced pressure, and the residue was crystallized from ethanol and diethyl ether. The crystallized solid substance was taken by filtration, and washed with diethyl ether. The solid substance taken by filtration was dried under reduced pressure to give 2-{[(3R)-piperidin-3-yl]methyl}-1H-isoindole1,3(2H)-dione monohydrochloride (5.695 g) as a solid.

Preparation Example 31

To a mixture of [(3S)-1-(tert-butoxycarbonyl)piperidin-3-yl]acetic acid (2.9 g) and $NH_4Cl$ (960 mg) were added $CH_2Cl_2$ (24 mL), water (12 mL), WSC·HCl (2.5 g), TEA (5.8 mL) and HOBt (1.8 g), and the reaction mixture was stirred overnight at room temperature. 1 M hydrochloric acid was added to the reaction mixture to a pH of 2 to 3, and the mixture was then extracted using ISOLUTE (registered trademark) Phase Separator. The separated organic layer was washed with saturated $NaHCO_3$ aqueous solution, and concentrated under reduced pressure to give tert-butyl (3S)-3-(2-amino-2-oxoethyl)piperidine-1-carboxylate (2.7 g).

Preparation Example 32

To a mixture of tert-butyl (3S)-3-(2-amino-2-oxoethyl)piperidine-1-carboxylate (335 mg) and THF (7 mL) was added Lithium aluminum hydride (130 mg) under ice cooling, and the reaction mixture was stirred overnight at room temperature. Under ice cooling, water (130 µL), a 1 M sodium hydroxide aqueous solution (130 µL) and water (390 µL) were added, and the resulting mixture was then diluted with 10% methanol/$CH_2Cl_2$, and stirred at room temperature for 1 hour. After an insoluble material was separated by filtration through celite, and the filtrate was concentrated under reduced pressure. $CH_2Cl_2$ (4 mL) and DIPEA (360 µL) were added to the residue at room temperature, TFAA (240 µL) was then added under ice cooling, and the reaction mixture was stirred overnight at room temperature. A saturated $NH_4Cl$ aqueous solution was added, the resulting mixture was extracted using ISOLUTE (registered trademark) Phase Separator, and the extract was concentrated under reduced pressure. The residue was purified by silica gel column chromatography (Hex/EtOAc) to give tert-butyl (3S)-3-[2-(2,2,2-trifluoroacetamide)ethyl]piperidine-1-carboxylate (139 mg).

Preparation Example 33

To a mixture of tert-butyl (3S)-3-[2-(2,2,2-trifluoroacetamide)ethyl]piperidine-1-carboxylate (137 mg) and diethyl ether (1 mL) was added 4 M HCl/1,4-dioxane solution (1 mL) at room temperature, and the reaction mixture was stirred overnight. The reaction mixture was concentrated under reduced pressure to give 2,2,2-trifluoro-N-{2-[(3S)-piperidin-3-yl]ethyl}acetamide monohydrochloride (117 mg).

Preparation Example 34

To a mixture of 2-bromo-1-nitro-4-phenoxy-3-(trifluoromethyl)benzene (4.15 g) and 1,4-dioxane (60 mL) were added DIPEA (3 mL) and tert-butyl {[(3R)-piperidin-3-yl]methyl}carbamate (3 g), and the reaction mixture was stirred overnight at 100° C. The reaction mixture was cooled to room temperature, water was then added, and the resulting mixture was extracted with EtOAc. The extract was dried over $MgSO_4$, and then concentrated under reduced pressure, and the residue was purified by silica gel column chromatography (Hex/EtOAc) to give tert-butyl ({(3S)-1-[6-nitro-3-phenoxy-2-(trifluoromethyl)phenyl]piperidin-3-yl}methyl)carbamate (4.87 g).

Preparation Example 60

Under an argon atmosphere, to a mixture of tert-butyl (3{(3S)-1-[3-(2-fluorophenoxy)-6-nitro-2-(trifluoromethyl)phenyl]piperidin-3-yl}methyl)carbamate (3.5 g), iodomethane (860 µL) and DMF (35 mL) was added sodium hydride (60% oil dispersion, 410 mg) in four parts under ice cooling, and the reaction mixture was stirred at room temperature for 3 hours. Under ice cooling, the reaction was quenched with water. The mixture was extracted with EtOAc. The organic layer was washed with water and brine, dried over $MgSO_4$, and concentrated under reduced pressure. The residue was purified by silica gel column chromatography (Hex/EtOAc) to give tert-butyl ({(3R)-1-[3-(2-fluorophenoxy)-6-nitro-2-(trifluoromethyl)phenyl]piperidin-3-yl}methyl)(methyl) carbamate (3.44 g) as a solid.

Preparation Example 68

To a mixture of tert-butyl (2R)-2-(hydroxymethyl)-4-[6-nitro-3-phenoxy-2-(trifluoromethyl)phenyl]piperazine-1-carboxylate (110 mg) and $CH_2Cl_2$ (2 mL) was added A Dess-Martin reagent (120 mg) under ice cooling, and the reaction mixture was stirred at room temperature for 1 hour. The Dess-Martin reagent (120 mg) was further added, and the resulting mixture was stirred at room temperature for 30 minutes. A 10% sodium sulfite aqueous solution and a saturated $NaHCO_3$ aqueous solution were added to the reaction mixture under ice cooling, and the resulting mixture was stirred at room temperature for 30 minutes, and extracted using ISOLUTE (registered trademark) Phase Separator. The extract was concentrated under reduced pressure. The resulting residue was purified by silica gel column chromatography (Hex/EtOAc) to give tert-butyl (2R)-2-formyl-4-[6-nitro-3-phenoxy-2-(trifluoromethyl)phenyl]piperazine-1-carboxylate (86 mg).

Preparation Example 69

To a solution of tert-butyl (2R)-2-formyl-4-[6-nitro-3-phenoxy-2-(trifluoromethyl)phenyl]piperazine-1-carboxylate (84 mg) in $CH_2Cl_2$ (1 mL) were added 2 M methylamine/THF solution (170 μL), acetic acid (20 μL) and NaBH(OAc)$_3$ (75 mg), and the reaction mixture was stirred at room temperature for 2 hours. A saturated NaHCO$_3$ aqueous solution was added to the reaction mixture, the resulting mixture was extracted using ISOLUTE (registered trademark) Phase Separator, and the extract was concentrated under reduced pressure to give tert-butyl (2S)-2-[(methylamino)methyl]-4-[6-nitro-3-phenoxy-2-(trifluoromethyl)phenyl]piperazine-1-carboxylate (93 mg).

Preparation Example 70

To a mixture of tert-butyl (2S)-2-[(methylamino)methyl]-4-[6-nitro-3-phenoxy-2-(trifluoromethyl)phenyl]piperazine-1-carboxylate (93 mg) and $CH_2Cl_2$ (1 mL) were added DIPEA (50 μL) and TFAA (35 μL) under ice cooling, and the reaction mixture was stirred at room temperature for 1 hour. DIPEA (50 μL) and TFAA (35 μL) were added to the reaction mixture, and the resulting mixture was stirred at room temperature for 15 minutes. A saturated NH$_4$Cl aqueous solution was added to the reaction liquid, the resulting mixture was extracted using ISOLUTE (registered trademark) Phase Separator, and the extract was concentrated under reduced pressure. The residue was purified by silica gel column chromatography (chloroform/methanol) to give tert-butyl (2R)-2-{[methyl(trifluoroacetyl)amino]methyl}-4-[6-nitro-3-phenoxy-2-(trifluoromethyl)phenyl]piperazine-1-carboxylate (81 mg).

Preparation Example 71

To a mixture of tert-butyl (2R)-2-formyl-4-[6-nitro-3-phenoxy-2-(trifluoromethyl)phenyl]piperazine-1-carboxylate (1.04 g) and $CH_2Cl_2$ (10 mL) were added O-benzylhydroxylamine (320 μL), acetic acid (180 μL) and NaBH(OAc)$_3$ (670 mg), and the resulting mixture was stirred overnight at room temperature. Sodium cyanoborohydride (200 mg) was added to the reaction mixture, and the resulting mixture was stirred at room temperature for 3 hours. Sodium cyanoborohydride (200 mg) was added thereto, and the resulting mixture was stirred overnight at room temperature. Methanol (3 mL) was added, and the resulting mixture was stirred overnight. A saturated NaHCO$_3$ aqueous solution was added, the resulting mixture was stirred at room temperature for 1 hour, and extracted using ISOLUTE (registered trademark) Phase Separator, and the extract was concentrated under reduced pressure. The residue was dissolved in $CH_2Cl_2$ (10 mL), DIPEA (720 μL) was added, TFAA (450 μL) was then added under ice cooling, and the reaction mixture was stirred at room temperature for 30 minutes. A saturated NH$_4$Cl aqueous solution was added, the resulting mixture was extracted using ISOLUTE (registered trademark) Phase Separator, and the extract was concentrated under reduced pressure. The residue was purified by silica gel chromatography (Hex/EtOAc) to give tert-butyl (2R)-2-{[(benzyloxy)amino]methyl}-4-[6-nitro-3-phenoxy-2-(trifluoromethyl)phenyl]piperazine-1-carboxylate (426 mg).

Preparation Example 72

To a mixture of {(2R)-1-[3-(2-fluorophenoxy)-6-nitro-2-(trifluoromethyl)phenyl]pyrrolidin-2-yl}methanol (510 mg) and $CH_2Cl_2$ (5 mL) were added Pyridine (310 μL) and acetic anhydride (360 μg) under ice cooling, and the resulting mixture was stirred overnight at room temperature. A saturated NH$_4$Cl aqueous solution was added, the resulting mixture was extracted using ISOLUTE (registered trademark) Phase Separator, and the extract was concentrated under reduced pressure. The residue was purified by silica gel column chromatography (Hex/EtOAc) to give {(2R)-1-[3-(2-fluorophenoxy)-6-nitro-2-(trifluoromethyl)phenyl]pyrrolidin-2-yl}methyl acetate (170 mg).

Preparation Example 73

To a mixture of 2-{[(3R)-1-(2,4-difluoro-6-nitro-3-phenoxyphenyl)piperidin-3-yl]methyl}-1H-isoindol-1,3 (2H)-dione (0.376 g) and MeOH (5 mL) was added hydrazine monohydrate (110 μL), and the reaction mixture was stirred at reflux for 3 hours. The reaction mixture was cooled to room temperature, then poured into a 5% sodium hydroxide aqueous solution, and the resulting mixture was extracted with chloroform. The organic layer was separated, the aqueous layer was extracted with chloroform, and the combined organic layers were dried over Na$_2$SO$_4$, and concentrated under reduced pressure to give 1-[(3S)-1-(2,4-difluoro-6-nitro-3-phenoxyphenyl)piperidin-3-yl]methaneamine (0.266 g).

Preparation Example 75

To a mixture of 1-[(3S)-1-(2,4-difluoro-6-nitro-3-phenoxyphenyl)piperidin-3-yl]methaneamine (0.266 g), $CH_2Cl_2$ (5 mL) and TEA (153 μL) was added di-tert-butyl dicarbonate (202 μL), and the reaction mixture was stirred at room temperature for 63 hours. The reaction mixture was poured into water, and the resulting mixture was extracted with $CH_2Cl_2$. The organic layer was dried over MgSO$_4$, and concentrated under reduced pressure. The residue was purified by silica gel column chromatography (Hex/EtOAc) to give tert-butyl {[(3S)-1-(2,4-difluoro-6-nitro-3-phenoxyphenyl)piperidin-3-yl]methyl}carbamate (0.294 g).

Preparation Example 77

To a mixture of tert-butyl ({(3S)-1-[6-nitro-3-phenoxy-2-(trifluoromethyl)phenyl]piperidin-3-yl}methyl)carbamate (4.85 g), 1,4-dioxane (150 mL) and water (30 mL) were added zinc powder (6.4 g) and NH$_4$Cl (5.24 g) under ice cooling. The reaction mixture was stirred at room temperature for 3 hours, and insoluble substances were then separated by filtration through celite. The resulting filtrate was concentrated under reduced pressure, a saturated NaHCO$_3$ aqueous solution was then added to the residue, and the resulting mixture was extracted with chloroform. The extract was dried over MgSO$_4$, and then concentrated under reduced pressure to give tert-butyl ({(3S)-1-[6-amino-3-phenoxy-2-(trifluoromethyl)phenyl]piperidin-3-yl}methyl)carbamate (4.56 g).

Preparation Example 122

To a mixture of tert-butyl (2R)-2-{[(benzyloxy)amino]methyl}-4-[6-nitro-3-phenoxy-2-(trifluoromethyl)phenyl]piperazine-1-carboxylate (424 mg), EtOAc (2 mL) and ethanol (2 mL) was added Hydrous 10% palladium hydroxide-carrying carbon (100 mg) under a nitrogen atmosphere, which was then replaced by a hydrogen atmosphere, and the reaction mixture was stirred at room temperature for 2 hours. After replacement by a nitrogen atmosphere, the reaction mixture was then diluted with EtOAc, and filtered through celite, and the filtrate was concentrated under reduced pressure to give tert-butyl (2S)-2-(aminomethyl)-4-[6-amino-3-phenoxy-2-(trifluoromethyl)phenyl]piperazine-1-carboxylate (347 mg).

Preparation Example 123

To a mixture of tert-butyl (2S)-2-(aminomethyl)-4-[6-amino-3-phenoxy-2-(trifluoromethyl)phenyl]piperazine-1-carboxylate (345 mg) and methanol (2 mL) was added Ethyl trifluoroacetate (110 μL), and the reaction mixture was stirred overnight at room temperature. The reaction mixture was concentrated under reduced pressure to give tert-butyl (2S)-4-[6-amino-3-phenoxy-2-(trifluoromethyl)phenyl]-2-[(2,2,2-trifluoroacetamide)methyl]piperazine-1-carboxylate (380 mg).

Preparation Example 124

To a mixture of tert-butyl ({(3S)-1-[6-amino-3-phenoxy-2-(trifluoromethyl)phenyl]piperidin-3-yl}methyl)carbamate (4.56 g) and DMF (50 mL) were added 2-(Pyridazin-4-yl)-1,3-thiazole-4-carboxylic acid (2.23 g), DIPEA (3 mL) and HATU (4.5 g), and the resulting mixture was stirred overnight at 50° C. The reaction mixture was cooled to room temperature, water was then added to the reaction mixture under ice cooling, and the precipitated solid substance was taken by filtration. The resulting solid substance was dissolved in chloroform, water was added, and the resulting mixture was extracted with chloroform. The extract was dried over MgSO$_4$, and then concentrated under reduced pressure, and the residue was purified by silica gel column chromatography (Hex/EtOAc) to give tert-butyl {[(3S)-1-{3-phenoxy-6-[2-(pyridazin-4-yl)-1,3-thiazole-4-carboxamide]-2-(trifluoromethyl)phenyl}piperidin-3-yl]methyl}carbamate (5.85 g) as a solid.

Preparation Example 172

To a mixture of {(2R)-1-[3-(2-fluorophenoxy)-6-{[2-(pyridazin-4-yl)-1,3-thiazole-4-carbonyl]amino}-2-(trifluoromethyl) phenyl]pyrrolidin-2-yl}methyl acetate (194 mg) and methanol (1 mL) were water (0.1 mL) and K$_2$CO$_3$ (135 mg), and the reaction mixture was stirred overnight at room temperature. The reaction mixture was diluted with EtOAc, and then filtered through celite, and the filtrate was concentrated under reduced pressure to give N-[4-(2-fluorophenox)-2-[(2R)-2-(hydroxymethyl)pyrrolidin-1-yl]-3-(trifluoromethyl)phenyl]-2-(pyridazin-4-yl)-1,3-thiazole-4-carboxamide (200 mg).

Preparation Example 173

To a mixture of N-[4-(2-fluorophenoxy)-2-[(2R)-2-(hydroxymethyl)pyrrolidin-1-yl]-3-(trifluoromethyl)phenyl]-2-(pyridazin-4-yl)-1,3-thiazole-4-carboxamide (198 mg) and CH$_2$Cl$_2$ (2 mL) was added Dess-Martin reagent (220 mg) under ice cooling, and the reaction mixture was stirred at room temperature for 1 hour. Under ice cooling, 10% sodium sulfite aqueous solution and a saturated NaHCO$_3$ aqueous solution were added, and the resulting mixture was stirred at room temperature for 30 minutes. The reaction mixture was extracted using ISOLUTE (registered trademark) Phase Separator, and the extract was concentrated under reduced pressure. The residue was purified by silica gel chromatography (chloroform/methanol) to give N-[4-(2-fluorophenoxy)-2-[(2R)-2-formylpyrrolidin-1-yl]-3-(trifluoromethyl)phenyl]-2-(pyridazin-4-yl)-1,3-thiazole-4-carboxamide (112 mg).

Preparation Example 174

To a mixture of tert-butyl ({(3S)-1-[3-hydroxy-6-{[2-(pyridazin-4-yl)-1,3-thiazole-4-carbonyl]amino}-2-(trifluoromethyl) phenyl]piperidin-3-yl}methyl)carbamate (0.075 g), CH$_2$Cl$_2$ (4.5 mL) and pyridine (50 μL) was added Trifluoromethanesulfonic anhydride (52 μL) under ice cooling, and the reaction mixture was stirred at room temperature for 8 hours. The reaction mixture was poured into water, and the resulting mixture was extracted with CH$_2$Cl$_2$. The organic layer was washed with 10% hydrochloric acid, water and brine, then dried over Na$_2$SO$_4$, and concentrated under reduced pressure. To a mixture of the residue and pyridine (2.6 mL) was added Trifluoromethanesulfonic anhydride (64 μL) under ice cooling, and the reaction mixture was stirred at room temperature for 13 hours. The reaction mixture was poured into water, and the resulting mixture was extracted with EtOAc. The organic layer was washed with 10% hydrochloric acid, water and brine, then dried over Na$_2$SO$_4$, and concentrated under reduced pressure to give 3-[(3S)-3-{[(tert-butoxycarbonyl)amino]methyl}piperidin-1-yl]-4-{[2-(pyridazin-4-yl)-1,3-thiazole-4-carbonyl]amino}-2-(trifluoromethyl)phenyl trifluoromethanesulfonate (0.103 g).

Preparation Example 175

Under an argon atmosphere, to a mixture of K$_2$CO$_3$ (0.030 g), phenylboronic acid (0.027 g) and Pd (PPh$_3$)$_4$ (0.017 g) was added a mixture of 3-[(3S)-3-{[(tert-butoxycarbonyl)amino]methyl}piperidin-1-yl]-4-{[2-(pyridazin-4-yl)-1,3-thiazole-4-carbonyl]amino}-2-(trifluoromethyl)phenyl trifluoromethanesulfonate (0.103 g) and THF (2.5 mL), water (0.5 mL) was then added, and the reaction mixture was stirred at 110 to 130° C. for 8 hours. The reaction mixture was cooled to room temperature, and then poured into water, and the resulting mixture was extracted with EtOAc. The organic layer was washed with brine, then dried over Na$_2$SO$_4$, and concentrated under reduced pressure. The residue was purified by silica gel column chromatography (Hex/EtOAc) to give tert-butyl ({(3S)-1-[4-{[2-(pyridazin-4-yl)-1,3-thiazole-4-carbonyl]amino}-2-(trifluoromethyl)[1,1'-biphenyl]-3-yl]piperidin-3-yl}methyl)carbamate (0.067 g).

Preparation Example 176

To a mixture of tert-butyl 4-[3-phenoxy-6-{[2-(pyridazin-4-yl)-1,3-thiazole-4-carbonyl]amino}-2-(trifluoromethyl)phenyl]-3,6-dihydropyridine-1 (2H)-carboxylate (2.4 g) and methanol (24 mL) was added 4 M HCl/1,4-dioxane solution (10 mL), and the reaction mixture was stirred at room temperature for 19 hours. The reaction mixture was concentrated under reduced pressure, a saturated NaHCO$_3$ aqueous solution was added to the residue, and the resulting mixture was extracted with a mixed solvent (chloroform/methanol). The organic layer was dried over MgSO$_4$, and concentrated under reduced pressure. The residue was purified by silica gel column chromatography (chloroform/methanol) to give N-[4-phenoxy-2-(1,2,3,6-tetrahydropyridin-4-yl)-3-(trifluoromethyl)phenyl]-2-(pyridazin-4-yl)-1,3-thiazole-4-carboxamide (1.57 g) as a solid.

Preparation Example 182

To a mixture of N-{2-[(3R)-3-(aminomethyl)piperidin-1-yl]-4-phenoxy-3-(trifluoromethyl)phenyl}-2-(pyridazin-4-yl)-1,3-thiazole-4-carboxamide (63 mg) and CH$_2$Cl$_2$ (1 mL) were added DIPEA (30 μL) and 2-nitrobenzenesulfonyl chloride (30 mg) under ice cooling, and the reaction mixture was stirred for 1 hour under ice cooling. A saturated NH$_4$Cl aqueous solution was added, the resulting mixture was extracted using ISOLUTE (registered trademark) Phase Separator, and the extract was concentrated under reduced pressure. The residue was purified by silica gel column chromatography (chloroform/methanol) to give N-{2-[(3S)-3-{[(2-nitrobenzene-1-sulfonyl)amino]methyl}piperidin-1-yl]-4-phenoxy-3-(trifluoromethyl) phenyl}-2-(pyridazin-4-yl)-1,3-thiazole-4-carboxamide (94 mg).

Preparation Example 185

To a mixture of N-{2-[(3S)-3-{[(2-nitrobenzene-1-sulfonyl)amino]methyl}piperidin-1-yl]-4-phenoxy-3-(trifluoromethyl) phenyl}-2-(pyridazin-4-yl)-1,3-thiazole-4-carboxamide (90 mg) and MeCN (1 mL) were added Methyl iodide (25 μL) and cesium carbonate (45 mg) at room temperature, and the reaction mixture was stirred at room temperature for 30 minutes. EtOAc was added, the resulting mixture was filtered through celite, and the filtrate was then concentrated under reduced pressure to give N-{2-[(3S)-3-{[methyl(2-nitrobenzene-1-sulfonyl)amino]methyl} piperidin-1-yl]-4-phenoxy-3-(trifluoromethyl)phenyl}-2-(pyridazin-4-yl)-1,3-thiazole-4-carboxamide (83 mg).

Preparation Example 190

To a mixture of N-{2-[(3R)-3-{[methyl(trifluoroacetyl)amino]methyl}piperazin-1-yl]-4-phenoxy-3-(trifluoro methyl)phenyl}-2-(pyridazin-4-yl)-1,3-thiazole-4-carboxamide (40 mg) and CH$_2$Cl$_2$ (1 mL) were added 35% formaldehyde aqueous solution (10 μL), acetic acid (5 μL) and NaBH(OAc)$_3$ (20 mg), and the reaction mixture was stirred overnight at room temperature. A saturated NaHCO$_3$ aqueous solution was added to the reaction mixture, the resulting mixture was stirred for 10 minutes, and extracted using ISOLUTE (registered trademark) Phase Separator, and the extract was concentrated under reduced pressure. The residue was purified by silica gel column chromatography (Hex/EtOAc aminnosilica gel) to give N-{2-[(3R)-4-methyl-3-{[methyl(trifluoroacetyl)amino]methyl} piperazin-1-yl]-4-phenoxy-3-(trifluoromethyl)phenyl}-2-(pyridazin-4-yl)-1,3-thiazole-4-carboxamide (36 mg).

Preparation Example 192

To a mixture of sodium hydride (60% oil dispersion, 0.208 mg) and THF (5 mL), was added thiophenol (0.38 g) at −78° C., and the reaction mixture was stirred at −78° C. for 15 minutes. 2-bromo-4-fluoro-1-nitro-3-(trifluoromethyl)benzene (1.00 g) was added, and the reaction mixture was stirred at −78° C. for 15 minutes. A saturated NH$_4$Cl aqueous solution was added, the resulting mixture was extracted three times with EtOAc. The combined organic layer was dried over Na$_2$SO$_4$, and concentrated under reduced pressure. The residue was purified by silica gel column chromatography (Hex/EtOAc) to give 2-bromo-1-nitro-4-(phenylsulfanyl)-3-(trifluoromethyl)benzene (0.50 g).

Preparation Example 193

Under an argon atmosphere, to a mixture of 1,3-difluoro-2-(methanesulphonyl)benzene (1.60 g) and concentrated sulfuric acid (12 mL) was added potassium nitrate (0.84 g) under ice cooling, and the reaction mixture was stirred at room temperature for 2 hours. The reaction mixture was poured into ice water, and the precipitated solid was taken by filtration. The obtained solid was dissolved in EtOAc, washed with a saturated NaHCO$_3$ aqueous solution, and dried over Na$_2$SO$_4$. The residue was concentrated under reduced pressure to give 1,3-difluoro-2-(methanesulphonyl)-4-nitrobenzene (1.80 g) as a solid.

Preparation Example 194

To a mixture of 4-amino-3-fluoro-2-(trifluoromethyl) benzoate (1.30 g) and THF (15 mL) was added dropwise 30% hydrogen peroxide solution (5 mL) under ice cooling, and the reaction mixture was stirred at room temperature for 5 minutes and at 80° C. for 2 hours. The reaction mixture was cooled to room temperature, then poured into ice water, and the resulting mixture was extracted twice with EtOAc. The combined organic layers were washed with water, and dried over Na$_2$SO$_4$. The residue was concentrated under reduced pressure to give 3-fluoro-4-nitro-2-(trifluoromethyl) benzoate (1.20 g) as a solid.

Preparation Example 195

To a mixture of 3-fluoro-4-nitro-2-(trifluoromethyl) benzoic acid (1.20 g) and CH$_2$Cl$_2$ (30 mL) was added dropwise oxalyl chloride (2.03 mL) under ice cooling, and a catalytic amount of DMF was added. The reaction mixture was stirred for 1 hour under ice cooling, and then concentrated under reduced pressure. The residue was dissolved in benzene (15 mL), and aluminum chloride (1.26 g) was added for at least 5 minutes and stirred at room temperature for 1 hour. The reaction mixture was poured on an ice and extracted three times with EtOAc. The combined organic layers were dried over Na$_2$SO$_4$, and then concentrated under reduced pressure. The residue was purified by silica gel column chromatography (Hex/EtOAc) to give [3-fluoro-4-nitro-2-(trifluoromethyl)phenyl](phenyl)methanone (0.80 g) as a solid.

Preparation Example 196

To a mixture of (8S)-8-hydroxyhexahydropyrrolo[1,2-a]pyrazine-1,4-dione (3.250 g), DMF (48 mL) and imidazole (3.972 g) was added tert-butyl chlorodiphenyl silane (10.0 mL), and the reaction mixture was stirred at room temperature for 23 hours. The reaction mixture was poured into water and extracted with EtOAc. The organic layer was washed with water and brine, dried over Na$_2$SO$_4$, and then, concentrated under reduced pressure. The residue was purified by silica gel column chromatography (EtOAc/MeOH)

to give (8S,8aS)-8-{[tert-butyldi(phenyl)silyl] oxy}hexahydropyrrolo[1,2-a]pyrazine-1,4-dione (1.786 g) as a less polar substance and (8S,8aR)-8-{[tert-butyldi(phenyl)silyl]oxy}hexahydropyrrolo[1,2-a]pyrazine-1,4-dione (1.164 g) as a more polar substance.

Preparation Example 197

To a mixture of lithium aluminum hydride (0.594 g) and THF (40 mL) was added THF (10 mL) solution of (8S,8aR)-8-{[tert-butyldi(phenyl)silyl]oxy}hexahydropyrrolo[1,2-a]pyrazine-1,4-dione (1.164 g), and the reaction mixture was stirred at reflux by heating for 17 hours. The reaction suspension was cooled to room temperature, and a mixture of water (0.7 mL) and THF (7.7 mL) and 4N aqueous sodium hydroxide (0.7 mL) were added. To the resulting mixture was added $Na_2SO_4$ and the mixture was stirred at room temperature for 3 hours, and filtered through celite. The filtrate was concentrated under reduced pressure to give (8S,8aS)-octahydropyrrolo[1,2-a]pyrazine-8-ol (0.972 g).

Preparation Example 216

Under an argon atmosphere, to a mixture of (8S,8aS)-2-[6-nitro-3-phenoxy-2-(trifluoromethyl)phenyl]octahydropyrrolo[1,2-a]pyrazine-8-ol (0.375 g), THF (6 mL), benzoic acid (0.119 g) and triphenylphosphine (0.349 g) was added diisopropyl azodicarboxylate (262 µL) under ice cooling. The reaction mixture was allowed to slowly warm to room temperature and was stirred for 15 hours. The reaction mixture was concentrated under reduced pressure, and the residue was purified by silica gel column chromatography (Hex/EtOAc) to give benzoic acid (8R,8aS)-2-[6-nitro-3-phenoxy-2-(trifluoromethyl)phenyl]octahydropyrrolo[1,2-a]pyrazine-8-yl (0.518 g).

Preparation Example 220

Under an argon atmosphere, to a mixture of tert-butyl {[(3S)-1-(2-bromo-6-nitro-3-phenoxyphenyl)piperidin-3-yl]methyl}carbamate (550 mg), cyclopropyl boronic acid (112 mg), tricyclohexylphosphine (30 mg), toluene (9 mL) and water (1 mL) was added palladium acetate (24 mg), and the reaction mixture was stirred at 110° C. for 4 hours under microwave irradiation. The reaction mixture was concentrated under reduced pressure, and the residue was purified by silica gel column chromatography (Hex/EtOAc) to give tert-butyl {[(3S)-1-(2-cyclopropyl-6-nitro-3-phenoxyphenyl)piperidin-3-yl]methyl}carbamate (280 mg).

Preparation Example 221

Under an argon atmosphere, to a mixture of (8S,8aS)-2-[6-nitro-3-phenoxy-2-(trifluoromethyl)phenyl]octahydropyrrolo[1,2-a]pyrazine-8-ol (0.233 g), THF (4 mL), phthalimide (0.090 g) and triphenylphosphine (0.173 g) was added diisopropyl azodicarboxylate (0.13 mL) under ice cooling, and the reaction mixture was allowed to slowly warm to room temperature and stirred for 15 hours. Triphenylphosphine (0.173 g) and diisopropyl azodicarboxylate (0.13 mL) were added to the reaction mixture under ice cooling, and then allowed to slowly warm to room temperature and stirred for 8 hours. The reaction mixture was concentrated under reduced pressure, and the residue was purified by silica gel column chromatography (Hex/EtOAc) to give 2-{(8R,8aS)-2-[6-nitro-3-phenoxy-2-(trifluoromethyl)phenyl]octahydropyrrolo[1,2-a]pyrazin e-8-yl}-1H-isoindole-1,3(2H)-dione (0.214 g).

Preparation Example 271

To a mixture of tert-butyl {[(3S)-1-{6-[(2-bromo-1,3-thiazole-4-carbonyl)amino]-3-(phenylsulfanyl)-2-(trifluoromethyl)phenyl}piperidin-3-yl]methyl}carbamate (300 mg) and $CH_2Cl_2$ (5 mL) was added m-chloroperbenzoic acid (water content: 40%, 385 mg) under ice cooling, and the reaction mixture was stirred at room temperature for 12 hours. The reaction was quenched with a saturated aqueous solution of sodium thiosulfate and was extracted twice with $CH_2Cl_2$. The combined organic layer was dried over $Na_2SO_4$, and then, concentrated under reduced pressure. The residue was purified by silica gel column chromatography (Hex/EtOAc) to give tert-butyl ({(3S)-1-[3-(benzene sulfonyl)-6-[(2-bromo-1,3-thiazole-4-carbonyl)amino]-2-(trifluoromethyl)phenyl]piperidin-3-yl}methyl)carbamate (200 mg).

Preparation Example 272

Under an argon atmosphere, to a mixture of tert-butyl ({(3S)-1-[3-(benzenesulfonyl)-6-[(2-bromo-1,3-thiazole-4-carbonyl)amino]-2-(trifluoromethyl) phenyl]piperidin-3-yl}methyl)carbamate (200 mg), 4-(tributylstannyl) pyridazine (115 mg) and toluene (10 mL) was added $Pd(PPh_3)_4$ (33 mg), and the reaction mixture was stirred at 100° C. for 24 hours. The reaction mixture was cooled to room temperature, and then, concentrated under reduced pressure. The residue was purified by silica gel column chromatography (Hex/EtOAc) to give tert-butyl ({(3S)-1-[3-(benzenesulfonyl)-6-{[2-(pyridazine-4-yl)-1,3-thiazole-4-carbonyl]amino}-2-(trifluoromethyl) phenyl]piperidin-3-yl}methyl)carbamate (100 mg).

The compounds shown in Tables 5-1 to 5-35 below were prepared in the same manner as in the production methods of Production Examples described above. Tables 5-1 to 5-35 below show the structures of the compounds of Production Examples, and Tables 6-1 to 6-12 show the methods for preparing the compounds of Production Examples and physiochemical data. These compounds can be easily prepared by using the production methods of Production Examples above, methods obvious to those skilled in the art, or modified methods thereof.

Example 1

To a mixture of N-[2-(1-oxa-4,9-diazaspiro[5.5]undecan-4-yl)-4-phenoxy-3-(trifluoromethyl)phenyl]-2-(pyridazin-4-yl)-1,3-thiazole-4-carboxamide (93 mg) and $CH_2Cl_2$ (1 mL) were added 35% formamide aqueous solution (50 µL), acetic acid (40 µL) and NaBH (OAc)$_3$ (100 mg), and the reaction mixture was stirred at room temperature for 1 hour. A saturated $NaHCO_3$ aqueous solution was added to the reaction mixture, the resulting mixture was stirred for 10 minutes, and extracted using ISOLUTE (registered trademark) Phase Separator, and the extract was concentrated under reduced pressure. The residue was purified by silica gel column chromatography (chloroform/methanol) to give an oily substance. The oily substance was solidified with MeCN, taken by filtration, and then dried under reduced pressure to give N-[2-(9-methyl-1-oxa-4,9-diazaspiro[5.5]

undecan-4-yl)-4-phenoxy-3-(trifluoromethyl)phenyl]-2-(pyridazin-4-yl)-1,3-thiazole-4-carboxamide (72 mg) as a solid.

Example 6

To a mixture of N-{2-[(3R)-4-methyl-3-{[methyl(trifluoroacetyl)amino]methyl}piperazin-1-yl]-4-phenoxy-3-(trifluoromethyl)phenyl}-2-(pyridazin-4-yl)-1,3-thiazole-4-carboxamide (35 mg) and methanol (0.5 mL) were added $K_2CO_3$ (15 mg) and water (0.1 mL), and the reaction mixture was stirred at room temperature for 1.5 hours. The reaction mixture was diluted with EtOAc, and filtered through celite, and the filtrate was then concentrated under reduced pressure. The residue was purified by silica gel column chromatography (chloroform/methanol/aqueous ammonia). The resulting crude product was solidified with diethyl ether, and the resulting solid substance was taken by filtration, and dried at 50° C. under reduced pressure to give N-[2-{(3S)-4-methyl-3-[(methylamino)methyl]piperazin-1-yl}-4-phenoxy-3-(trifluoromethyl)phenyl]-2-(pyridazin-4-yl)-1,3-thiazole-4-carboxamide (17 mg) as a solid.

Example 9

To a mixture of tert-butyl {[(3S)-1-3-phenoxy-6-[2-(pyridazin-4-yl)-1,3-thiazole-4-carboxamide]-2-(trifluoromethyl)phenyl}piperidin-3-yl]methyl}carbamate (5.83 g) and $CH_2Cl_2$ (60 mL) was added TFA (7 mL) under ice cooling, and the reaction mixture was stirred overnight at room temperature. The reaction mixture was concentrated under reduced pressure, diluted with $CH_2Cl_2$, and then neutralized by addition of a saturated $NaHCO_3$ aqueous solution under ice cooling. The resulting mixture was extracted with chloroform, and the extract was then dried over $MgSO_4$, and concentrated under reduced pressure. The residue was purified by silica gel column chromatography (chloroform/methanol/aqueous ammonia). The resulting solid substance was washed with diethyl ether to give N-{2-[(3S)-3-(aminomethyl)piperidin-1-yl]-4-phenoxy-3-(trifluoromethyl)phenyl}-2-(pyridazin-4-yl)-1,3-thiazole-4-carboxamide (3.52 g) as a solid.

Example 49

To a mixture of N-{2-[(3R)-3-{[methyl(2-nitrobenzene-1-sulfonyl)amino]methyl}piperidin-1-yl]-4-phenoxy-3-(trifluoromethyl)phenyl}-2-(pyridazin-4-yl)-1,3-thiazole-4-carboxamide (202 mg) and DMF (1 mL) were thioglycolic acid (60 μL) and lithium hydroxide monohydrate (60 mg), and the reaction mixture was stirred at 70° C. for 15 minutes. The reaction mixture was cooled to room temperature, $CH_2Cl_2$ and a saturated $NaHCO_3$ aqueous solution were then added to the reaction mixture, the resulting mixture was stirred, and extracted using ISOLUTE (registered trademark) Phase Separator, and the extract was concentrated under reduced pressure. The residue was purified by silica gel chromatography (EtOAc/chloroform) to give an oily substance. The oily substance was solidified with MeCN, taken by filtration, and then dried under reduced pressure to give N-[2-{(3S)-3-[(methylamino)methyl]piperidin-1-yl}-4-phenoxy-3-(trifluoromethyl)phenyl]-2-(pyridazin-4-yl)-1,3-thiazole-4-carboxamide (29 mg) as a solid.

Example 54

To a mixture of N-{2-[(3R)-3-(aminomethyl)piperidin-1-yl]-4-phenoxy-3-(trifluoromethyl)phenyl}-2-(pyridazin-4-yl)-1,3-thiazole-4-carboxamide (83 mg) and $CH_2Cl_2$ (1 mL) were added 35% formaldehyde aqueous solution (50 μL), acetic acid (35 μL) and $NaBH(OAc)_3$ (100 mg), and the reaction mixture was stirred at room temperature for 1 hour. A saturated $NaHCO_3$ aqueous solution was added, the resulting mixture was stirred at room temperature for 10 minutes, and extracted using ISOLUTE (registered trademark) Phase separator, and the extract was concentrated under reduced pressure. The residue was purified by silica gel chromatography (chloroform/methanol), the resulting substance was dissolved in EtOAc, a 4 M HCl/EtOAc solution (120 μL) was then added, and the precipitated solid substance was taken by filtration, and dried at 50° C. under reduced pressure to give N-[2-{(3R)-3-[(dimethylamino)methyl]piperidin-1-yl}-4-phenoxy-3-(trifluoromethyl)phenyl]-2-(pyridazin-4-yl)-1,3-thiazole-4-carboxamide dihydrochloride (71 mg) as a solid.

Example 59

To a mixture of N-[2-(1-oxa-4,9-diazaspiro[5.5]undecan-4-yl)-4-phenoxy-3-(trifluoromethyl)phenyl]-2-(pyridazin-4-yl)-1,3-thiazole-4-carboxamide (100 mg) and MeCN (1 mL) were added DIPEA (35 μL) and 1-bromo-2-methoxyethane (20 μL), and the reaction mixture was stirred at 100° C. for 1 hour under microwave irradiation. The reaction mixture was cooled to room temperature, and then concentrated under reduced pressure. The residue was purified by silica gel column chromatography (chloroform/methanol), and diluted with EtOAc, 4 M HCl/1,4-dioxane solution (130 μL) was added at room temperature, and the resulting mixture was stirred at room temperature for 10 minutes. The precipitated solid was taken by filtration, and dried under reduced pressure to give N-{2-[9-(2-methoxyethyl)-1-oxa-4,9-diazaspiro[5.5]undecan-4-yl]-4-phenoxy-3-(trifluoromethyl) phenyl}-2-(pyridazin-4-yl)-1,3-thiazole-4-carboxamide dihydrochloride (67 mg) as a solid.

Example 62

To a mixture of N-[2-(1-oxa-4,9-diazaspiro[5.5]undecan-4-yl)-4-phenoxy-3-(trifluoromethyl)phenyl]-2-(pyridazin-4-yl)-1,3-thiazole-4-carboxamide (150 mg) and $CH_2Cl_2$ (1 mL) were added 3-oxetanone (60 mg), acetic acid (45 μL) and $NaBH(OAc)_3$ (160 mg) at room temperature, and the reaction mixture was stirred overnight. A saturated $NaHCO_3$ aqueous solution was added, the resulting mixture was stirred at room temperature for 30 minutes, and extracted using ISOLUTE (registered trademark) Phase separator, and the extract was concentrated under reduced pressure. The residue was purified by silica gel column chromatography (chloroform/methanol) to give an oily substance. The oily substance was solidified with EtOAc, Hex and diisopropyl ether, taken by filtration, and then dried under reduced pressure to give N-{2-[9-(oxetan-3-yl)-1-oxa-4,9-diazaspiro [5.5]undecan-4-yl]-4-phenoxy-3-(trifluoromethyl) phenyl}-2-(pyridazin-4-yl)-1,3-thiazole-4-carboxamide (99 mg) as a solid.

Example 63

To a mixture of N-[4-(2-fluorophenoxy)-2-[(2R)-2-formylpyrrolidin-1-yl]-3-(trifluoromethyl)phenyl]-2-(pyridazin-4-yl)-1,3-thiazole-4-carboxamide (60 mg) and $CH_2Cl_2$ (0.5 mL) were added 3-oxetanamine (25 mg), acetic acid (20 μL) and $NaBH(OAc)_3$ (70 mg), and the reaction mixture was stirred at room temperature for 2 hours. A saturated $NaHCO_3$ aqueous solution was added, the resulting mixture was stirred at room temperature for 30 minutes, and extracted using ISOLUTE (registered trademark) Phase separator, and the extract was concentrated under reduced pressure. The residue was purified by silica gel chromatography (chloroform/methanol) to give an oily substance. Diethyl ether was added to the resulting oily substance, and the resulting mixture was concentrated under reduced pressure to give N-[4-(2-fluorophenoxy)-2-[(2R)-2-{[(oxetan-3-yl)amino]methyl}pyrrolidin-1-yl]-3-(trifluoromethyl) phenyl]-2-(pyridazin-4-yl)-1,3-thiazole-4-carboxamide (20 mg) as a solid.

Example 64

A mixture of 2-bromo-1-nitro-4-phenoxy-3-(trifluoromethyl)benzene (10.9 mg), tert-butyl, methyl[(piperidin-3-yl)methyl]carbamate (20.7 mg), DIPEA (20 μL) and NMP (250 μL) was stirred overnight at 120° C. The reaction mixture was cooled, PS-Isocyanate (150 mg) and chloroform (1 mL) were then added thereto, and the reaction mixture was stirred overnight. Thereafter, insoluble substances were separated by filtration, and the filtrate was concentrated under reduced pressure. To the resulting residue were added ethanol (0.8 mL), water (0.2 mL), $NH_4Cl$ (0.8 mg) and reduced iron (10 mg). The reaction mixture was stirred overnight at 80° C. The reaction mixture was cooled to room temperature, water and chloroform were added thereto, a liquid separation process was carried out, and the resulting organic layer was concentrated under reduced pressure. To the resulting residue were added 2-(Pyridazin-4-yl)-1,3-thiazole-4-carboxylic acid (6.2 mg), DIPEA (10 μL) and DMF (185 μL), a solution of HATU (13.3 mg) in DMF (200 μL) was then added, and the reaction mixture was stirred overnight at room temperature. Separation and purification was performed with HPLC (column: SunFire (registered trademark) (MeOH/0.1% HCOOH—$H_2O$), TFA (500 μL) was added to the resulting residue, and the resulting mixture was stirred for 1 hour. The reaction mixture was concentrated under reduced pressure, a saturated $NaHCO_3$ aqueous solution and chloroform were added, a liquid separation process was carried out, and the resulting organic layer was concentrated under reduced pressure to give N-[2-{3-[(methylamino)methyl]piperidin-1-yl}-4-phenoxy-3-(trifluoromethyl)phenyl]-2-(pyridazin-4-yl)-1,3-thiazole-4-carboxamide (3.8 mg).

Example 78

To a mixture of N-{2-[(8R,8aS)-8-(1,3-dioxo-1,3-dihydro-2H-isoindol-2-yl)hexahydropyrrolo[1,2-a]pyrazine-2(1H)-yl]-4-phenoxy-3-(trifluoromethyl)phenyl}-2-(pyridazin-4-yl)-1,3-thiazole-4-carboxamide (0.097 g) and MeOH (1.4 mL) was added hydrazine monohydrate (19.8 μL), and the reaction mixture was stirred at reflux for 6 hours. The reaction mixture was cooled to room temperature, then poured into a 5% sodium hydroxide aqueous solution, and the resulting mixture was extracted with $CH_2Cl_2$. The organic layer was separated, the aqueous layer was extracted with $CH_2Cl_2$, and the combined organic layer was dried over $MgSO_4$, and concentrated under reduced pressure. The residue was purified by silica gel column chromatography ($CH_2Cl_2$/MeOH) to give N-{2-[(8R,8aS)-8-aminohexahydropyrrolo[1,2-a]pyrazine-2(1H)-yl]-4-phenoxy-3-(trifluoro methyl)phenyl}-2-(pyridazin-4-yl)-1,3-thiazole-4-carboxamide (0.047 g).

Example 83

To N-[4-(2-fluorophenoxy)-2-{(3S)-3-[(methylamino)methyl]piperidin-1-yl}-3-(trifluoromethyl) phenyl]-2-(pyridazin-4-yl)-1,3-thiazole-4-carboxamide monohydrochloride salt (200 mg) was added EtOAc and a saturated $NaHCO_3$ aqueous solution, and the reaction mixture was stirred for a while. The aqueous layer was separated, the aqueous layer was extracted with solvents combining EtOAc and MeOH, and the combined organic layer was washed with water and brine, dried over $Na_2SO_4$, and concentrated under reduced pressure. The residue was added with 2-propanol (4 mL) and stirred for a while at 80° C. To the mixture were added fumaric acid (40 mg) and water (200 μL) and stirred at room temperature for 24 hours. The precipitate was taken by filtration, and dried under reduced pressure to give N-[4-(2-fluorophenoxy)-2-{(3S)-3-[(methylamino)methyl]piperidin-1-yl}-3-(trifluoromethyl) phenyl]-2-(pyridazin-4-yl)-1,3-thiazole-4-carboxamide mono[(2E)-but-2-enedioate] (141 mg) as a crystal.

Example 84

To N-{2-[(3S)-3-(aminomethyl)piperidin-1-yl]-4-phenoxy-3-(trifluoromethyl)phenyl}-2-(pyridazin-4-yl)-1,3-thiazole-4-carboxamide (100 mg) was added ethanol (2 mL) and stirred at 75° C. to obtain a solution. To the solution, fumaric acid (23 mg) and water (400 μL) were added and stirred overnight at room temperature. The precipitate was taken by filtration, and dried under reduced pressure to give N-{2-[(3S)-3-(aminomethyl)piperidin-1-yl]-4-phenoxy-3-(trifluoromethyl)phenyl}-2-(pyridazin-4-yl)-1,3-thiazole-4-carboxamide mono[(2E)-but-2-enedioate] (73 mg) as a crystal.

The compounds shown in Tables 7-1 to 7-11 below were prepared in the same manner as in the preparation methods of Examples described above. Tables 7-1 to 7-11 below show the structures of the compounds of each Example, and Tables 8-1 to 8-5 show the methods for preparing the compounds of each Example and physiochemical data. These compounds can be easily prepared by using the preparation methods of Examples above, methods obvious to those skilled in the art, or modified methods thereof.

Table 9 below shows the structure and the physiochemical data of the compound of Reference Example. The compound can be easily prepared by using the preparation methods of Examples above or Preparation Examples, methods obvious to those skilled in the art, or modified methods thereof.

In the tables below, the following abbreviations may be used.
PEx: Number of Preparation Example
Ex: Number of Example
PSyn: Method for preparing compound of Preparation Example (the number of the PSyn field indicates that the compound concerned was prepared using the same method as that for a compound of Preparation Example whose number is identical to that of the PSyn field, and using corresponding raw materials; for example, the compound of a PSyn field whose number is 1 was prepared using the same method as that for the compound of Preparation Example 1)
Syn: Method for preparing compound of Example (the number of the Syn field indicates that the compound concerned was prepared using the same method as that for a compound of Example whose number is identical to that of the Syn field, and using corresponding raw materials; and for example, the compound of a Syn field whose number is 1 was prepared using the same method as that for the compound of Example 1)

Str: Chemical structural formula

DAT: Physiochemical data

ESI+: m/z value in mass analysis (ionization method ESI, [M+H]$^+$ or [M+Na]$^+$ unless otherwise specified)

ESI−: m/z value in mass analysis (ionization method ESI, [M−H]$^-$ unless otherwise specified) NMR DMSO-d6 (400 MHz) or NMR DMSO-d6 (500 MHz): S value of signal (ppm) in $^1$H-NMR in DMSO-d6

NMR CDCl$_3$ (400 MHz) or NMR CDCl$_3$ (500 MHz): δ value of signal (ppm) in $^1$H-NMR in CDCl$_3$ s: Single line (spectrum)

d: Double line (spectrum)

t: Triple line (spectrum)

m: Multiple line (spectrum)

br: Broad line (spectrum)

dd: Double double line (spectrum)

Unless otherwise specified, the compound is an optical isomer having an absolute steric conformation described in a chemical structural formula. In the structural formula, HCl indicates that the compound concerned is a monohydrochloride, 2HCl indicates that the compound concerned is a dihydrochloride, and 3HCl indicates that the compound concerned is a trihydrochloride.

TABLE 5-1

| PEx | Str |
|---|---|
| 1 | |
| 2 | 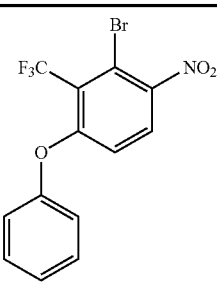 |
| 3 | 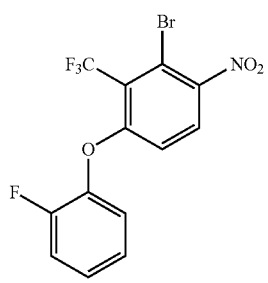 [SMILES: O=[N+]([O-])c1ccc(Oc2ccccc2F)c(C(F)(F)F)c1Br] |

TABLE 5-1-continued

| PEx | Str |
|---|---|
| 4 | 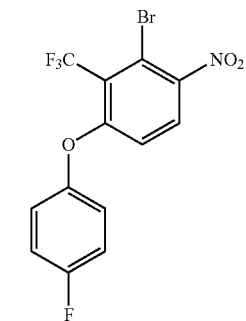 [SMILES: O=[N+]([O-])c1ccc(Oc2ccc(F)cc2)c(C(F)(F)F)c1Br] |
| 5 | 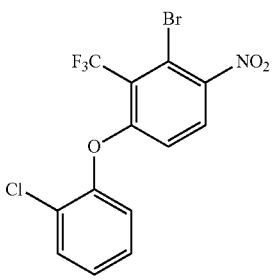 [SMILES: O=[N+]([O-])c1ccc(Oc2ccccc2Cl)c(C(F)(F)F)c1Br] |
| 6 | 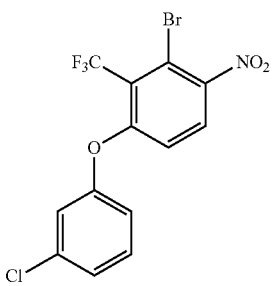 [SMILES: O=[N+]([O-])c1ccc(Oc2cccc(Cl)c2)c(C(F)(F)F)c1Br] |
| 7 | 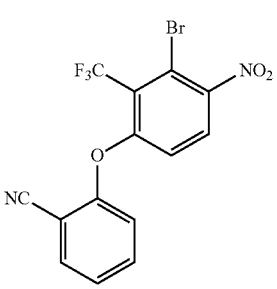 [SMILES: N#Cc1ccccc1Oc1ccc([N+](=O)[O-])c(Br)c1C(F)(F)F] |
| 8 | 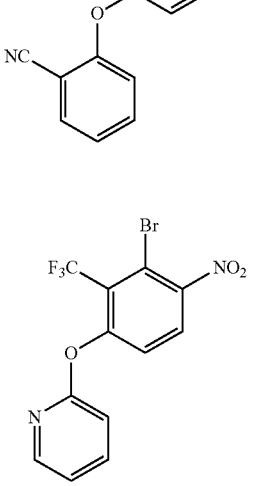 |

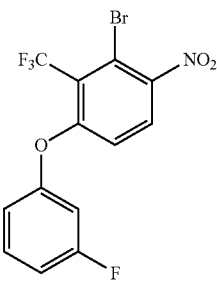

TABLE 5-2
| PEx | Str |
|---|---|
| 9 | 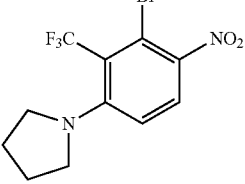 |
| 10 | 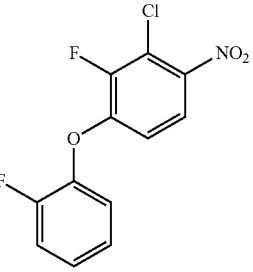 |
| 11 | 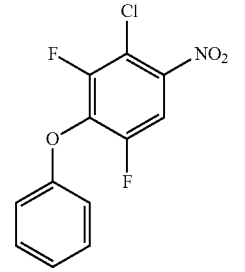 [SMILES: O=[N+]([O-])c1cc(F)c(Oc2ccccc2)c(F)c1Cl] |
| 12 | 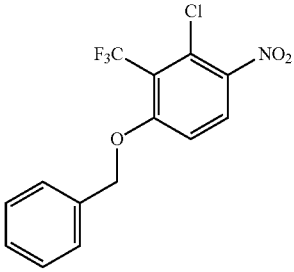 [SMILES: O=[N+]([O-])c1ccc(OCc2ccccc2)c(C(F)(F)F)c1Cl] |
| 13 | 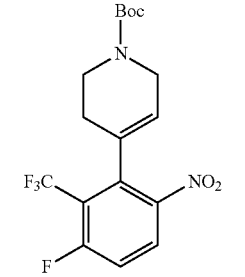 [SMILES: CC(C)(C)OC(=O)N1CC=C(c2c([N+](=O)[O-])ccc(F)c2C(F)(F)F)CC1] |
TABLE 5-2-continued
| PEx | Str |
|---|---|
| 14 | 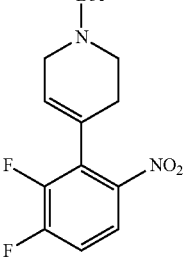 |
| 15 | 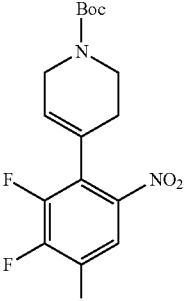 |
| 16 | 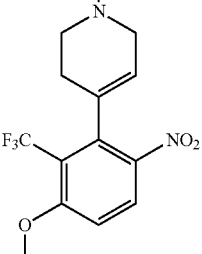 |
TABLE 5-3
| PEx | Str |
|---|---|
| 17 | 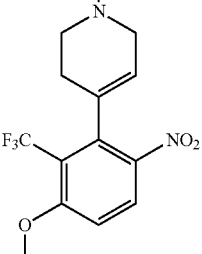 |

TABLE 5-3-continued

| PEx | Str |
|---|---|
| 18 | (Boc-tetrahydropyridinyl)-phenyl with F₃C, NO₂, and O-cyclopropyl substituents |
| 19 | cyclobutyloxy, F, NO₂-phenyl with N-Boc-tetrahydropyridinyl |
| 20 | N-Boc-tetrahydropyridinyl-phenyl with F, NO₂, and O-cyclopropyl substituents |
| 21 | (3-((Boc-amino)methyl)piperidin-1-yl)-phenyl with F₃C, NO₂, and O-cyclopropyl |
| 22 | (3-((Boc-amino)methyl)piperidin-1-yl)-phenyl with F₃C, NO₂, and O-cyclobutyl |
| 23 | (3-((Boc-amino)methyl)piperidin-1-yl)-phenyl with F₃C, NO₂, and O-cyclopentyl |
| 24 | (3-((Boc-amino)methyl)piperidin-1-yl)-phenyl with F₃C, NO₂, and O-(1-methyl-1H-pyrazol-4-yl) |

TABLE 5-4

| PEx | Str |
|---|---|
| 25 | (3-((Boc-amino)methyl)piperidin-1-yl)-phenyl with F₃C, NO₂, and O-(1-methyl-1H-pyrazol-3-yl) |

TABLE 5-4-continued
| PEx | Str |
|---|---|
| 26 | 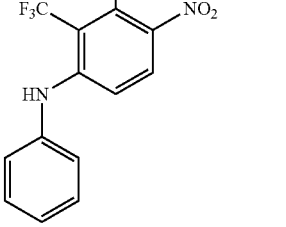 |
| 27 | 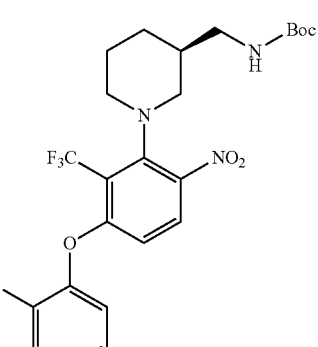 |
| 28 | 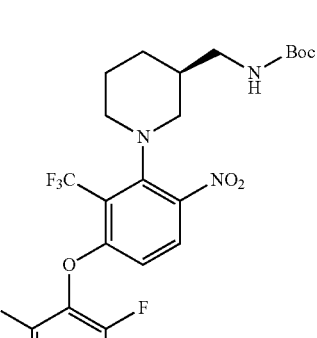 |
| 29 | 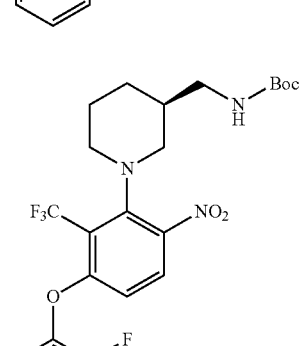 |
TABLE 5-4-continued
| PEx | Str |
|---|---|
| 30 | 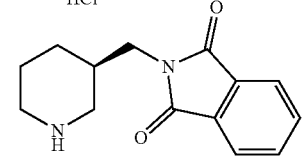 |
| 31 | 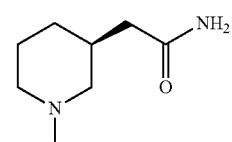 |
| 32 | 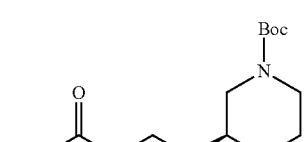 |
TABLE 5-5
| PEx | Str |
|---|---|
| 33 | 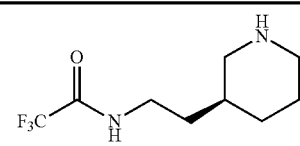 |
| 34 | 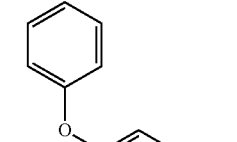 |
| 35 | 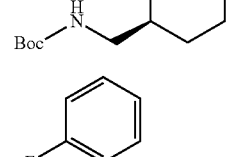 |

TABLE 5-5-continued

| PEx | Str |
|---|---|
| 36 | (3-fluorophenoxy group at position 3, CF3 at position 2, NO2 at position 6 of benzene; piperidin-1-yl at position 1 with (Boc-NH-CH2-) substituent at piperidine 3-position) |
| 37 | (piperidine N-substituted on benzene bearing CF3, NO2, and 4-fluorophenoxy; Boc-NH-CH2- on piperidine 3-position) |
| 38 | (2-chlorophenoxy analog; benzene with CF3 and NO2; N-piperidinyl with Boc-NH-CH2-) |

TABLE 5-5-continued

| PEx | Str |
|---|---|
| 39 | (3-chlorophenoxy analog; benzene with CF3 and NO2; N-piperidinyl with Boc-NH-CH2-) |
| 40 | (2-cyanophenoxy analog; benzene with CF3 and NO2; N-piperidinyl with Boc-NH-CH2-) |

TABLE 5-6

| PEx | Str |
|---|---|
| 41 | (pyridin-2-yloxy analog; benzene with CF3 and NO2; N-piperidinyl with Boc-NH-CH2-) |
| 42 | (pyrrolidin-1-yl analog; benzene with CF3 and NO2; N-piperidinyl with Boc-NH-CH2-) |

TABLE 5-6-continued

| PEx | Str |
|---|---|
| 43 | (structure) |
| 44 | (structure) |
| 45 | (structure) |
| 46 | (structure) |

TABLE 5-6-continued

| PEx | Str |
|---|---|
| 47 | (structure) |
| 48 | (structure) |

TABLE 5-7

| PEx | Str |
|---|---|
| 49 | (structure) |

TABLE 5-7-continued

| PEx | Str |
|---|---|
| 50 | (structure) |
| 51 | (structure) |
| 52 | (structure) |
| 53 | (structure) |
| 54 | (structure) |
| 55 | (structure) |
| 56 | (structure) |

TABLE 5-8

| PEx | Str |
|---|---|
| 57 | (structure) |
| 58 | (structure) |
| 59 | (structure) |
| 60 | (structure) |

TABLE 5-8-continued

| PEx | Str |
|---|---|
| 61 | (structure) |
| 62 | (structure) |
| 63 | (structure) |
| 64 | (structure) |

TABLE 5-9
| PEx | Str |
|---|---|
| 65 | 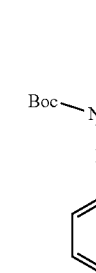 |
| 66 | |
| 67 | |
| 68 | |
TABLE 5-9-continued
| PEx | Str |
|---|---|
| 69 | 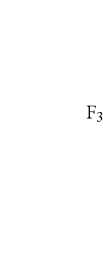 |
| 70 | |
| 71 | |
| 72 | |

TABLE 5-10

| PEx | Str |
|---|---|
| 73 | (structure) |
| 74 | (structure) |
| 75 | (structure) |
| 76 | (structure) |

TABLE 5-10-continued

| PEx | Str |
|---|---|
| 77 | (structure) |
| 78 | (structure) |
| 79 | (structure) |
| 80 | (structure) |

TABLE 5-11
| PEx | Str |
|---|---|
| 81 | 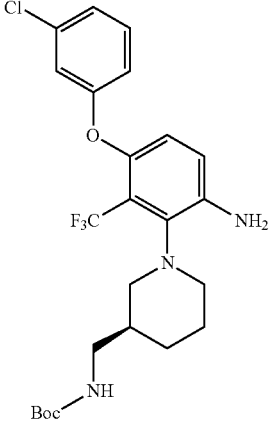 |
| 82 | 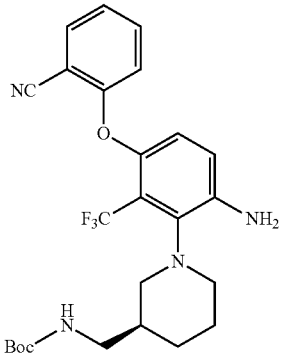 [SMILES: CC(C)(C)OC(=O)NC[C@@H]1CCCN(c2c([N+](=O)[O-])ccc(Oc3ccccc3C#N)c2C(F)(F)F)C1] |
| 83 | 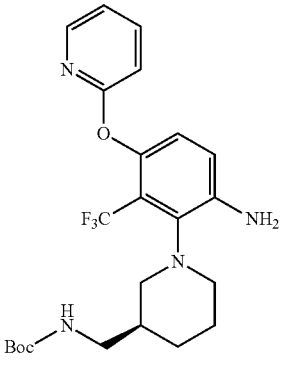 |
| 84 | 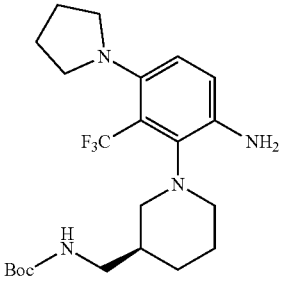 [SMILES: CC(C)(C)OC(=O)NC[C@@H]1CCCN(c2c([N+](=O)[O-])ccc(N3CCCC3)c2C(F)(F)F)C1] |
TABLE 5-11-continued
| PEx | Str |
|---|---|
| 85 | 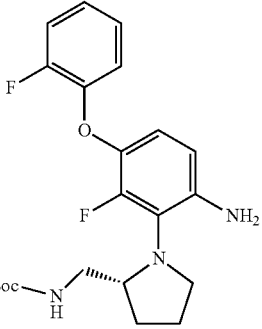 |
| 86 | 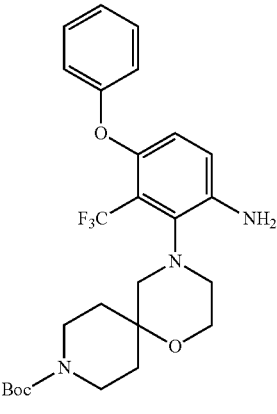 [SMILES: CC(C)(C)OC(=O)N1CCC2(CC1)CN(c1c(N)ccc(Oc3ccccc3)c1C(F)(F)F)CCO2] |
| 87 | 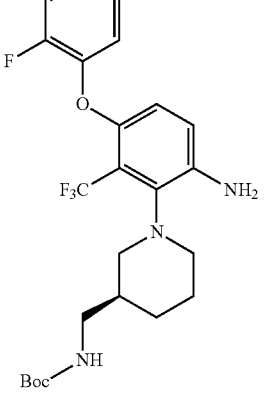 |
| 88 | 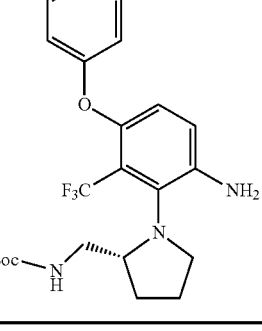 |

TABLE 5-12

| PEx | Str |
|---|---|
| 89 | (structure) |
| 90 | (structure) |
| 91 | (structure) |
| 92 | (structure) |

TABLE 5-12-continued

| PEx | Str |
|---|---|
| 93 | (structure) |
| 94 | (structure) |
| 95 | (structure) |

TABLE 5-12-continued
| PEx | Str |
|---|---|
| 96 | 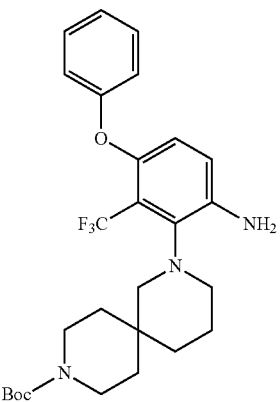 [SMILES: CC(C)(C)OC(=O)N1CCC2(CCCN(c3c(N)ccc(Oc4ccccc4)c3C(F)(F)F)C2)CC1] |
TABLE 5-13
| PEx | Str |
|---|---|
| 97 | 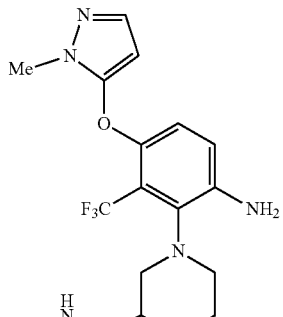 |
| 98 | 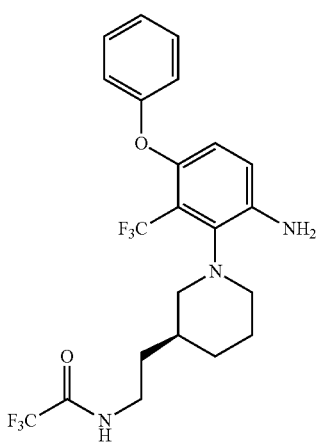 |
TABLE 5-13-continued
| PEx | Str |
|---|---|
| 99 | 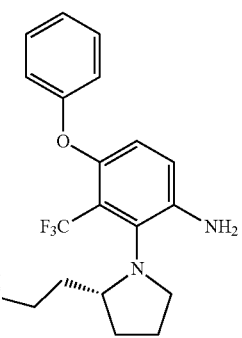 |
| 100 | |
| 101 | 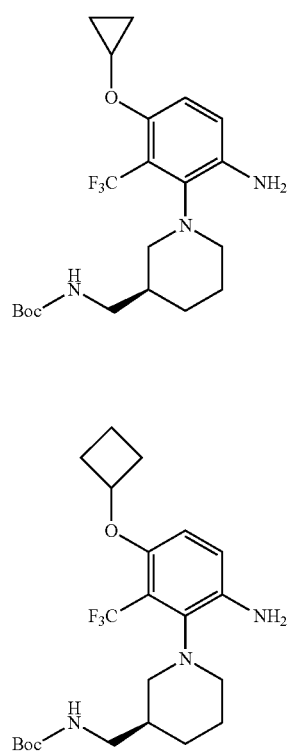 |
| 102 | |

TABLE 5-13-continued

| PEx | Str |
|---|---|
| 103 | (structure) |
| 104 | (structure) |

TABLE 5-14

| PEx | Str |
|---|---|
| 105 | (structure) |
| 106 | (structure) |

TABLE 5-14-continued

| PEx | Str |
|---|---|
| 107 | (structure) |
| 108 | (structure) |
| 109 | (structure) |
| 110 | (structure) |

TABLE 5-14-continued

| PEx | Str |
|---|---|
| 111 | (2,6-difluorophenoxy)-trifluoromethyl-aniline with N-Boc-aminomethyl piperidine |
| 112 | (2,4,6-trifluorophenoxy)-trifluoromethyl-aniline with N-Boc-aminomethyl piperidine |

TABLE 5-15

| PEx | Str |
|---|---|
| 113 | cyclopropoxy-difluoro-aniline with N-Boc-tetrahydropyridine |

TABLE 5-15-continued

| PEx | Str |
|---|---|
| 114 | phenoxy-difluoro-aniline with N-Boc-aminomethyl piperidine |
| 115 | phenoxy-trifluoromethyl-aniline with N-Boc-aminomethyl morpholine |
| 116 | phenoxy-trifluoromethyl-aniline with N-Boc-N-methyl-aminomethyl morpholine |
| 117 | phenoxy-trifluoromethyl-aniline with N-Boc-aminomethyl morpholine |

TABLE 5-15-continued

| PEx | Str |
|---|---|
| 118 | (structure) |
| 119 | (structure) |
| 120 | (structure) |

TABLE 5-16

| PEx | Str |
|---|---|
| 121 | (structure) |
| 122 | (structure) |
| 123 | (structure) |
| 124 | (structure) |
| 125 | (structure) |

TABLE 5-16-continued
| PEx | Str |
|---|---|
| 126 | 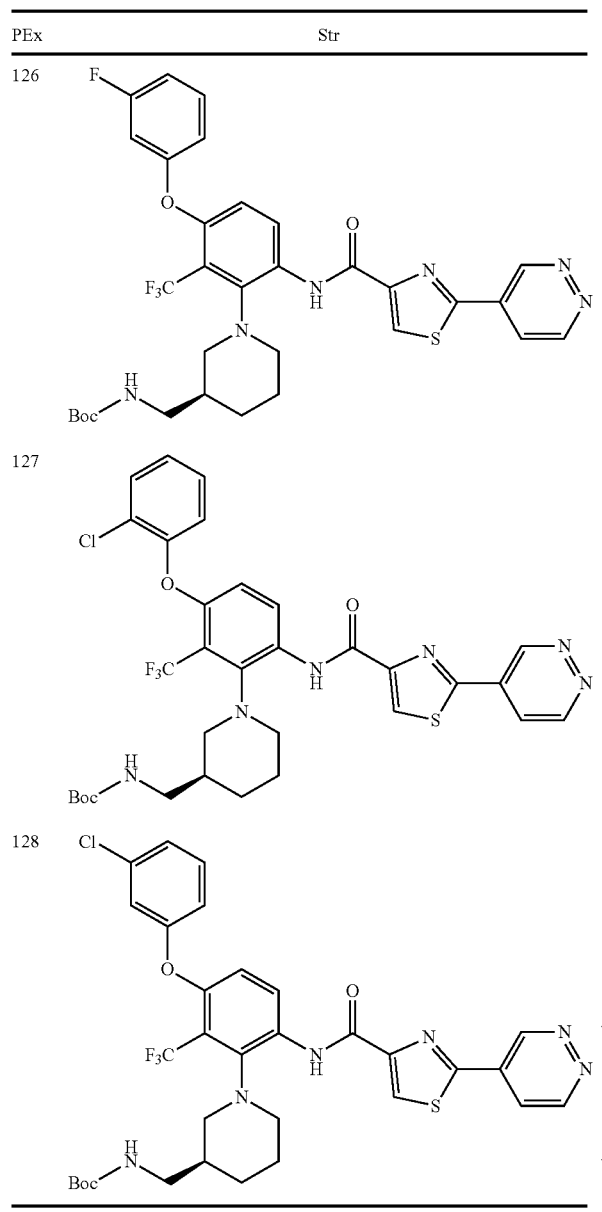 |
| 127 | |
| 128 | |
TABLE 5-17
| PEx | Str |
|---|---|
| 129 | 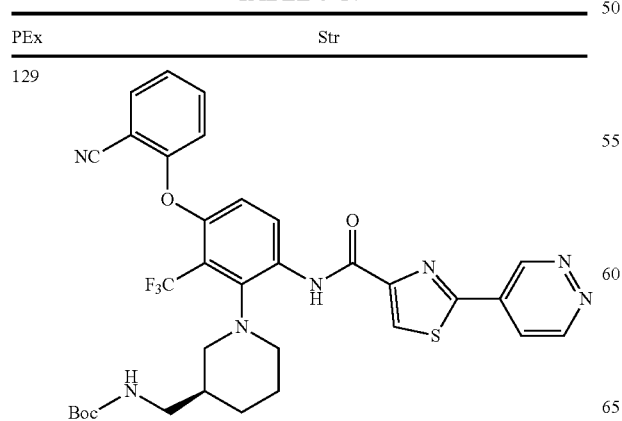 |
TABLE 5-17-continued
| PEx | Str |
|---|---|
| 130 | 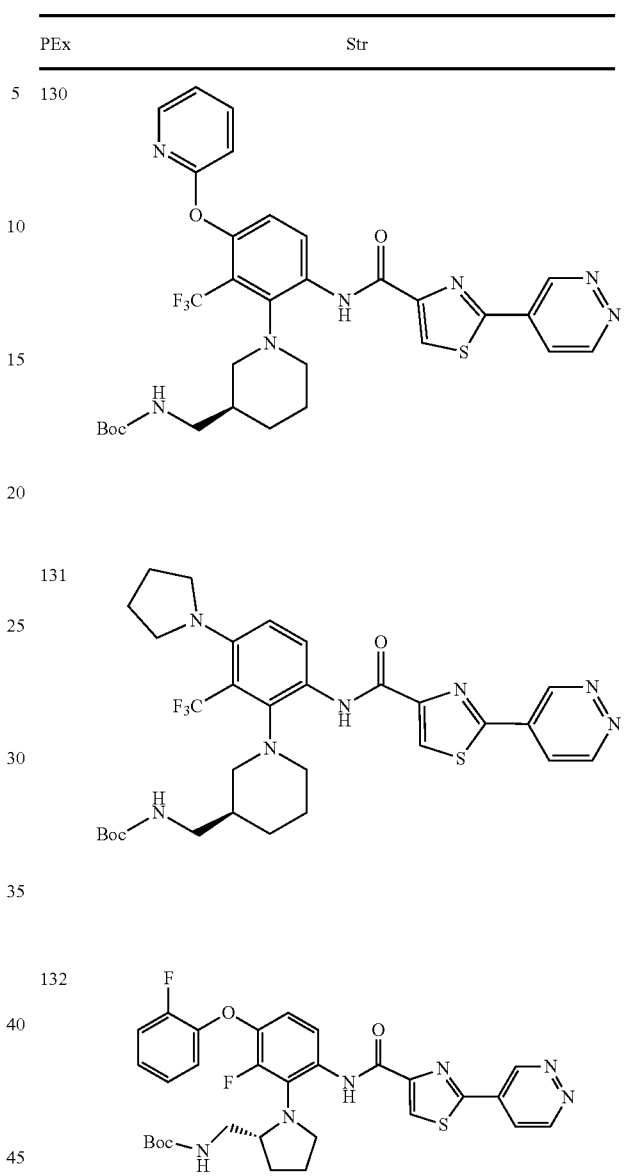 |
| 131 | |
| 132 | |
| 133 | |

TABLE 5-17-continued
| PEx | Str |
|---|---|
| 134 | 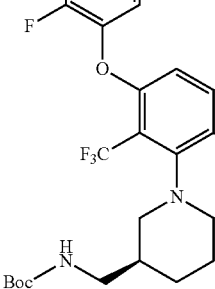 |
| 135 | 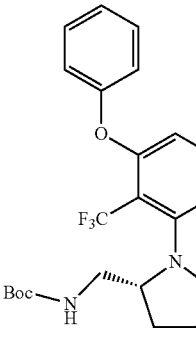 |
| 136 | 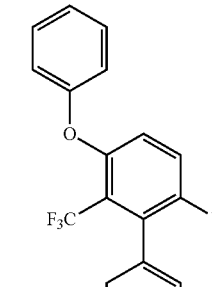 |
TABLE 5-18
| PEx | Str |
|---|---|
| 137 | 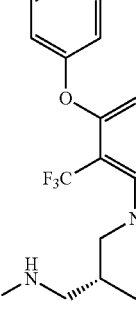 |
TABLE 5-18-continued
| PEx | Str |
|---|---|
| 138 | 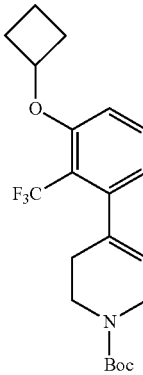 |
| 139 | 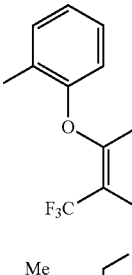 |
| 140 | |
| 141 | |

TABLE 5-18-continued
| PEx | Str |
|---|---|
| 142 | 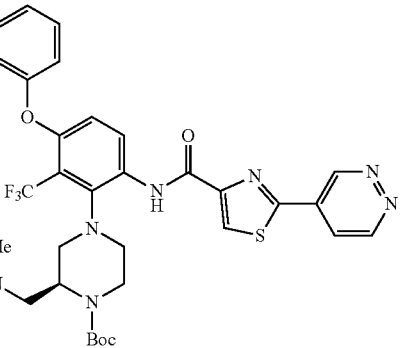 |
| 143 | 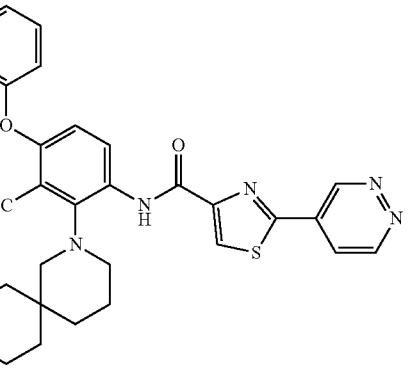 |
| 144 | 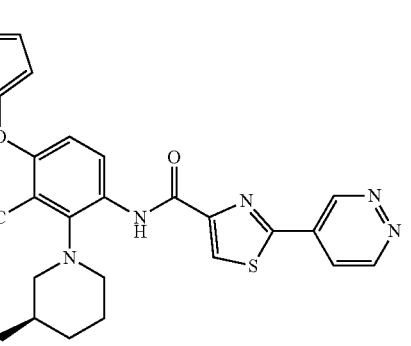 |
TABLE 5-19
| PEx | Str |
|---|---|
| 145 | 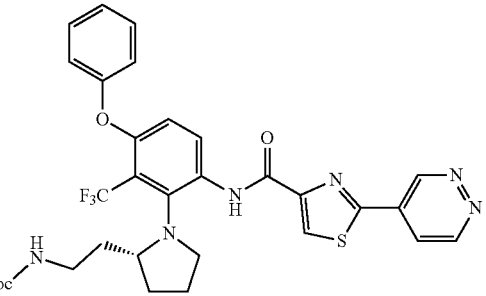 |
TABLE 5-19-continued
| PEx | Str |
|---|---|
| 146 | 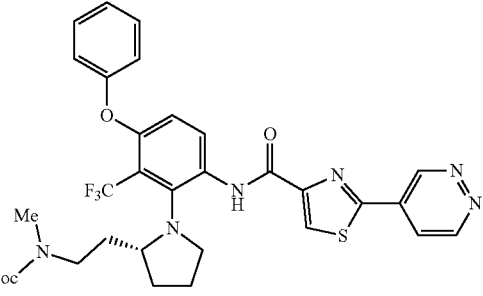 |
| 147 | 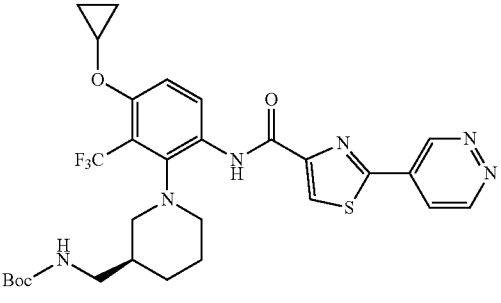 [SMILES: CC(C)(C)OC(=O)NC[C@@H]1CCCN(c2c(NC(=O)c3csc(-c4ccnnc4)n3)ccc(OC3CC3)c2C(F)(F)F)C1] |
| 148 | 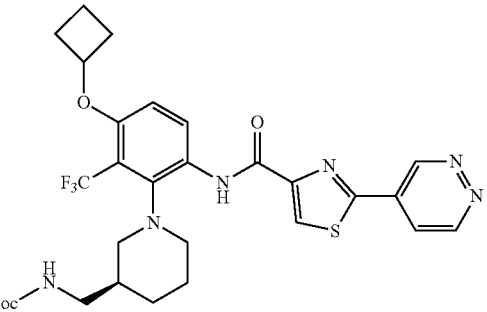 |
| 149 | 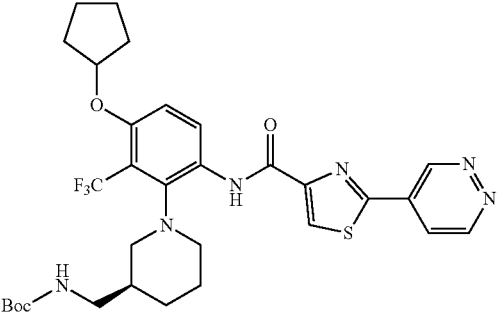 [SMILES: CC(C)(C)OC(=O)NC[C@@H]1CCCN(c2c(NC(=O)c3csc(-c4ccnnc4)n3)ccc(OC3CCCC3)c2C(F)(F)F)C1] |
| 150 | 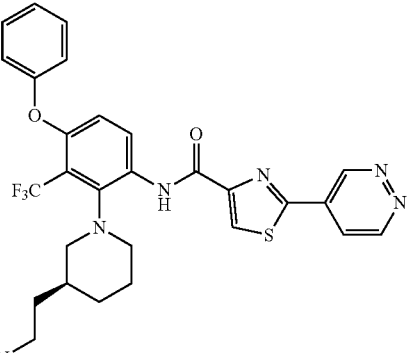 |

TABLE 5-19-continued
| PEx | Str |
|---|---|
| 151 | 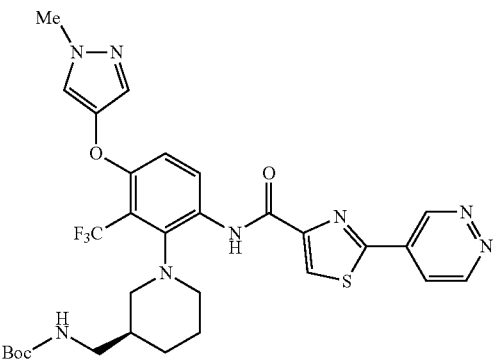 [SMILES: Cn1cc(Oc2ccc(NC(=O)c3csc(-c4ccnnc4)n3)c(N3CCC[C@@H](CNC(=O)OC(C)(C)C)C3)c2C(F)(F)F)cn1] |
| 152 | 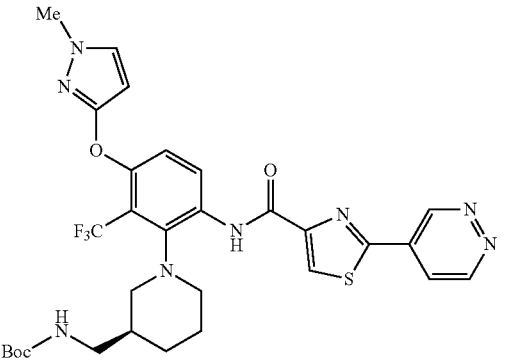 [SMILES: Cn1ccc(Oc2ccc(NC(=O)c3csc(-c4ccnnc4)n3)c(N3CCC[C@@H](CNC(=O)OC(C)(C)C)C3)c2C(F)(F)F)n1] |
TABLE 5-20
| PEx | Str |
|---|---|
| 153 | 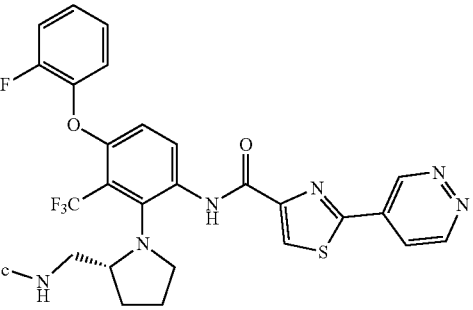 |
| 154 | 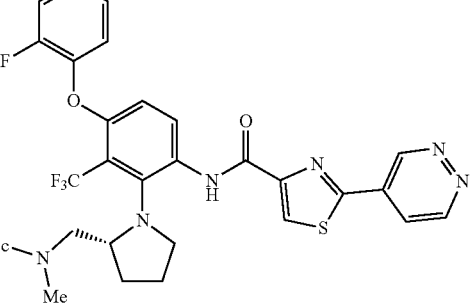 |
| 155 | |
| 156 | |
| 157 | 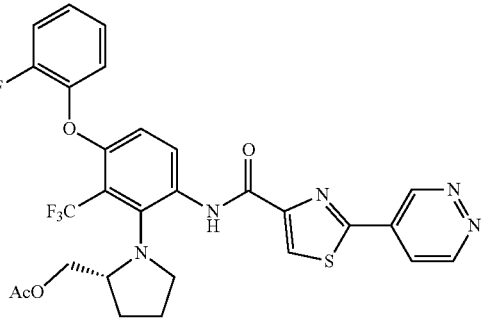 |
| 158 | 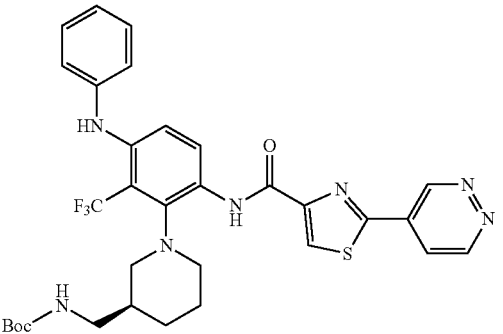 [SMILES: CC(C)(C)OC(=O)NC[C@@H]1CCCN(c2c(NC(=O)c3csc(-c4ccnnc4)n3)ccc(Nc3ccccc3)c2C(F)(F)F)C1] |

TABLE 5-20-continued

| PEx | Str |
|---|---|
| 159 | (structure) |
| 160 | (structure) |

TABLE 5-21

| PEx | Str |
|---|---|
| 161 | (structure) |
| 162 | (structure) |

TABLE 5-21-continued

| PEx | Str |
|---|---|
| 163 | (structure) |
| 164 | (structure) |
| 165 | (structure) |
| 166 | (structure) |
| 167 | (structure) |

TABLE 5-21-continued
| PEx | Str |
|---|---|
| 168 | 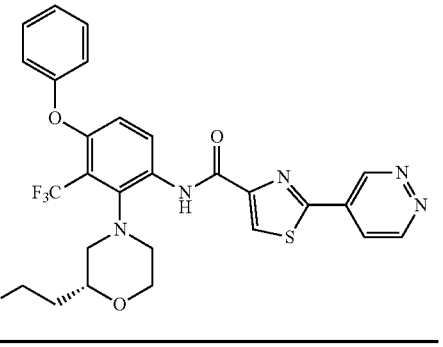 |
TABLE 5-22
| PEx | Str |
|---|---|
| 169 | 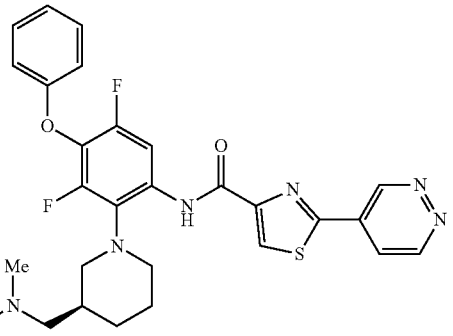 |
| 170 | 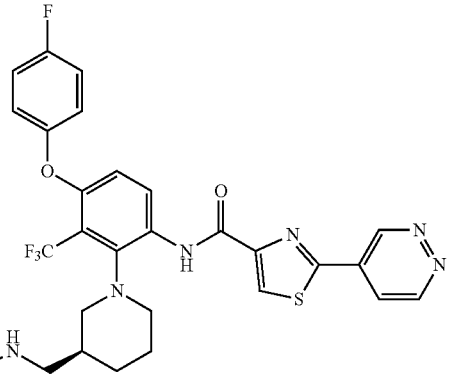 |
| 171 | 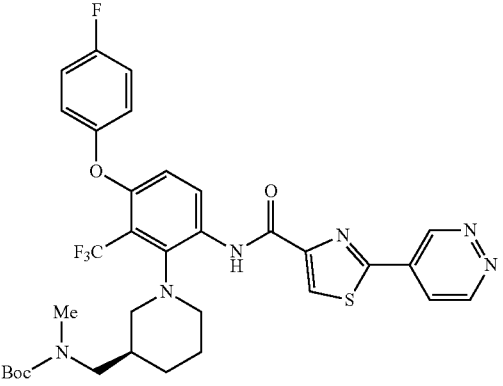 [SMILES: CN(C[C@@H]1CCCN(c2c(NC(=O)c3csc(-c4ccnnc4)n3)ccc(Oc3ccc(F)cc3)c2C(F)(F)F)C1)C(=O)OC(C)(C)C] |
TABLE 5-22-continued
| PEx | Str |
|---|---|
| 172 | 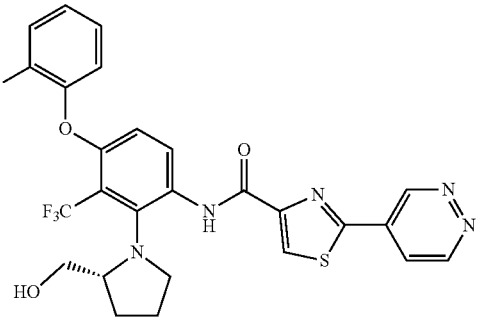 |
| 173 | 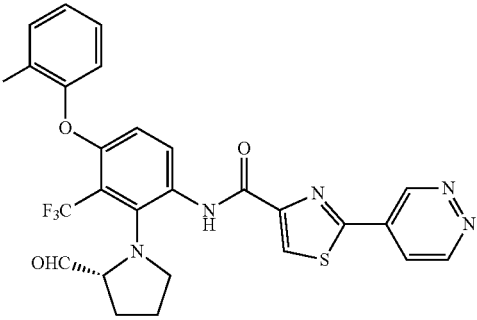 |
| 174 | 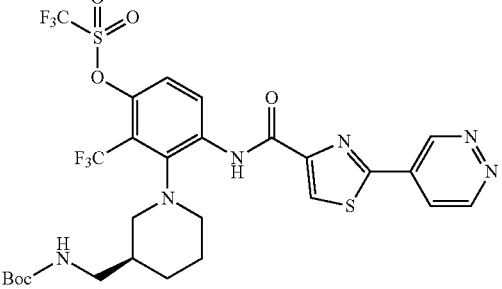 |
| 175 | 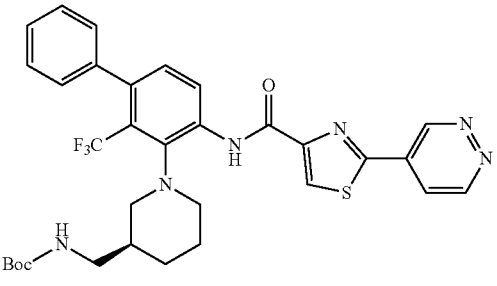 [SMILES: CC(C)(C)OC(=O)NC[C@@H]1CCCN(c2c(NC(=O)c3csc(-c4ccnnc4)n3)ccc(-c3ccccc3)c2C(F)(F)F)C1] |

TABLE 5-22-continued
| PEx | Str |
|---|---|
| 176 | 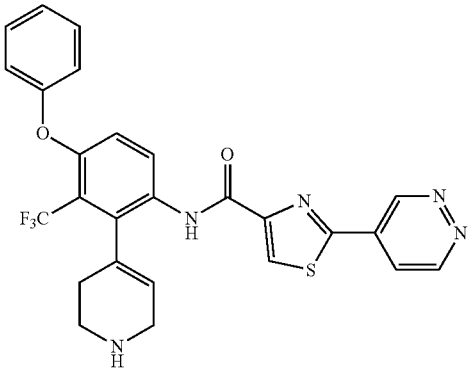 [SMILES: O=C(Nc1ccc(Oc2ccccc2)c(C(F)(F)F)c1C1=CCNCC1)c1csc(-c2ccnnc2)n1] |
TABLE 5-23
| PEx | Str |
|---|---|
| 177 | 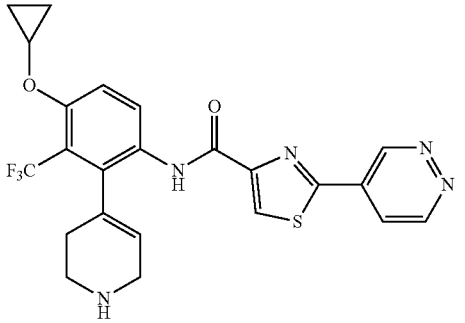 [SMILES: O=C(Nc1ccc(OC2CC2)c(C(F)(F)F)c1C1=CCNCC1)c1csc(-c2ccnnc2)n1] |
| 178 | 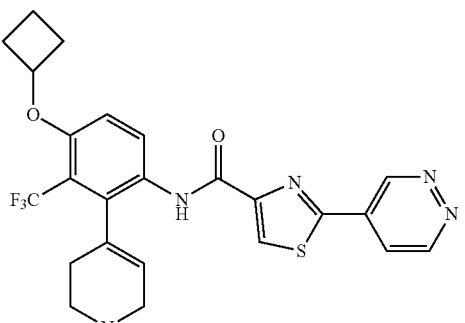 |
| 179 | 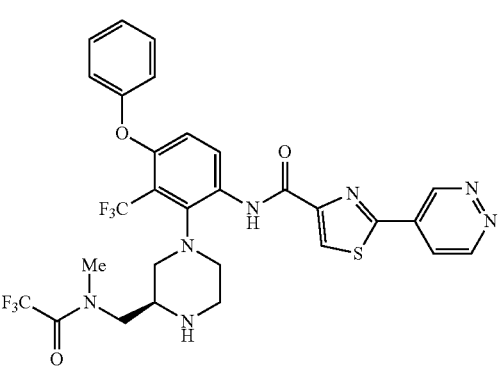 [SMILES: CN(C[C@H]1CN(c2c(NC(=O)c3csc(-c4ccnnc4)n3)ccc(Oc3ccccc3)c2C(F)(F)F)CCN1)C(=O)C(F)(F)F] |
TABLE 5-23-continued
| PEx | Str |
|---|---|
| 180 | 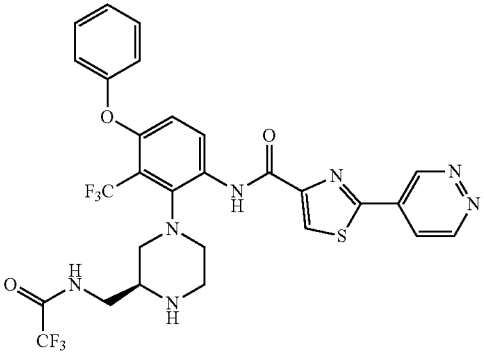 [SMILES: O=C(Nc1ccc(Oc2ccccc2)c(C(F)(F)F)c1N1CCN[C@@H](CNC(=O)C(F)(F)F)C1)c1csc(-c2ccnnc2)n1] |
| 181 | 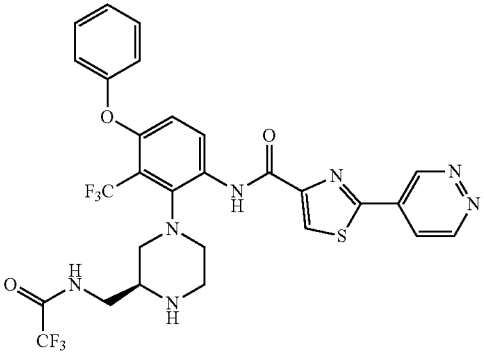 [SMILES: O=C(Nc1ccc(Oc2ccccc2)c(C(F)(F)F)c1N1CCN[C@@H](CNC(=O)C(F)(F)F)C1)c1csc(-c2ccnnc2)n1] |
| 182 | 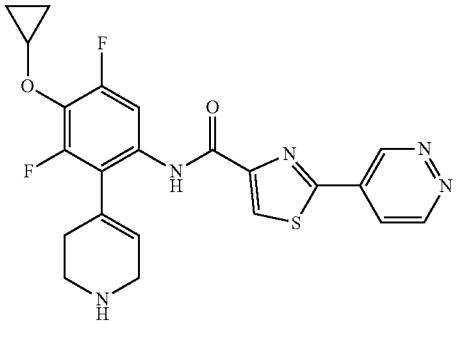 [SMILES: O=C(Nc1cc(F)c(OC2CC2)c(F)c1C1=CCNCC1)c1csc(-c2ccnnc2)n1] |
| 183 | 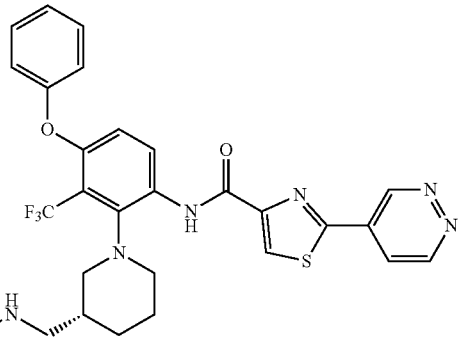 |

TABLE 5-23-continued
| PEx | Str |
|---|---|
| 184 | 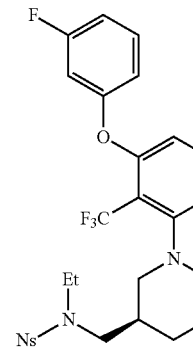 |
TABLE 5-24
| PEx | Str |
|---|---|
| 185 | |
| 186 | |
| 187 | |
TABLE 5-24-continued
| PEx | Str |
|---|---|
| 188 | 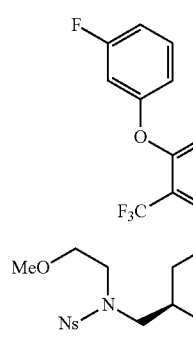 |
| 189 | |
| 190 | 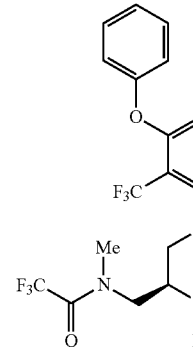 |
| 191 | 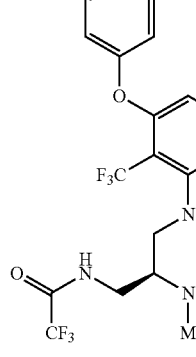 |

TABLE 5-25

| PEx | Str |
|---|---|
| 192 | (phenylthio)(trifluoromethyl)(bromo)(nitro)benzene |
| 193 | 2,4-difluoro-3-(methylsulfonyl)-1-nitrobenzene |
| 194 | 4-nitro-3-fluoro-2-(trifluoromethyl)benzoic acid |
| 195 | (4-nitro-3-fluoro-2-(trifluoromethyl)phenyl)(phenyl)methanone |
| 196-1 | (S)-tert-butyldiphenylsilyloxy pyrrolidine-2,5-dione derivative |
| 196-2 | (R)-tert-butyldiphenylsilyloxy pyrrolidine-2,5-dione derivative |
| 197 | (S)-octahydropyrrolo[1,2-a]pyrazin-ol |

TABLE 5-25-continued

| PEx | Str |
|---|---|
| 198 | (R)-octahydropyrrolo[1,2-a]pyrazin-ol |

TABLE 5-26

| PEx | Str |
|---|---|
| 199 | 1-phenoxy-3-(methylsulfonyl)-2-fluoro-4-nitrobenzene |
| 200 | 1-cyclopropoxy-2-methyl-3-chloro-4-nitrobenzene |
| 201 | 1-phenoxy-2-methyl-3-chloro-4-nitrobenzene |
| 202 | 1-cyclopropoxy-2-(trifluoromethyl)-3-bromo-4-nitrobenzene |

TABLE 5-26-continued

| PEx | Str |
|---|---|
| 203 | (structure) |
| 204 | (structure) |
| 205 | (structure) |
| 206 | (structure) |

TABLE 5-27

| PEx | Str |
|---|---|
| 207 | (structure) |
| 208 | (structure) |
| 209 | (structure) |
| 210 | (structure) |

TABLE 5-27-continued

| PEx | Str |
|---|---|
| 211 | (chemical structure) |
| 212 | (chemical structure) |
| 213 | (chemical structure) |
| 214 | (chemical structure) |

TABLE 5-28

| PEx | Str |
|---|---|
| 215 | (chemical structure) |
| 216 | (chemical structure) |
| 217 | (chemical structure) |

TABLE 5-28-continued
| PEx | Str |
|---|---|
| 218 | 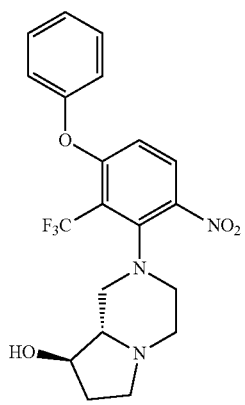 [SMILES: O=[N+]([O-])c1ccc(Oc2ccccc2)c(C(F)(F)F)c1N1CCN2CC[C@@H](O)[C@@H]2C1] |
| 219 | 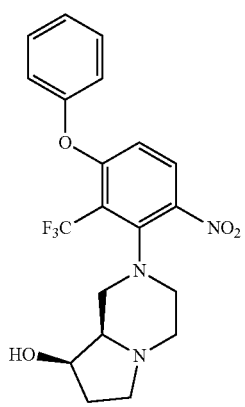 [SMILES: O=[N+]([O-])c1ccc(Oc2ccccc2)c(C(F)(F)F)c1N1CCN2CC[C@@H](O)[C@H]2C1] |
| 220 | 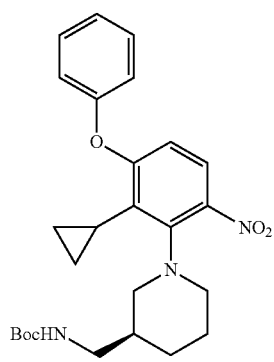 [SMILES: CC(C)(C)OC(=O)NC[C@@H]1CCCN(c2c([N+](=O)[O-])ccc(Oc3ccccc3)c2C2CC2)C1] |
| 221 | 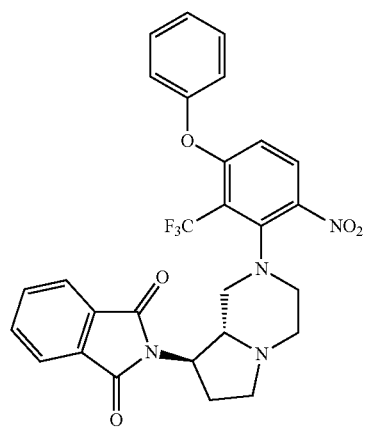 [SMILES: O=C1c2ccccc2C(=O)N1[C@@H]1CCN2CCN(c3c([N+](=O)[O-])ccc(Oc4ccccc4)c3C(F)(F)F)C[C@@H]12] |
TABLE 5-28-continued
| PEx | Str |
|---|---|
| 222 | 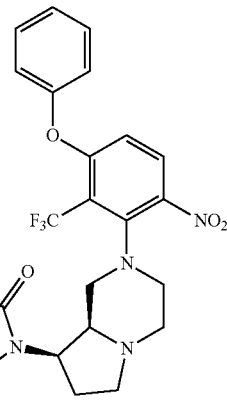 |
TABLE 5-29
| PEx | Str |
|---|---|
| 223 | 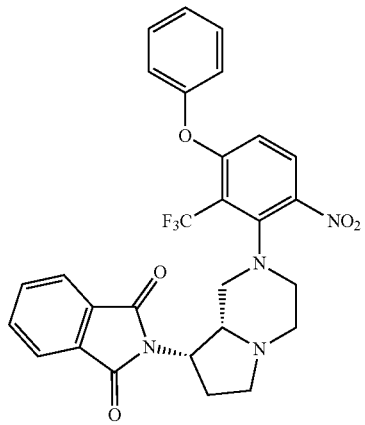 [SMILES: O=C1c2ccccc2C(=O)N1[C@H]1CCN2CCN(c3c([N+](=O)[O-])ccc(Oc4ccccc4)c3C(F)(F)F)C[C@@H]12] |
| 224 | 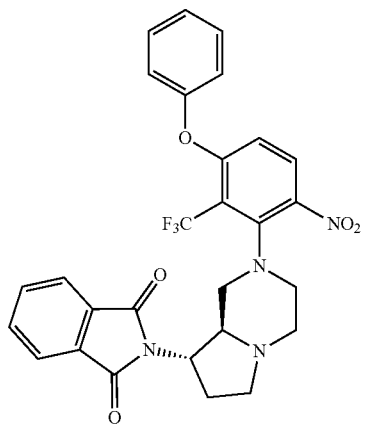 [SMILES: O=C1c2ccccc2C(=O)N1[C@H]1CCN2CCN(c3c([N+](=O)[O-])ccc(Oc4ccccc4)c3C(F)(F)F)C[C@H]12] |

TABLE 5-29-continued

| PEx | Str |
|---|---|
| 225 | (structure) |
| 226 | (structure) |
| 227 | (structure) |
| 228 | (structure) |
| 229 | (structure) |
| 230 | (structure) |

TABLE 5-30

| PEx | Str |
|---|---|
| 231 | (structure) |

TABLE 5-30-continued
| PEx | Str |
|---|---|
| 232 | 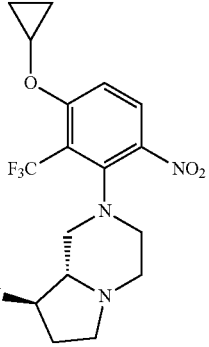 |
| 233 | 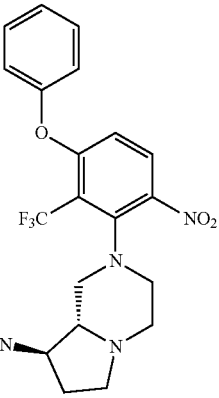 |
| 234 | 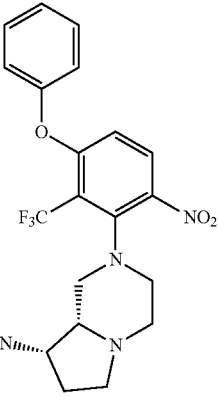 |
| 235 | 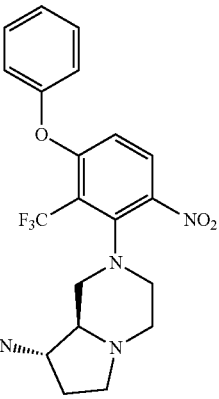 |
| 236 | 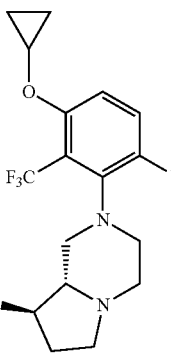 |
| 237 | 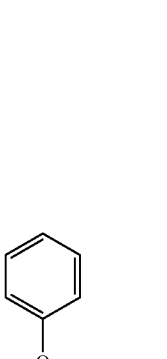 |
| 238 | 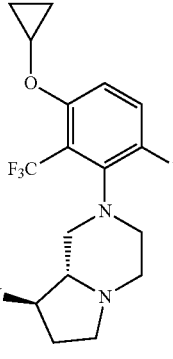 |

TABLE 5-31
| PEx | Str |
|---|---|
| 239 | |
| 240 | |
| 241 | |
| 242 | |
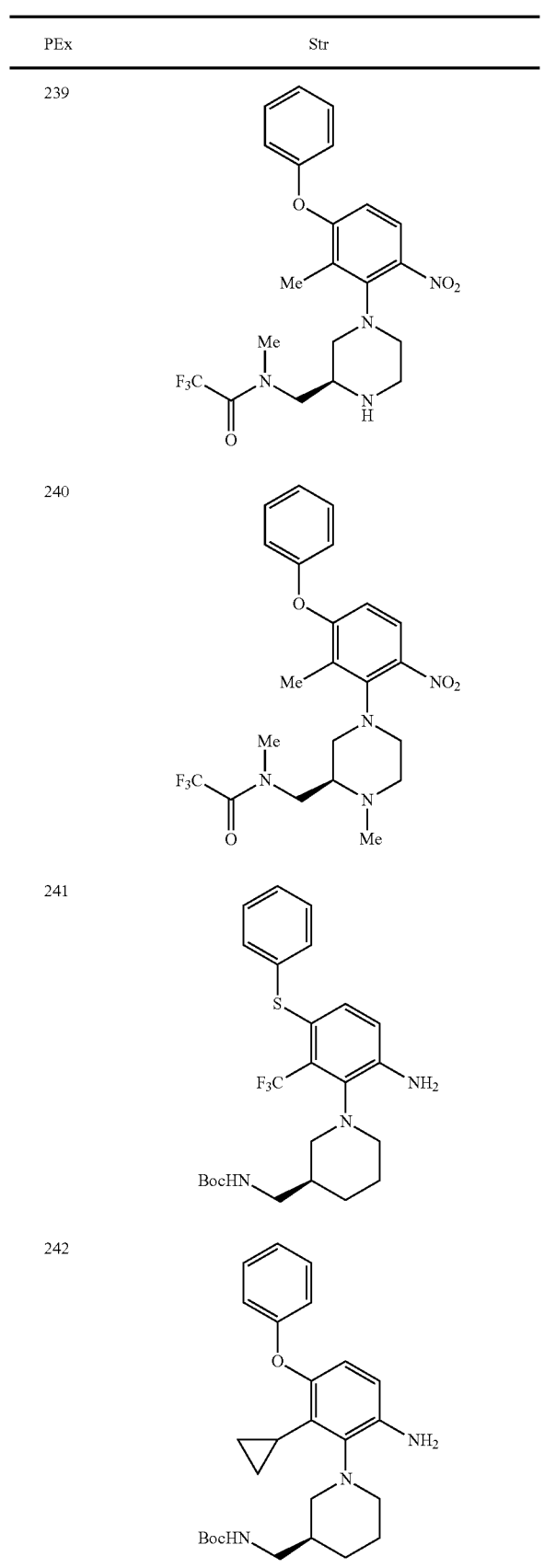
TABLE 5-31-continued
| PEx | Str |
|---|---|
| 243 | |
| 244 | |
| 245 | |
| 246 | |
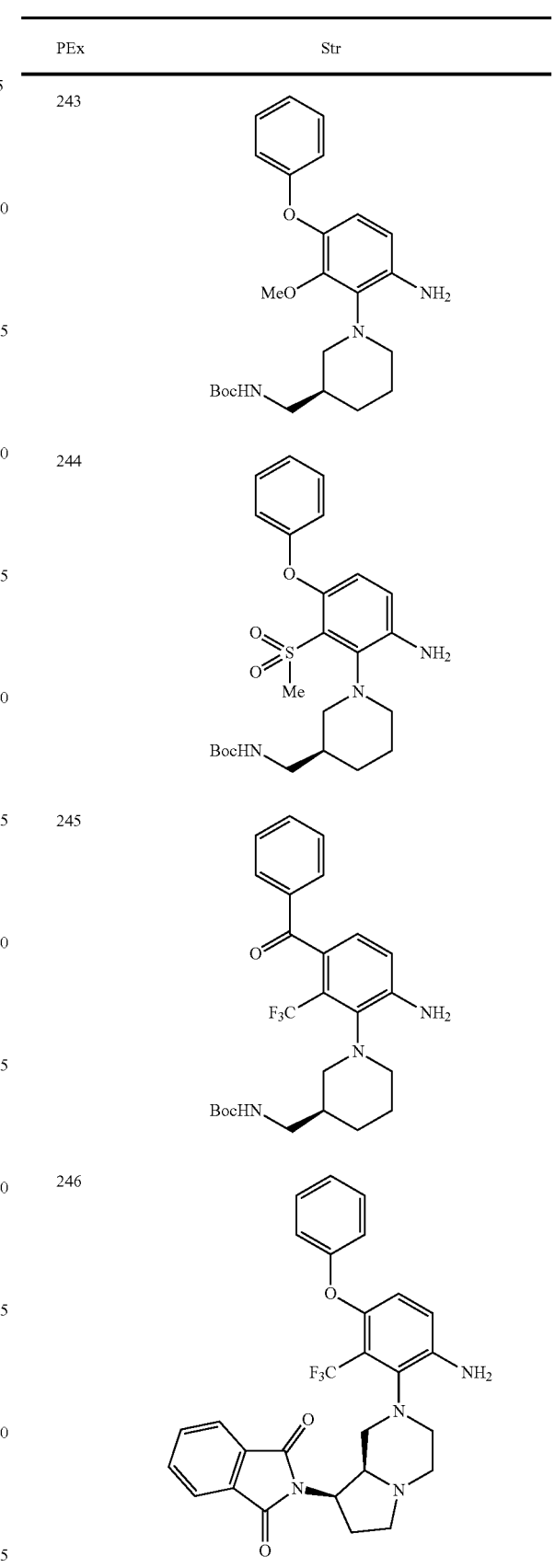

TABLE 5-32
| PEx | Str |
|---|---|
| 247 | 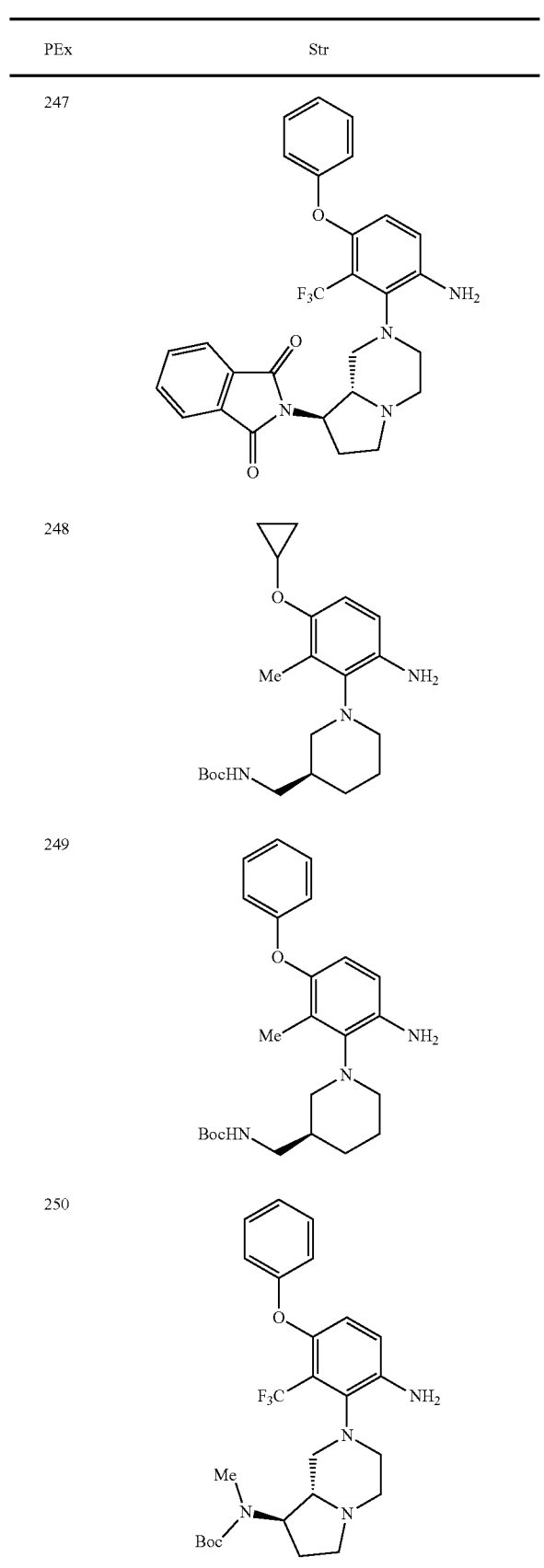 |
| 248 | |
| 249 | |
| 250 | |
TABLE 5-32-continued
| PEx | Str |
|---|---|
| 251 | 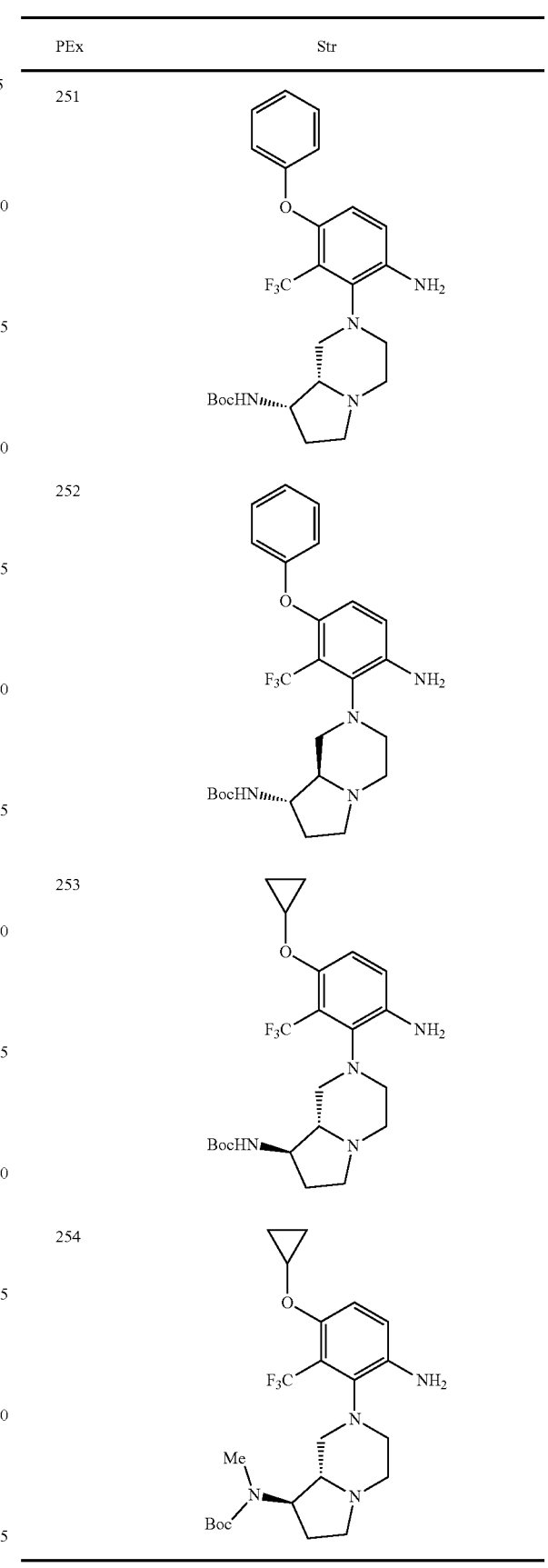 |
| 252 | |
| 253 | |
| 254 | |

TABLE 5-33
| PEx | Str |
|---|---|
| 255 | 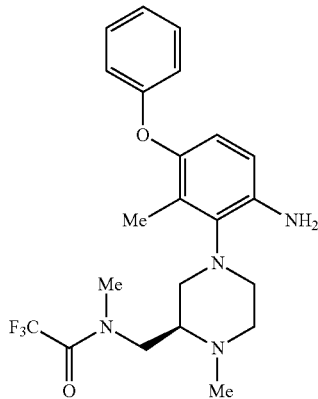 [SMILES: Cc1c(Oc2ccccc2)ccc([N+](=O)[O-])c1N1CCN(C)[C@@H](CN(C)C(=O)C(F)(F)F)C1] |
| 256 | 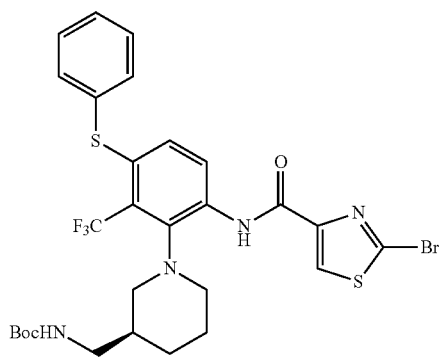 [SMILES: CC(C)(C)OC(=O)NC[C@@H]1CCCN(c2c(NC(=O)c3csc(Br)n3)ccc(Sc3ccccc3)c2C(F)(F)F)C1] |
| 257 | 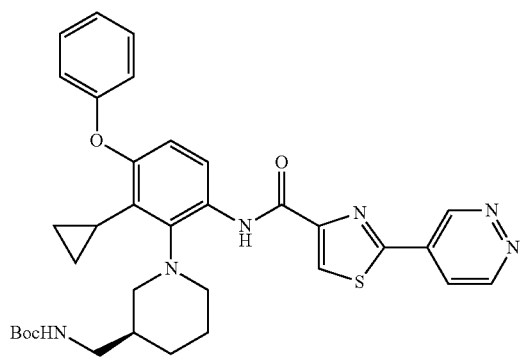 [SMILES: CC(C)(C)OC(=O)NC[C@@H]1CCCN(c2c(NC(=O)c3csc(-c4ccnnc4)n3)ccc(Oc3ccccc3)c2C2CC2)C1] |
| 258 | 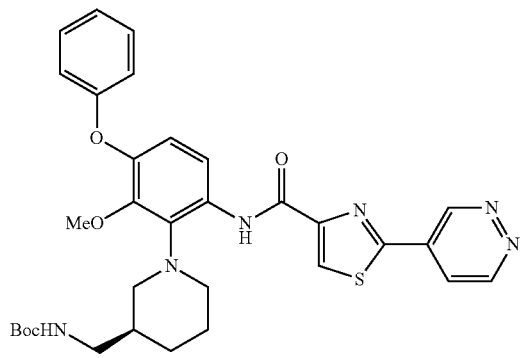 [SMILES: COc1c(Oc2ccccc2)ccc(NC(=O)c2csc(-c3ccnnc3)n2)c1N1CCC[C@@H](CNC(=O)OC(C)(C)C)C1] |

TABLE 5-33-continued
| PEx | Str |
|---|---|
| 259 | 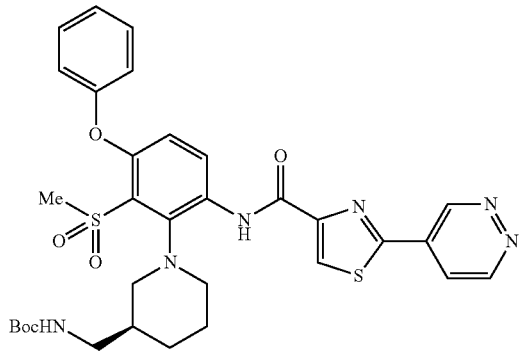 [SMILES: CC(C)(C)OC(=O)NC[C@@H]1CCCN(c2c(NC(=O)c3csc(-c4ccnnc4)n3)ccc(Oc3ccccc3)c2S(C)(=O)=O)C1] |
| 260 | 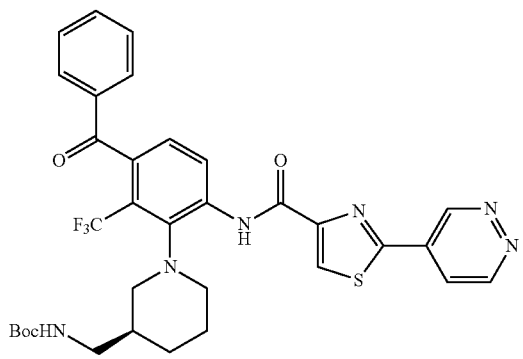 [SMILES: CC(C)(C)OC(=O)NC[C@@H]1CCCN(c2c(NC(=O)c3csc(-c4ccnnc4)n3)ccc(C(=O)c3ccccc3)c2C(F)(F)F)C1] |
| 261 | 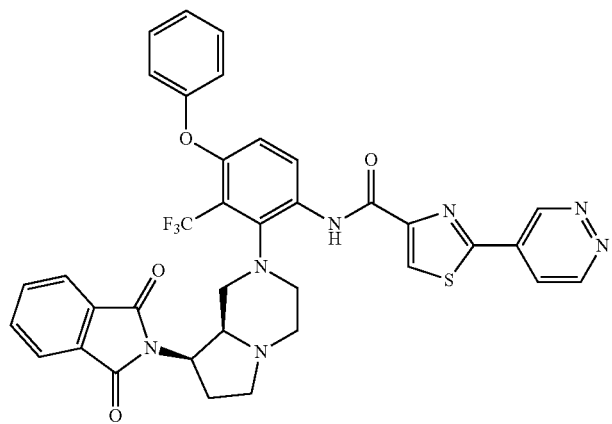 [SMILES: O=C(Nc1ccc(Oc2ccccc2)c(C(F)(F)F)c1N1CCN2CC[C@@H](N3C(=O)c4ccccc4C3=O)[C@H]2C1)c1csc(-c2ccnnc2)n1] |

TABLE 5-33-continued
| PEx | Str |
|---|---|
| 262 | 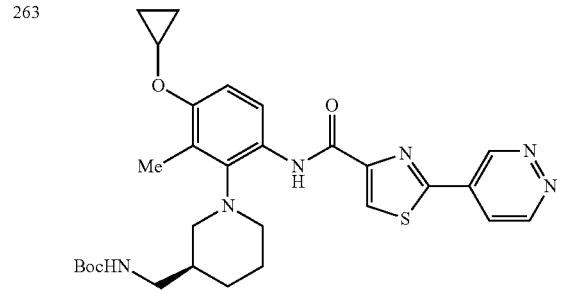 |
TABLE 5-34
| PEx | Str |
|---|---|
| 263 | 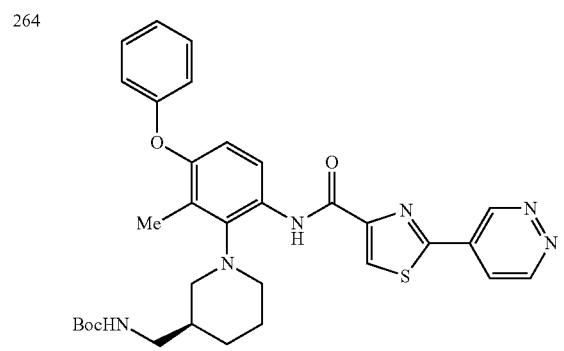 |
| 264 | 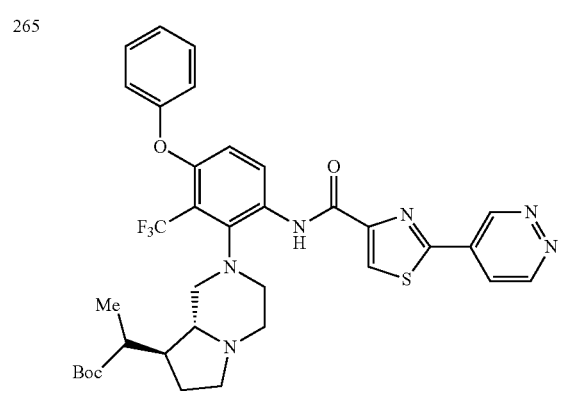 |
| 265 | |
TABLE 5-34-continued
| PEx | Str |
|---|---|
| 266 | 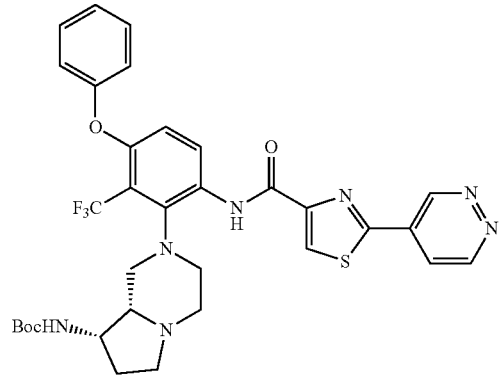 [SMILES: CC(C)(C)OC(=O)N[C@H]1CCN2CCN(c3c(NC(=O)c4csc(-c5ccnnc5)n4)ccc(Oc4ccccc4)c3C(F)(F)F)C[C@@H]12] |
| 267 | 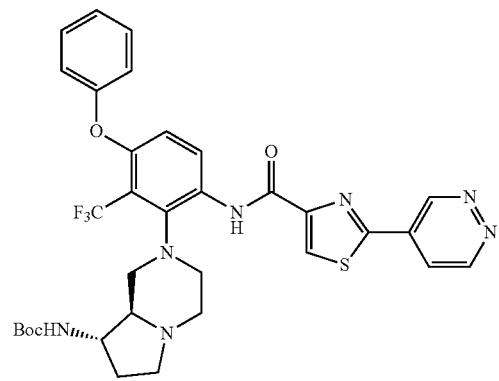 |

TABLE 5-34-continued

| PEx | Str |
|---|---|
| 268 | 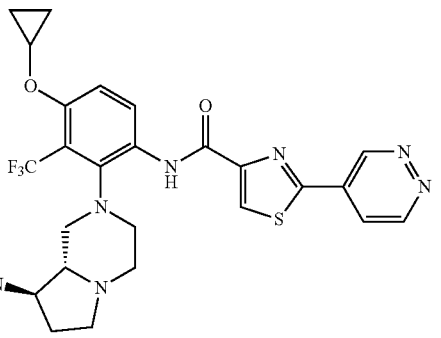 |
| 269 | 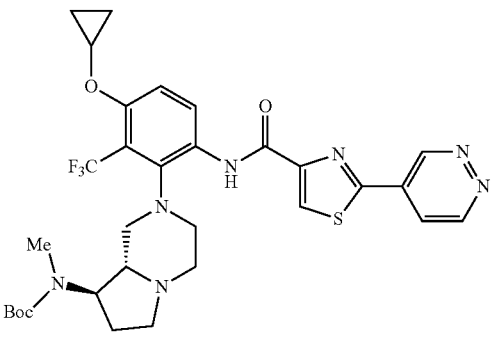 [SMILES: CN(C(=O)OC(C)(C)C)[C@@H]1CCN2CCN(c3c(NC(=O)c4csc(-c5ccnnc5)n4)ccc(OC4CC4)c3C(F)(F)F)C[C@@H]12] |
| 270 | 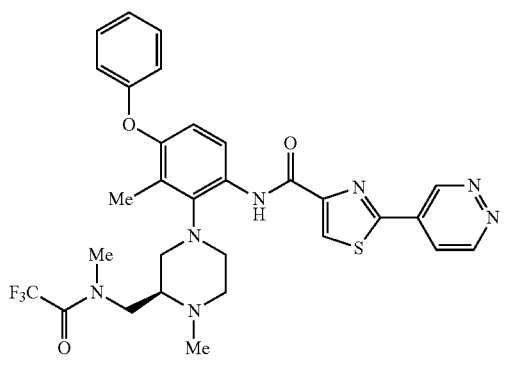 [SMILES: Cc1c(Oc2ccccc2)ccc(NC(=O)c2csc(-c3ccnnc3)n2)c1N1CCN(C)[C@@H](CN(C)C(=O)C(F)(F)F)C1] |

TABLE 5-35

| PEx | Str |
|---|---|
| 271 | 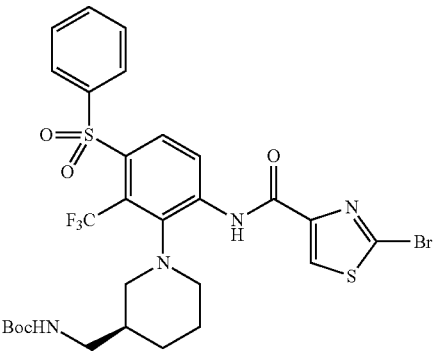 [SMILES: CC(C)(C)OC(=O)NC[C@@H]1CCCN(c2c(NC(=O)c3csc(Br)n3)ccc(S(=O)(=O)c3ccccc3)c2C(F)(F)F)C1] |
| 272 | 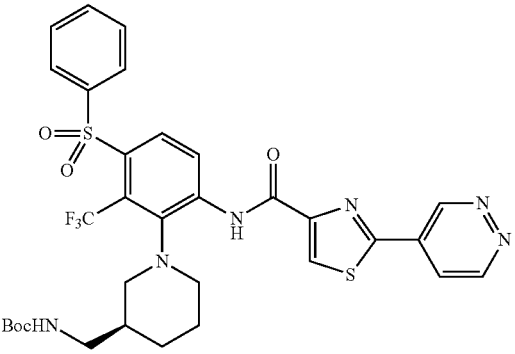 [SMILES: CC(C)(C)OC(=O)NC[C@@H]1CCCN(c2c(NC(=O)c3csc(-c4ccnnc4)n3)ccc(S(=O)(=O)c3ccccc3)c2C(F)(F)F)C1] |

TABLE 6-1

| PEx | PSyn | DAT |
|---|---|---|
| 1 | 1 | NMR DMSO-d6 (500 MHz): 7.16-7.21 (3H, m), 7.26-7.32 (1H, m), 7.45-7.51 (2H, m), 8.15-8.20 (1H, m) |
| 2 | 1 | ESI+: 402.3 |
| 3 | 1 | NMR CDCl3 (500 MHz): 6.73-6.85 (2H, m), 6.92-7.00 (1H, m), 7.01-7.05 (1H, m), 7.37-7.44 (1H, m), 7.69-7.73 (1H, m) |
| 4 | 1 | NMR CDCl3 (500 MHz): 6.90-6.94 (1H, m), 7.01-7.06 (2H, m), 7.10-7.16 (2H, m), 7.65-7.69 (1H, m) |
| 5 | 1 | NMR DMSO-d6 (500 MHz): 7.04-7.08 (1H, m), 7.36-7.40 (2H, m), 7.46-7.50 (1H, m), 7.68-7.71 (1H, m), 8.15-8.18 (1H, m) |
| 6 | 1 | NMR DMSO-d6 (500 MHz): 7.15-7.19 (1H, m), 7.32-7.36 (2H, m), 7.37-7.39 (1H, m), 7.49 (1H, t), 8.19-8.23 (1H, m) |
| 7 | 1 | ESI+: 387.1 |
| 8 | 1 | ESI+: 365.1 |
| 9 | 1 | ESI+: 341.2 |
| 10 | 1 | NMR DMSO-d6 (500 MHz): 7.08-7.14 (1H, m), 7.30-7.53 (4H, m), 8.01 (1H, dd) |
| 11 | 1 | NMR CDCl3 (400 MHz): 6.98 (2H, d), 7.15-7.19 (1H, m), 7.33-7.39 (2H, m), 7.74 (1H, dd) |
| 12 | 1 | NMR CDCl3 (400 MHz): 5.28 (2H, s), 7.05 (1H, d), 7.34-7.44 (5H, m), 7.85 (1H, d) |
| 13 | 13 | ESI+: 413.1 |
| 14 | 13 | ESI+: 363.3 |
| 15 | 13 | NMR CDCl3 (400 MHz): 1.50 (9H, s), 2.38 (2H, br s), 3.68 (2H, br s), 4.03 (2H, br s), 5.61 (1H, br s), 7.66-7.71 (1H, m) |
| 16 | 16 | ESI+: 422.3 |
| 17 | 17 | ESI+: 487.2 |
| 18 | 17 | ESI+: 451.2 |
| 19 | 17 | ESI+: 415.3 |
| 20 | 17 | NMR CDCl3 (400 MHz): 0.69-0.74 (2H, m), 0.89-0.93 (2H, m), 1.50 (9H, s), 2.38 (2H, br s), 3.68 (2H, br s), 4.01 (2H, br s), 4.34-4.39 (1H, m), 5.55-5.58 (1H, m), 7.61 (1H, d) |

TABLE 6-2

| PEx | PSyn | DAT |
|---|---|---|
| 21 | 21 | ESI+: 460.5 |
| 22 | 21 | ESI+: 474.7 |
| 23 | 21 | ESI+: 488.2 |
| 24 | 21 | ESI+: 500.2 |
| 25 | 21 | ESI+: 400.1 |
| 26 | 21 | ESI+: 495.3 |
| 27 | 21 | ESI+: 510.3 |
| 28 | 21 | ESI+: 532.2 |
| 29 | 21 | ESI+: 550.2 |

TABLE 6-2-continued

| PEx | PSyn | DAT |
|---|---|---|
| 30 | 30 | NMR CDCl3(400 MHz): 1.33-1.44 (1H, m), 1.68-1.79 (1H, m), 1.91-1.99 (2H, m), 2.21-2.27 (1H, m), 2.77-2.83 (1H, m), 2.88-2.94 (1H, m), 3.30-3.38 (2H, m), 3.61-3.71 (2H, m), 7.81-7.89 (4H, m) |
| 31 | 31 | ESI+: 265.4 |
| 32 | 32 | ESI+: 347.4 |
| 33 | 33 | ESI+: 225.4 |
| 34 | 34 | ESI+: 496.2 |
| 35 | 34 | ESI+: 536.4 |
| 36 | 34 | ESI+: 536.4 |
| 37 | 34 | ESI+: 536.4 |
| 38 | 34 | ESI+: 530.2 |
| 39 | 34 | ESI+: 552.3, 554.3 |
| 40 | 34 | ESI+: 543.4 |
| 41 | 34 | ES 1+: 497.3 |
| 42 | 34 | ESI+: 495.4 |
| 43 | 34 | ESI+: 450.4 |
| 44 | 34 | ESI+: 494.2 |
| 45 | 34 | NMR CDCl3(400 MHz): 1.19-1.22 (1H, m), 1.68-1.85 (3H, m), 2.18 (1H, br s), 2.79-2.84 (1H, m), 3.02-3.09 (3H, m), 3.50-3.61 (2H, m), 5.18 (2H, s), 6.80 (1H, d), 7.31-7.42 (5H, m), 7.64 (1H, d), 7.69-7.72 (2H, m), 7.81-7.85 (2H, m) |
| 46 | 34 | ESI+: 496.4 |
| 47 | 34 | ESI+: 560.4 |
| 48 | 34 | ESI+: 482.2 |

TABLE 6-3

| PEx | PSyn | DAT |
|---|---|---|
| 49 | 34 | ESI+: 520.3 |
| 50 | 34 | ESI+: 558.4 |
| 51 | 34 | ESI+: 506.3 |
| 52 | 34 | ESI+: 518.4 |
| 53 | 34 | ESI+: 522.2 |
| 54 | 34 | NMR CDCl3(400 MHz): 1.46 (9H, s), 2.89-3.13 (4H, m), 3.28-3.33 (2H, m), 3.71-3.88 (3H, m), 4.88 (1H, br s), 6.73 (1H, d), 7.04-7.06 (2H, m), 7.22-7.24 (1H, m), 7.40-7.44 (2H, m), 7.63 (1H, d) |
| 55 | 34 | NMR CDCl3(400 MHz): 1.46 (9H, s), 2.90 (1H, d), 2.96-3.14 (3H, m), 3.27-3.34 (2H, m), 3.71-3.81 (2H, m), 3.87 (1H, dd), 4.88 (1H, br s), 6.73 (1H, d), 7.04-7.06 (2H, m), 7.22-7.26 (1H, m), 7.40-7.44 (2H, m), 7.63 (1H, d) |
| 56 | 34 | ESI+: 534.4 |
| 57 | 34 | NMR CDCl3(400 MHz): 1.14-1.20 (1H, m), 1.42 (9H, s), 1.57-1.75 (3H, m), 1.99-2.02 (1H, m), 2.71-2.83 (5H, m), 3.03-3.13 (4H, m), 6.96 (2H, d), 7.10-7.14 (1H, m), 7.31-7.35 (2H, m), 7.39 (1H, dd) |
| 58 | 1 + 34 | ESI+: 500.3 |
| 59 | 1 + 34 | ESI+: 401.3 |
| 60 | 60 | ESI+: 550.4 |
| 61 | 60 | ESI+: 566.4 |
| 62 | 60 | ESI+: 518.4 |
| 63 | 60 | ESI+: 550.4 |
| 64 | 60 | ESI+: 532.4 |
| 65 | 60 | ESI+: 514.2 |
| 66 | 60 | NMR CDCl3(400 MHz): 1.46 (9H, s), 2.89-3.10 (7H, m), 3.29-3.43 (2H, m), 3.75-3.88 (3H, m), 6.73 (1H, d), 7.05 (2H, d), 7.22-7.26 (1H, m), 7.40-7.44 (2H, m), 7.63 (1H, d) |
| 67 | 60 | NMR CDCl3(400 MHz): 1.46 (9H, s), 2.89-3.11 (7H, m), 3.28-3.44 (2H, m), 3.74-3.99 (3H, m), 6.73 (1H, d), 7.05 (2H, d), 7.23-7.26 (1H, m), 7.40-7.44 (2H, m), 7.63 (1H, d) |
| 68 | 68 | ESI-: 494.3 |

TABLE 6-4

| PEx | PSyn | DAT |
|---|---|---|
| 69 | 69 | ESI+: 511.4 |
| 70 | 70 | ESI+: 629.4 |

TABLE 6-4-continued

| PEx | PSyn | DAT |
|---|---|---|
| 71 | 71 | ESI+: 603.4 |
| 72 | 72 | ESI+: 443.2 |
| 73 | 73 | NMR CDCl3(400 MHz): 1.08-1.18 (2H, m), 1.62-1.87 (3H, m), 2.54-2.64 (2H, m), 2.72-2.78 (1H, m), 2.97-3.09 (2H, m), 3.19-3.29 (1H, m), 6.84-6.97 (2H, m), 7.08-7.14 (1H, m), 7.31-7.40 (3H, m) |
| 74 | 73 | NMR CDCl3(400 MHz): 1.03-1.06 (1H, m), 1.65-1.88 (4H, m), 2.58-2.69 (3H, m), 2.95-3.19 (3H, m), 5.21 (2H, s), 6.82 (1H, d), 7.32-7.41 (5H, m), 7.66 (1H, d) |
| 75 | 75 | NMR CDCl3(400 MHz): 1.14-1.28 (2H, m), 1.42-1.43 (9H, m), 1.59-1.88 (3H, m), 2.74-3.24 (6H, m), 4.45-4.56 (1H, m), 6.83-6.98 (2H, m), 7.08-7.15 (1H, m), 7.31-7.40 (3H, m) |
| 76 | 75 | NMR CDCl3(400 MHz): 1.08-1.10 (1H, m), 1.43 (9H, s), 1.65-1.88 (4H, m), 2.65-2.71 (1H, m), 2.90-3.11 (5H, m), 4.53 (1H, br s), 5.21 (2H, s), 6.83 (1H, d), 7.32-7.41 (5H, m), 7.66 (1H, d) |
| 77 | 77 | ESI+: 466.3 |
| 78 | 77 | ESI+: 498.4 |
| 79 | 77 | ESI+: 484.4 |
| 80 | 77 | ESI+: 500.2, 502.2 |
| 81 | 77 | ESI+: 500.4, 502.3 |
| 82 | 77 | ESI+: 491.4 |
| 83 | 77 | ESI+: 467.4 |
| 84 | 77 | ESI+: 443.4 |
| 85 | 77 | ESI+: 420.5 |
| 86 | 77 | ESI+: 530.3 |
| 87 | 77 | ESI+: 484.5 |
| 88 | 77 | ESI+: 452.3 |
| 89 | 77 | ESI+: 457.2 |
| 90 | 77 | ESI+: 421.4 |
| 91 | 77 | ESI+: 466.4 |
| 92 | 77 | ESI+: 385.4 |

TABLE 6-5

| PEx | PSyn | DAT |
|---|---|---|
| 93 | 77 | ESI+: 514.4, 516.4 |
| 94 | 77 | ESI+: 466.4 |
| 95 | 77 | ESI+: 577.4 |
| 96 | 77 | ESI+: 528.4 |
| 97 | 77 | ESI+: 470.4 |
| 98 | 77 | ESI+: 476.4 |
| 99 | 77 | ESI+: 466.4 |
| 100 | 77 | ESI+: 480.4 |
| 101 | 77 | ESI+: 430.3 |
| 102 | 77 | ESI+: 444.1 |
| 103 | 77 | ESI+: 458.3 |
| 104 | 77 | ESI+: 470.3 |
| 105 | 77 | ESI+: 470.3 |
| 106 | 77 | ESI+: 413.2 |
| 107 | 77 | ESI+: 464.2 |
| 108 | 77 | ESI+: 470.3 |
| 109 | 77 | ESI+: 484.4 |
| 110 | 77 | ESI+: 423.9 |
| 111 | 77 | ESI+: 502.2 |
| 112 | 77 | ESI+: 520.3 |
| 113 | 77 | NMR CDCl3(400 MHz): 0.53-0.58 (2H, m), 0.85-0.90 (2H, m), 1.50 (9H, s), 2.31 (2H, br s), 3.63 (2H, t), 3.76 (2H, br s), 4.00-4.06 (1H, m), 4.06 (2H, br s), 5.76 (1H, br s), 6.24 (1H, dd) |
| 114 | 77 | NMR CDCl3(400 MHz): 0.96-1.04 (1H, m), 1.43 (9H, s), 1.43-1.82 (4H, m), 2.69-2.74 (1H, m), 2.93-3.03 (5H, m), 4.31 (2H, br s), 4.57 (1H, br s), 6.33 (1H, dd), 6.92 (2H, d), 7.02 (1H, t), 7.28 (2H, t) |
| 115 | 77 | NMR CDCl3(400 MHz): 1.43 (9H, s), 2.67-2.98 (2H, m), 3.11-3.26 (3H, m), 3.52-3.96 (4H, m), 6.72-6.84 (3H, m), 6.95-7.04 (2H, m), 7.24-7.30 (2H, m) |
| 116 | 77 | NMR CDCl3(400 MHz): 1.44 (9H, s), 2.75 (1H, d), 2.83 (1H, d), 2.94 (3H, s), 3.04-3.16 (1H, m), 3.28-3.49 (2H, m), 3.70-4.00 (4H, m), 4.23 (2H, br s), 6.74-6.85 (2H, m), 6.90 (2H, d), 7.00-7.05 (1H, m), 7.26-7.30 (2H, m) |

TABLE 6-6

| PEx | PSyn | DAT |
|---|---|---|
| 117 | 77 | NMR CDCl3(400 MHz): 1.46 (9H, s), 2.69-3.00 (2H, m), 3.15-3.28 (3H, m), 3.48-3.98 (4H, m), 6.74-6.79 (2H, m), 6.84-6.86 (1H, m), 6.97-7.06 (2H, m), 7.26-7.32 (2H, m) |
| 118 | 77 | ESI+: 390.3 |
| 119 | 77 | NMR CDCl3(400 MHz): 1.44 (9H, s), 2.75 (1H, d), 2.84 (1H, d), 2.94 (3H, s), 3.02-3.17 (1H, m), 3.28-3.46 (2H, m), 3.67-3.99 (4H, m), 4.23 (2H, br s), 6.74-6.84 (2H, m), 6.90 (2H, d), 7.00-7.06 (1H, m), 7.28-7.30 (2H, m) |
| 120 | 77 | NMR CDCl3(400 MHz): 1.45 (9H, s), 1.64-1.69 (2H, m), 2.73-2.89 (2H, m), 2.96-3.17 (1H, m), 3.19-3.48 (3H, m), 3.63-4.00 (4H, m), 4.22 (1H, br s), 4.90 (1H, br s), 6.73-6.85 (2H, m), 6.88-6.94 (2H, m), 6.99-7.05 (1H, m), 7.28-7.33 (2H, m) |
| 121 | 77 | ESI+: 448.3 |
| 122 | 122 | ESI+: 467.4 |
| 123 | 123 | ESI+: 563.2 |
| 124 | 124 | ESI+: 655.3 |
| 125 | 124 | ESI+: 687.4 |
| 126 | 124 | ESI+: 695.4 |
| 127 | 124 | ESI+: 689.4 |
| 128 | 124 | ESI+: 711.4, 713.4 |
| 129 | 124 | ESI+: 702.4 |
| 130 | 124 | ESI+: 678.4 |
| 131 | 124 | ESI+: 632.4 |
| 132 | 124 | ESI+: 609.2 |
| 133 | 124 | ESI+: 697.5 |
| 134 | 124 | ESI+: 673.4 |
| 135 | 124 | ESI+: 641.3 |
| 136 | 124 | ESI+: 624.2 |
| 137 | 124 | ESI+: 588.2 |
| 138 | 124 | ESI+: 655.4 |
| 139 | 124 | ESI+: 574.4 |
| 140 | 124 | ESI+: 703.4 |
| 141 | 124 | ESI+: 655.4 |

TABLE 6-7

| PEx | PSyn | DAT |
|---|---|---|
| 142 | 124 | ESI+: 788.4 |
| 143 | 124 | ESI+: 717.4 |
| 144 | 124 | ESI+: 659.4 |
| 145 | 124 | ESI+: 665.3 |
| 146 | 124 | ESI+: 677.4 |
| 147 | 124 | ESI+: 669.4 |
| 148 | 124 | ESI+: 619.3 |
| 149 | 124 | ESI+: 633.3 |
| 150 | 124 | ESI+: 647.3 |
| 151 | 124 | ESI+: 659.3 |
| 152 | 124 | ESI+: 659.5 |
| 153 | 124 | ESI+: 602.3 |
| 154 | 124 | ESI+: 654.2 |
| 155 | 124 | ESI+: 659.3 |
| 156 | 124 | ESI+: 673.3 |
| 157 | 124 | ESI+: 669.3 |
| 158 | 124 | ESI−: 689.2 |
| 159 | 124 | ESI−: 752.3 |
| 160 | 124 | ESI−: 707.1 |
| 161 | 124 | ESI+: 578.3 |
| 162 | 124 | ESI+: 623.3 |
| 163 | 124 | ESI+: 679.3 |
| 164 | 124 | ESI+: 693.3 |
| 165 | 124 | ESI+: 679.3 |
| 166 | 124 | ESI+: 601.1 |
| 167 | 124 | ESI+: 693.2 |
| 168 | 124 | ESI+: 693.2 |
| 169 | 124 | NMR CDCl3(400 MHz): 1.18-1.31 (1H, m), 1.31 (9H, br s), 1.96-2.31 (4H, m), 2.75 (3H, s), 2.93-3.30 (6H, m), 6.95 (2H, d), 7.07 (1H, t), 7.31 (2H, t), 7.90-7.98 (1H, m), 8.37-8.40 (1H, m), 8.47 (1H, s), 9.40 (1H, br s), 9.80-9.85 (1H, m), 10.88 (1H, br s) |

TABLE 6-7-continued

| PEx | PSyn | DAT |
|---|---|---|
| 170 | 77 + 124 | ESI+: 673.4 |
| 171 | 77 + 124 | ESI+: 687.4 |
| 172 | 172 | ESI+: 560.2 |

TABLE 6-8

| PEx | PSyn | DAT |
|---|---|---|
| 173 | 173 | ESI+: 558.2 |
| 174 | 174 | ESI+: 732.9 |
| 175 | 175 | ESI+: 661.3 |
| 176 | 176 | ESI+: 524.2 |
| 177 | 176 | ESI+: 488.1 |
| 178 | 176 | ESI+: 452.3 |
| 179 | 176 | ESI+: 666.4 |
| 180 | 176 | ESI+: 652.3 |
| 181 | 176 | ESI+: 456.2 |
| 182 | 182 | ESI+: 740.3 |
| 183 | 182 | ESI+: 740.3 |
| 184 | 182 | ESI+: 758.1 |
| 185 | 185 | ESI+: 754.3 |
| 186 | 185 | ESI+: 754.4 |
| 187 | 185 | ESI+: 772.4 |
| 188 | 185 | ESI+: 786.3 |
| 189 | 185 | ESI+: 816.4 |
| 190 | 190 | ESI+: 680.3 |
| 191 | 190 | ESI+: 666.4 |

TABLE 6-9

| PEx | PSyn | DAT |
|---|---|---|
| 192 | 192 | NMR DMSO-d6 (400 MHz): 7.00 (1H, d), 7.57-7.64 (5H, m), 7.97 (1H, d) |
| 193 | 193 | NMR DMSO-d6 (400 MHz): 3.52 (3H, s), 7.61 (1H, t), 8.55-8.61 (1H, m) |
| 194 | 194 | ESI+: 275.3 |
| 195 | 195 | NMR DMSO-d6 (400 MHz): 7.60 (2H, t), 7.67 (1H, d), 7.75-7.81 (3H, m), 8.58 (1H, t) |
| 196-1 | 196 | NMR CDCl3 (400 MHz): 1.09 (9H, s), 1.61-1.70 (1H, m), 1.75-1.84 (1H, m), 3.47-3.54 (1H, m), 3.69-3.80 (2H, m), 4.01-4.07 (2H, m), 4.84-4.87 (1H, m), 6.00-6.01 (1H, m), 7.37-7.46 (6H, m), 7.67-7.74 (4H, m) |
| 196-2 | 196 | NMR CDCl3 (400 MHz): 1.00 (9H, s), 1.60-1.69 (2H, m), 3.37-3.43 (1H, m), 3.95-4.20 (4H, m), 4.81 (1H, br s), 6.43 (1H, br s), 7.37-7.46 (6H, m), 7.64-7.76 (4H, m) |
| 197 | 197 | ESI+: 143.1 |
| 198 | 197 | ESI+: 143.1 |
| 199 | 1 | NMR CDCl3 (400 MHz): 3.46 (3H, s), 6.75 (1H, dd), 7.16 (2H, d), 7.36 (1H, t), 7.51 (2H, t), 8.18 (1H, t) |
| 200 | 1 | NMR CDCl3 (400 MHz): 0.80-0.91 (4H, m), 2.29 (3H, s), 3.80-3.84 (1H, m), 7.20 (1H, d), 7.79 (1H, d) |
| 201 | 1 | NMR CDCl3 (400 MHz): 2.47 (3H, s), 6.73 (1H, d), 7.00-7.02 (2H, m), 7.20-7.24 (1H, m), 7.39-7.43 (2H, m), 7.65 (1H, d) |
| 202 | 1 | NMR CDCl3 (400 MHz): 0.83-0.97 (4H, m), 3.87-3.92 (1H, m), 7.48 (1H, m), 7.79 (1H, d) |
| 203 | 34 | ESI+: 535.1 |
| 204 | 34 | ESI+: 449.9 |
| 205 | 34 | ESI+: 384.1 |
| 206 | 34 | ESI+: 506.3 |
| 207 | 34 | ESI+: 530.0 |
| 208 | 34 | ESI+: 424.2 |
| 209 | 34 | ESI+: 424.3 |
| 210 | 34 | ESI+: 406.3 |
| 211 | 34 | ESI+: 442.4 |
| 212 | 34 | ESI+: 388.2 |

TABLE 6-10

| PEx | PSyn | DAT |
|---|---|---|
| 213 | 34 | NMR CDCl3 (400 MHz): 1.49 (9H, s), 2.33 (3H, s), 2.88-3.44 (5H, m), 3.80-4.32 (4H, m), 6.61 (1H, d) 6.99 (2H, d), 7.14-7.22 (1H, m), 7.31-7.52 (3H, m) |
| 214 | 1 | ESI+: 508.2 |
| 215 | 1 | ESI+: 458.6 |
| 216 | 216 | NMR CDCl3 (400 MHz): 1.79-1.84 (1H, m), 2.47-2.57 (4H, m), 2.96-2.99 (1H, m), 3.07-3.18 (3H, m), 3.32-3.39 (2H, m), 5.04-5.09 (1H, m), 6.70 (1H, d), 7.04 (2H, d), 7.23 (1H, t), 7.39-7.46 (4H, m), 7.54-7.58 (1H, m), 7.60 (1H, d), 8.03 (2H, d) |
| 217 | 216 | NMR CDCl3 (400 MHz): 1.98-2.05 (1H, m), 2.17-2.26 (1H, m), 2.39-2.50 (3H, m), 3.06-3.14 (2H, m), 3.23-3.34 (2H, m), 3.39-3.44 (2H, m), 5.45-5.49 (1H, m), 6.71 (1H, d), 7.04 (2H, d), 7.23 (1H, t), 7.39-7.46 (4H, m), 7.54-7.59 (2H, m), 8.06 (2H, d) |
| 218 | 34 | ESI+: 424.3 |
| 219 | 34 | NMR CDCl3 (400 MHz): 1.70-1.78 (1H, m), 2.05-2.26 (3H, m), 2.32-2.37 (1H, m), 3.00-3.04 (2H, m), 3.19-3.23 (2H, m), 3.29-3.35 (2H, m), 4.16-4.19 (1H, m), 6.71 (1H, d), 7.05 (2H, d), 7.23 (1H, t), 7.39-7.44 (4H, m), 7.60 (1H, d) |
| 220 | 220 | ESI+: 468.1 |
| 221 | 221 | ESI+: 553.3 |
| 222 | 221 | ESI+: 553.2 |
| 223 | 221 | ESI+: 553.2 |
| 224 | 221 | ESI+: 553.3 |
| 225 | 221 | ESI+: 517.3 |
| 226 | 68 | NMR CDCl3 (400 MHz): 1.48-1.51 (9H, m), 2.27 (3H, s), 2.93-3.16 (1H, m), 3.18-3.63 (4H, m), 3.85-4.13 (1H, m), 4.68-4.90 (1H, m), 6.61 (1H, d), 6.95-7.04 (2H, m), 7.15-7.22 (1H, m), 7.32-7.43 (2H, m), 7.48 (1H, d), 9.68-9.70 (1H, m) |
| 227 | 69 | NMR CDCl3 (400 MHz): 1.45-1.48 (9H, m), 2.25 (3H, s), 2.32 (3H, s), 2.71-3.65 (7H, m), 3.80-4.75 (2H, m), 6.53-6.66 (1H, m), 6.91-7.04 (2H, m), 7.13-7.21 (1H, m), 7.32-7.49 (3H, m) |

TABLE 6-11

| PEx | PSyn | DAT |
|---|---|---|
| 228 | 70 | ESI+: 575.5 |
| 229 | 73 | ESI+: 423.3 |
| 230 | 73 | ESI+: 423.2 |
| 231 | 73 | ESI+: 423.3 |
| 232 | 73 | ESI+: 387.3 |
| 233 | 75 | ESI+: 523.4 |
| 234 | 75 | ESI+: 523.3 |
| 235 | 75 | ESI+: 523.4 |
| 236 | 75 | ESI+: 487.3 |
| 237 | 60 | ESI+: 537.3 |
| 238 | 60 | ESI+: 501.4 |
| 239 | 30 | NMR CDCl3 (400 MHz): 2.30-2.31 (3H, m), 2.74-3.51 (12H, m), 6.59 (1H, d), 6.95-7.03 (2H, m), 7.14-7.22 (1H, m), 7.34-7.52 (3H, m) |
| 240 | 190 | NMR CDCl3 (400 MHz): 2.29-2.30 (3H, m), 2.41-2.57 (4H, m), 2.61-2.74 (1H, m), 2.82-3.34 (9H, m), 3.67-4.05 (1H, m), 6.59 (1H, d), 6.97-7.03 (2H, m), 7.15-7.21 (1H, m), 7.35-7.46 (3H, m) |
| 241 | 77 | ESI+: 504.5 |
| 242 | 77 | ESI+: 438.1 |
| 243 | 77 | ESI+: 428.9 |
| 244 | 77 | — |
| 245 | 77 | ESI+: 477.5 |
| 246 | 77 | ESI+: 523.3 |
| 247 | 77 | ESI+: 523.3 |
| 248 | 77 | ESI+: 376.4 |
| 249 | 77 | ESI+: 412.3 |
| 250 | 77 | ESI+: 507.4 |
| 251 | 77 | ESI+: 493.4 |
| 252 | 77 | ESI+: 493.4 |
| 253 | 77 | ESI+: 457.4 |
| 254 | 77 | ESI+: 471.4 |

TABLE 6-12

| PEx | PSyn | DAT |
|---|---|---|
| 255 | 77 | NMR CDCl3 (400 MHz): 2.18 (3H, s), 2.40-2.66 (5H, m), 2.84-3.03 (3H, m), 3.18 (3H, s), 3.28-3.34 (1H, m), 3.39-3.82 (2H, m), 3.88-4.01 (1H, m), 6.59 (1H, d), 6.70 (1H, d), 6.83 (2H, d), 6.94-7.01 (1H, m), 7.22-7.34 (2H, m) |
| 256 | 124 | ESI+: 695.1 |
| 257 | 124 | ESI+: 627.2 |
| 258 | 124 | ESI+: 615.2 |
| 259 | 124 | ESI+: 665.1 |
| 260 | 124 | ESI+: 667.1 |
| 261 | 124 | ESI+: 712.3 |
| 262 | 124 | ESI+: 712.5 |
| 263 | 124 | ESI+: 565.4 |
| 264 | 124 | ESI+: 601.5 |
| 265 | 124 | ESI+: 696.3 |
| 266 | 124 | ESI+: 682.4 |
| 267 | 124 | ESI+: 682.4 |
| 268 | 124 | ESI+: 646.5 |
| 269 | 124 | ESI+: 660.5 |
| 270 | 124 | NMR CDCl3 (400 MHz): 2.32 (3H, s), 2.59-3.89 (14H, m), 3.96-4.18 (1H, m), 6.88-6.96 (3H, m), 7.03-7.10 (1H, m), 7.28-7.37 (2H, m), 7.97 (1H, dd), 8.43 (1H, d), 8.45 (1H, s), 9.42-9.48 (1H, m), 9.88-9.95 (1H, m), 10.53 (1H, br s) |
| 271 | 271 | ESI+: 725.3 |
| 272 | 272 | ESI+: 725.2 |

TABLE 7-1

| Ex | Str |
|---|---|
| 1 | 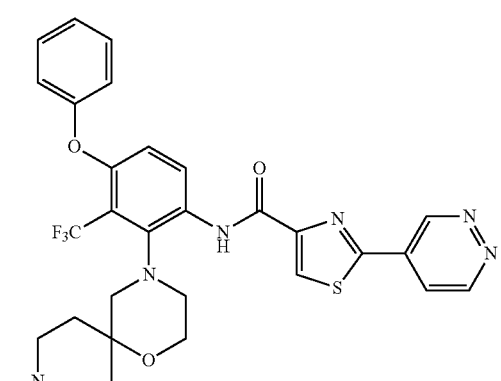 |
| 2 | 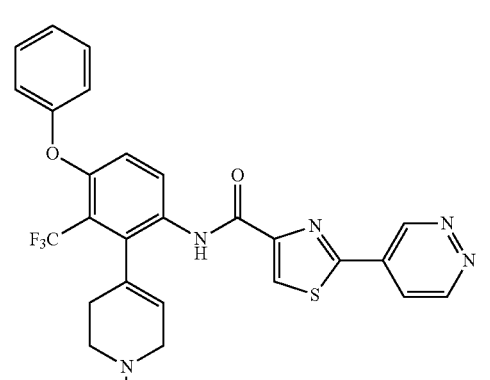 |

TABLE 7-1-continued
| Ex | Str |
|---|---|
| 3 | 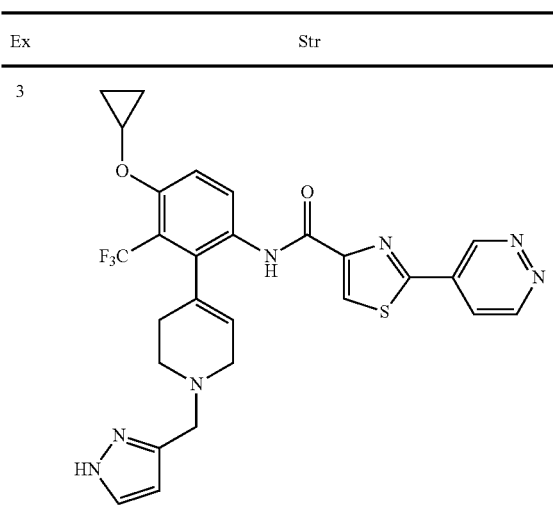 |
| 4 | 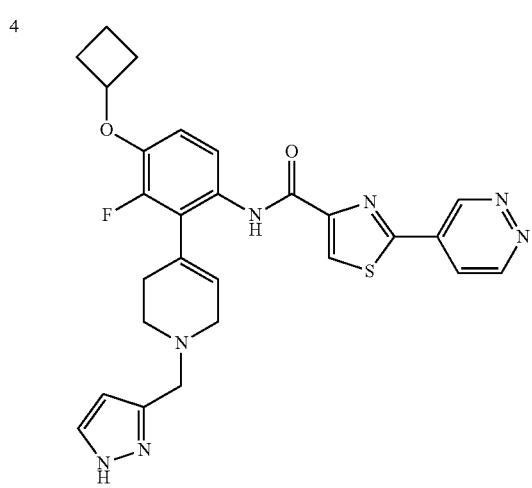 |
| 5 | 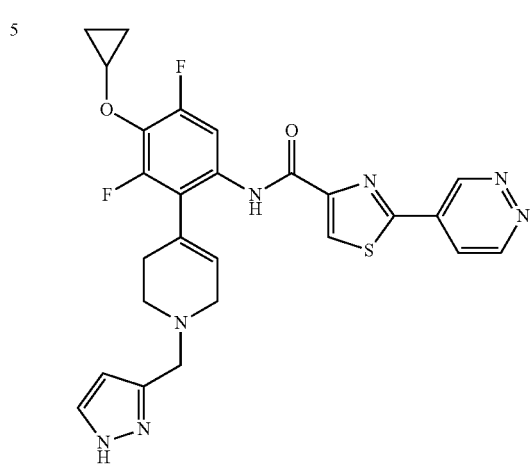 |
| 6 | 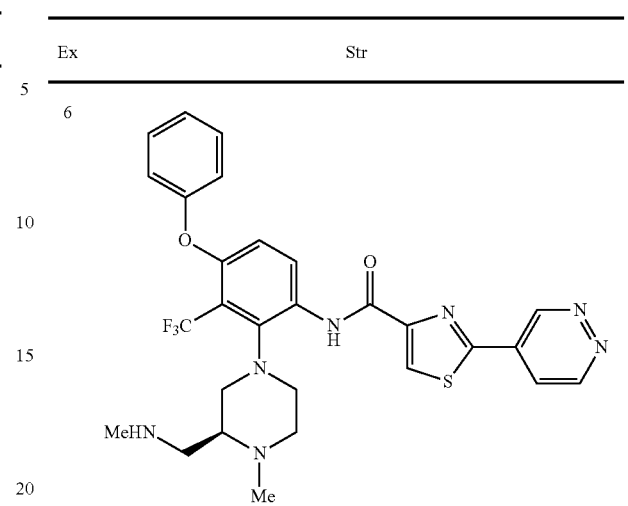 |
| 7 | 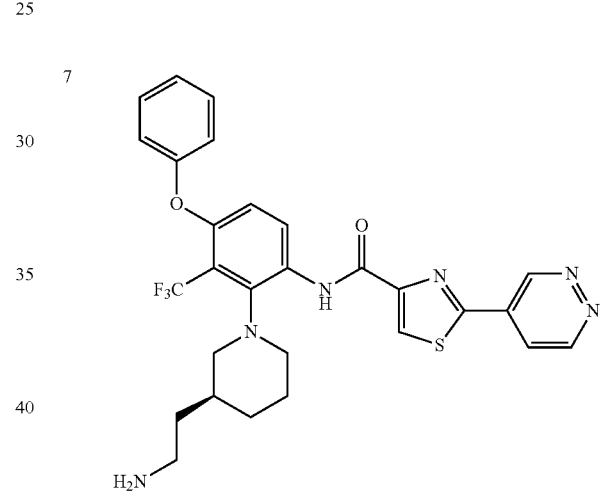 |
| 8 | 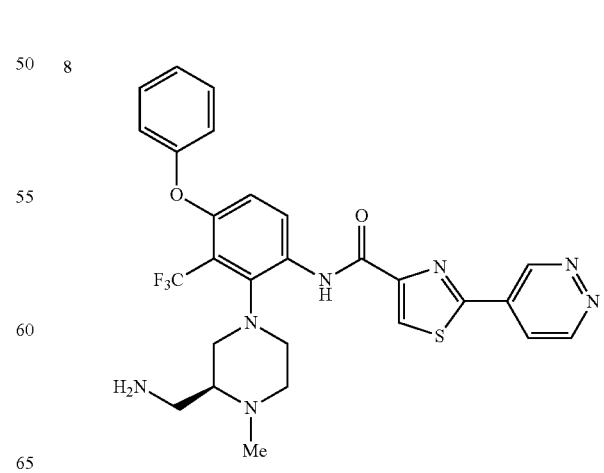 |

TABLE 7-2
| Ex | Str |
|---|---|
| 9 | 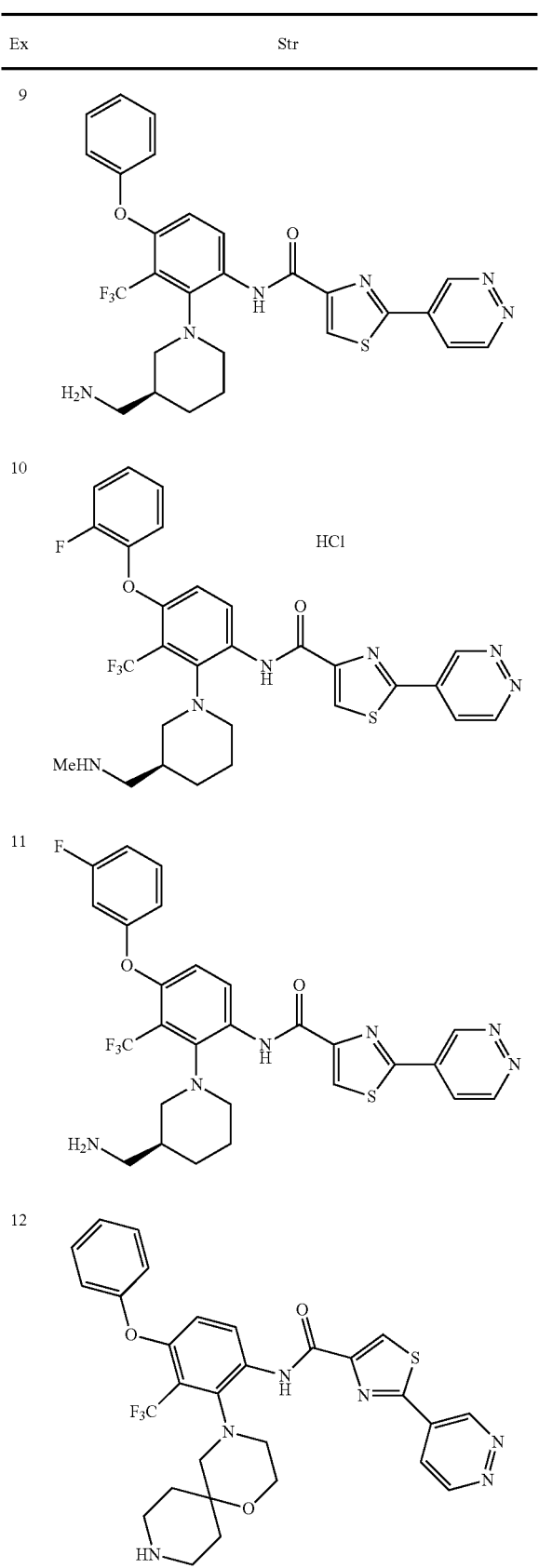 |
| 10 | |
| 11 | |
| 12 | |
TABLE 7-2-continued
| Ex | Str |
|---|---|
| 13 | 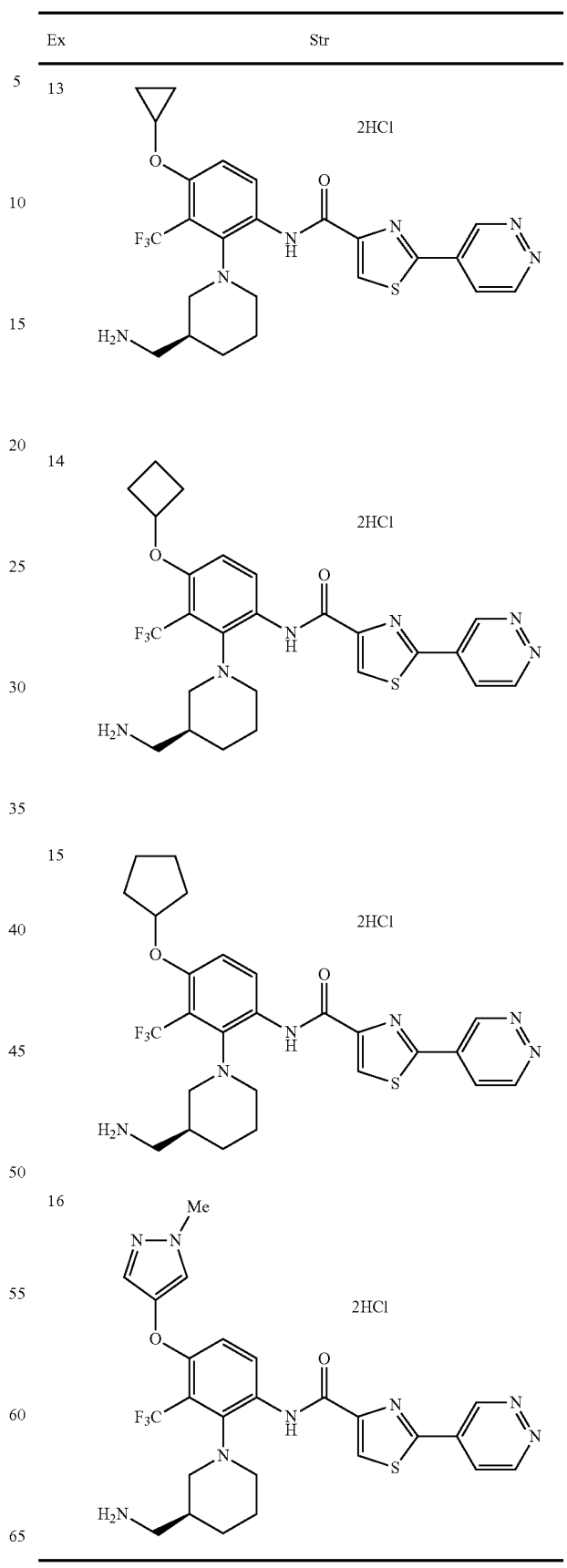 |
| 14 | |
| 15 | |
| 16 | |

TABLE 7-3
| Ex | Str |
|---|---|
| 17 | 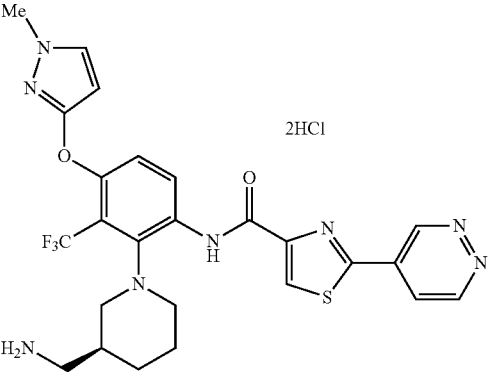 [SMILES: Cn1ccc(Oc2ccc(NC(=O)c3csc(-c4ccnnc4)n3)c(N3CCC[C@@H](CN)C3)c2C(F)(F)F)n1] 2HCl |
| 18 | 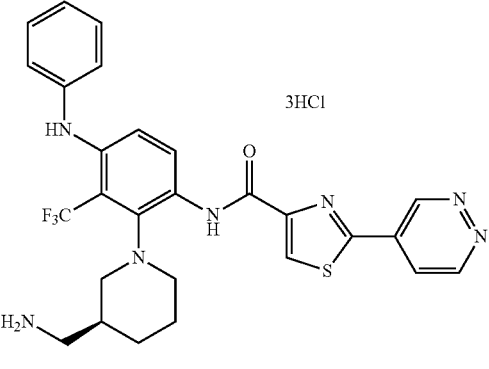 [SMILES: NC[C@@H]1CCCN(c2c(NC(=O)c3csc(-c4ccnnc4)n3)ccc(Nc3ccccc3)c2C(F)(F)F)C1] 3HCl |
| 19 | 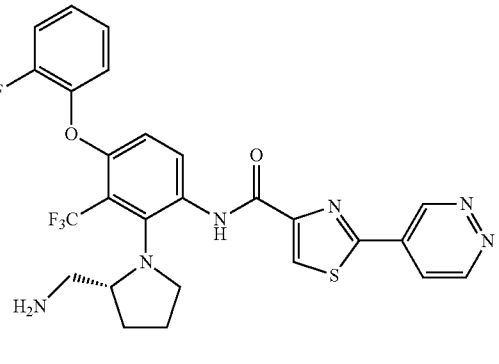 |
| 20 | 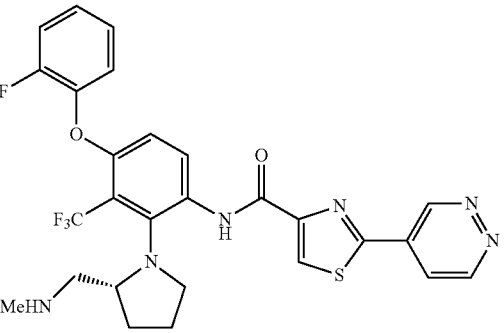 |
TABLE 7-3-continued
| Ex | Str |
|---|---|
| 21 | 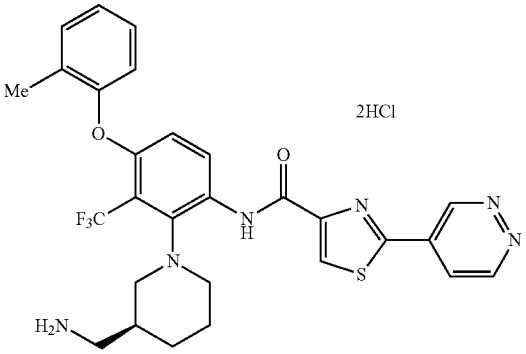 [SMILES: Cc1ccccc1Oc1ccc(NC(=O)c2csc(-c3ccnnc3)n2)c(N2CCC[C@@H](CN)C2)c1C(F)(F)F] 2HCl |
| 22 | 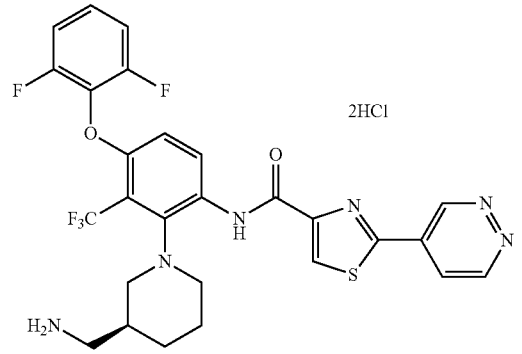 [SMILES: NC[C@@H]1CCCN(c2c(NC(=O)c3csc(-c4ccnnc4)n3)ccc(Oc3c(F)cccc3F)c2C(F)(F)F)C1] 2HCl |
| 23 | 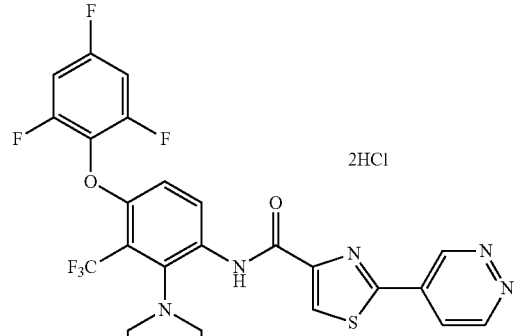 2HCl |
| 24 | 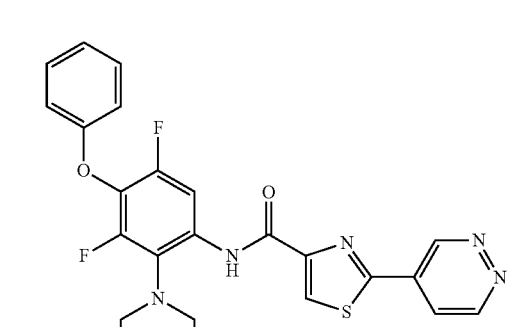 |

TABLE 7-4
| Ex | Str |
|---|---|
| 25 | |
| 26 | |
| 27 | |
| 28 | |
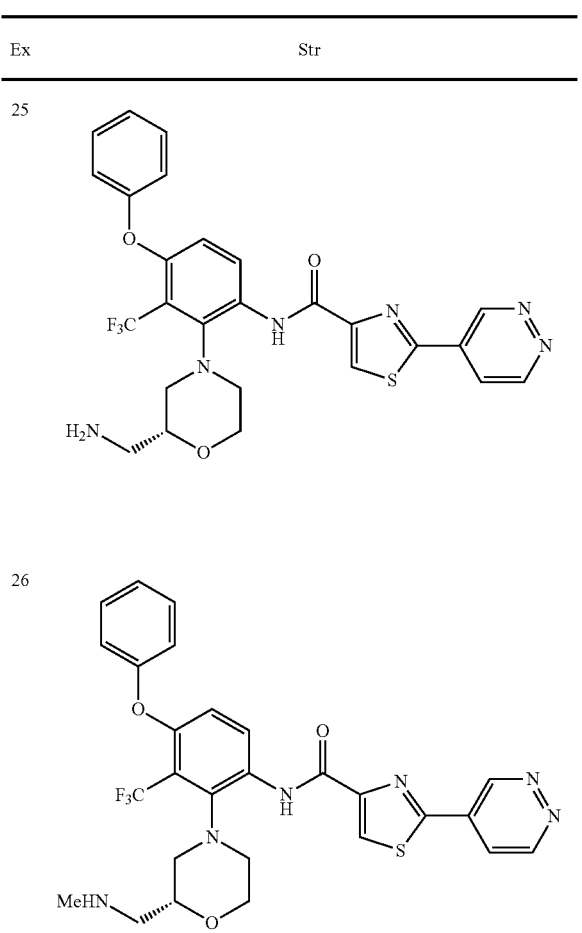
TABLE 7-4-continued
| Ex | Str |
|---|---|
| 29 | |
| 30 | |
| 31 | |
| 32 | |
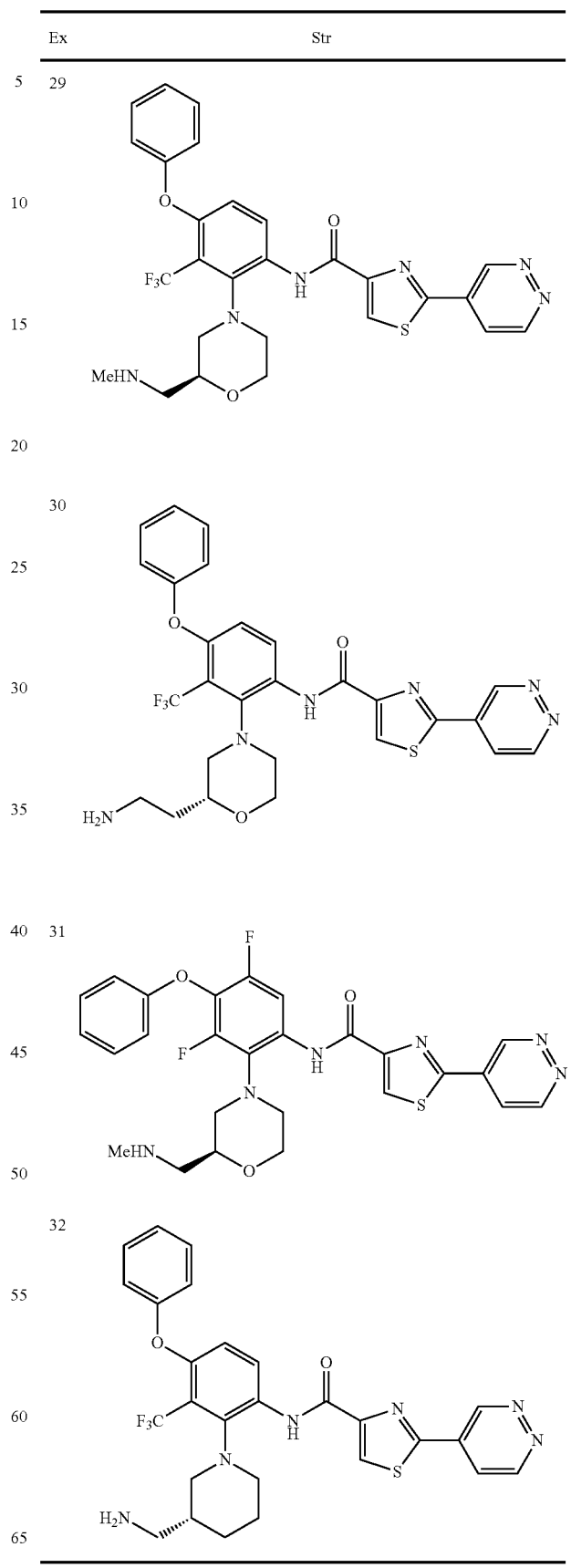

TABLE 7-5
| Ex | Str |
|---|---|
| 33 | 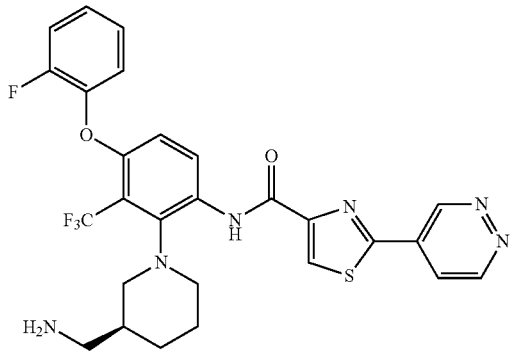 [SMILES: NC[C@@H]1CCCN(c2c(NC(=O)c3csc(-c4ccnnc4)n3)ccc(Oc3ccccc3F)c2C(F)(F)F)C1] |
| 34 | 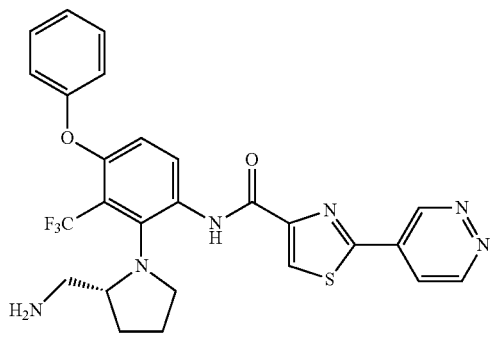 [SMILES: NC[C@H]1CCCN1c1c(NC(=O)c2csc(-c3ccnnc3)n2)ccc(Oc2ccccc2)c1C(F)(F)F] |
| 35 | 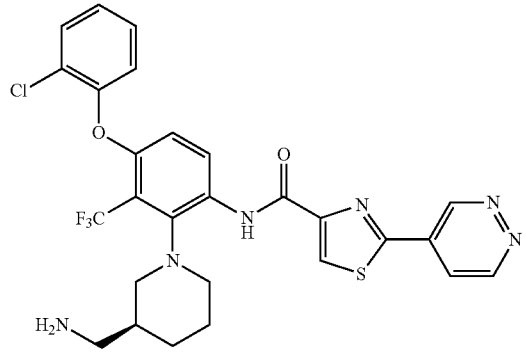 [SMILES: NC[C@@H]1CCCN(c2c(NC(=O)c3csc(-c4ccnnc4)n3)ccc(Oc3ccccc3Cl)c2C(F)(F)F)C1] |
| 36 | 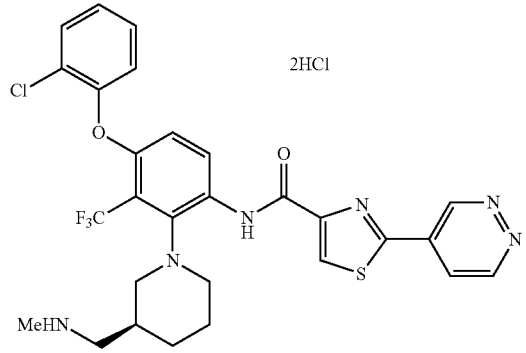 [SMILES: CNC[C@@H]1CCCN(c2c(NC(=O)c3csc(-c4ccnnc4)n3)ccc(Oc3ccccc3Cl)c2C(F)(F)F)C1] |
TABLE 7-5-continued
| Ex | Str |
|---|---|
| 37 | 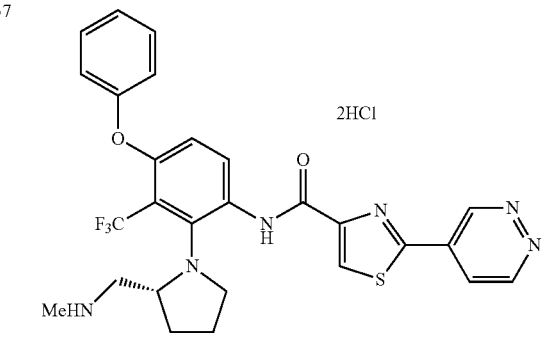 |
| 38 | |
| 39 | |
| 40 | |

TABLE 7-6
| Ex | Str |
|---|---|
| 41 | 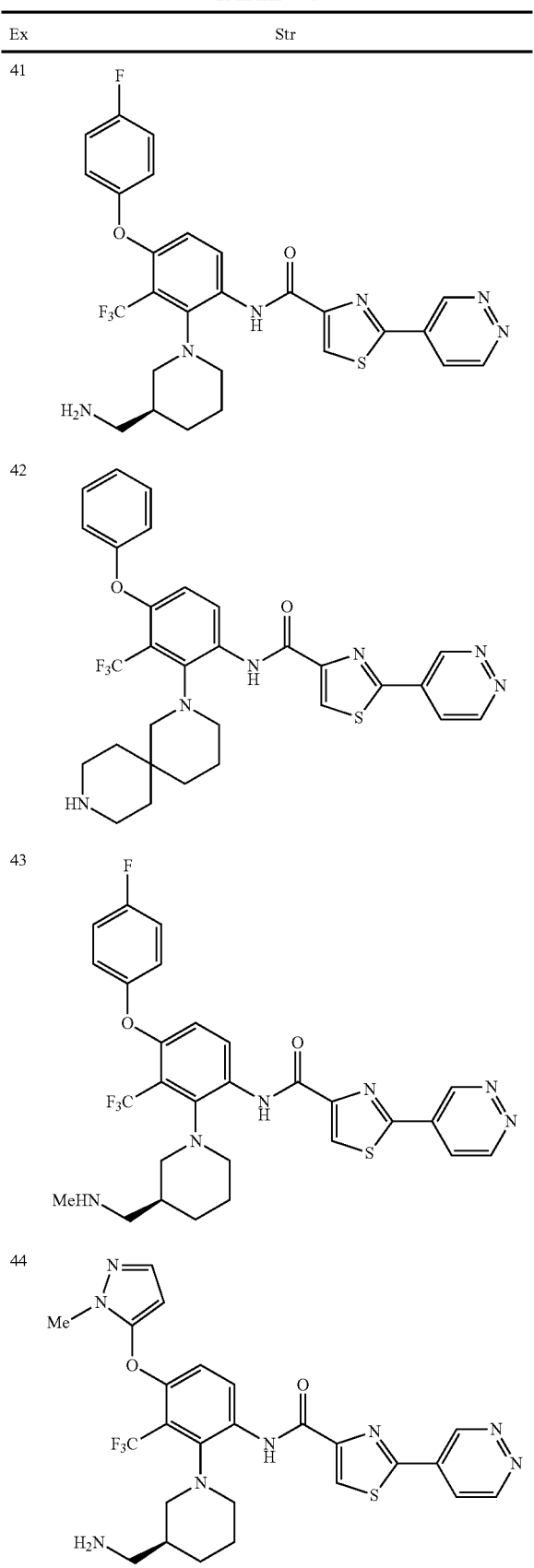 |
| 42 | |
| 43 | |
| 44 | |
TABLE 7-6-continued
| Ex | Str |
|---|---|
| 45 | 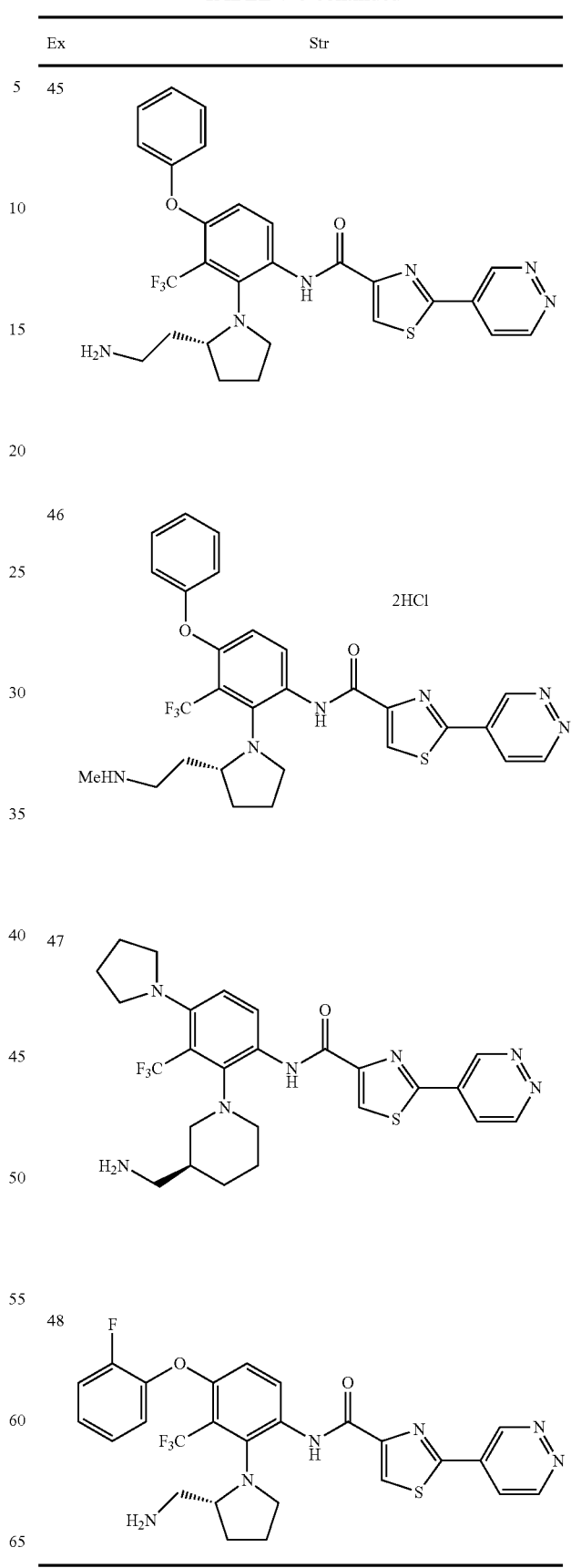 |
| 46 | |
| 47 | |
| 48 | |

TABLE 7-7
| Ex | Str |
|---|---|
| 49 | 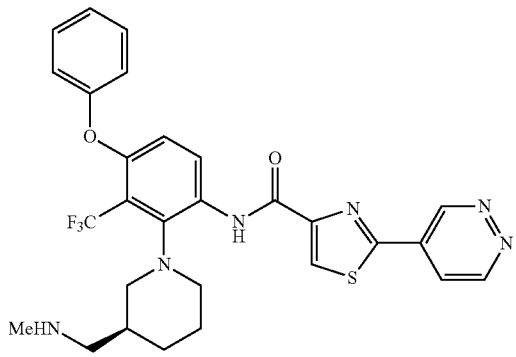 [SMILES: CNC[C@@H]1CCCN(c2c(NC(=O)c3csc(-c4ccnnc4)n3)ccc(Oc3ccccc3)c2C(F)(F)F)C1] |
| 50 | 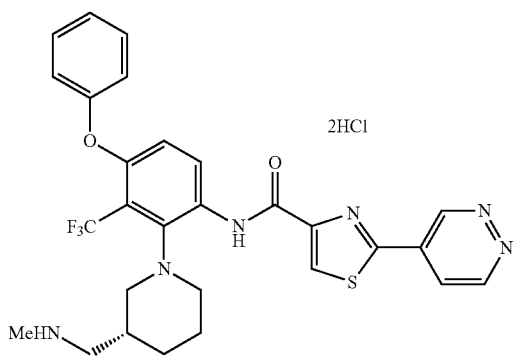 [SMILES: CNC[C@H]1CCCN(c2c(NC(=O)c3csc(-c4ccnnc4)n3)ccc(Oc3ccccc3)c2C(F)(F)F)C1] |
| 51 | 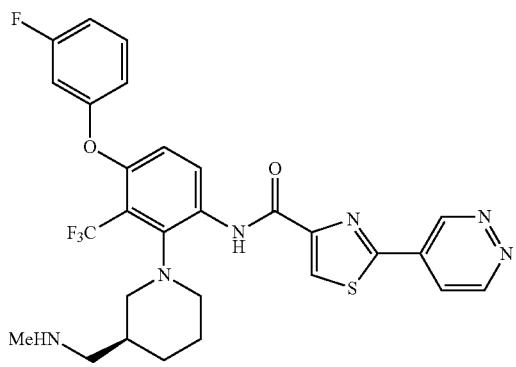 [SMILES: CNC[C@@H]1CCCN(c2c(NC(=O)c3csc(-c4ccnnc4)n3)ccc(Oc3cccc(F)c3)c2C(F)(F)F)C1] |
| 52 | 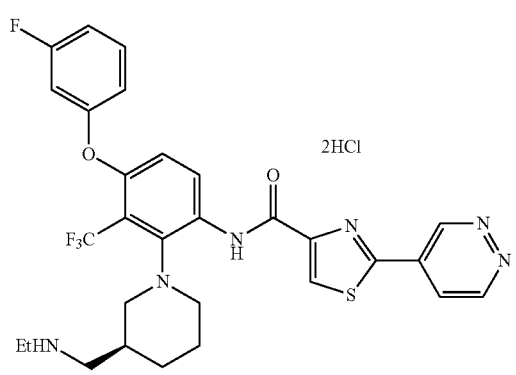 |

TABLE 7-7-continued

| Ex | Str |
|---|---|
| 53 | (structure: 3-fluorophenoxy-trifluoromethyl-phenyl with piperidine bearing CH2-NH-CH2CH2-OMe, linked via NH-C(=O)- to thiazole-pyridazine; 2HCl) |
| 54 | (structure: phenoxy-trifluoromethyl-phenyl with piperidine bearing CH2-NMe2, linked via NH-C(=O)- to thiazole-pyridazine; 2HCl) |
| 55 | (structure: phenoxy-trifluoromethyl-phenyl with piperidine bearing CH2-NMe2 (opposite stereochemistry), linked via NH-C(=O)- to thiazole-pyridazine; 2HCl) |
| 56 | (structure: phenoxy-trifluoromethyl-phenyl with morpholine bearing CH2-NMe2, linked via NH-C(=O)- to thiazole-pyridazine) |

TABLE 7-8

| Ex | Str |
|---|---|
| 57 | (structure) |
| 58 | (structure) |
| 59 | (structure) |
| 60 | (structure) |

TABLE 7-8-continued
| Ex | Str |
|---|---|
| 61 | 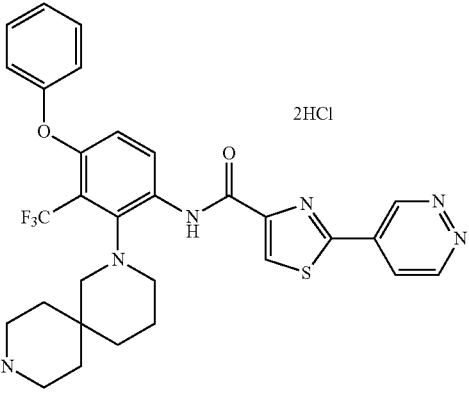 |
| 62 | 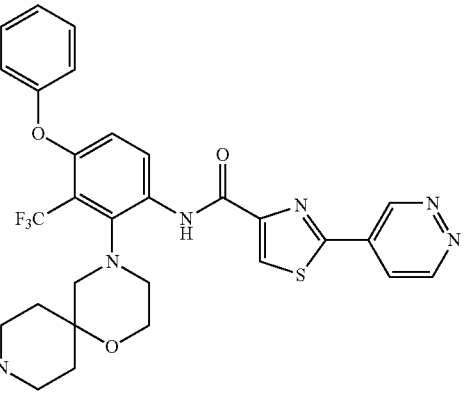 |
| 63 | 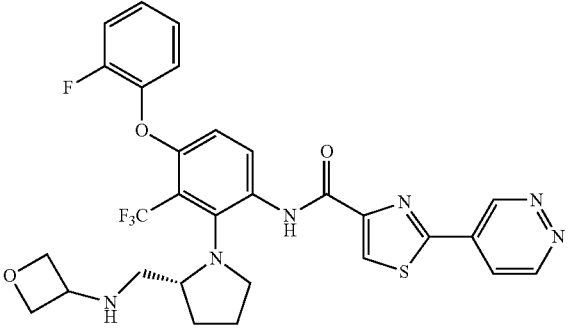 [SMILES: O=C(Nc1ccc(Oc2ccccc2F)c(C(F)(F)F)c1N1CCC[C@@H]1CNC1COC1)c1csc(-c2ccnnc2)n1] |
| 64 | 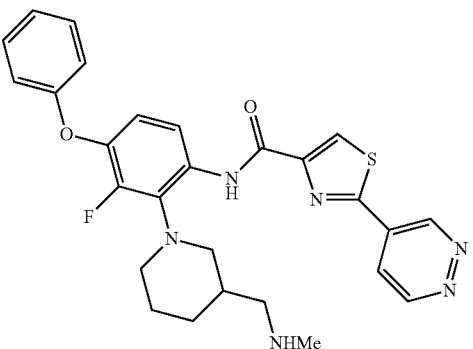 [SMILES: CNCC1CCCN(c2c(NC(=O)c3csc(-c4ccnnc4)n3)ccc(Oc3ccccc3)c2F)C1] |

TABLE 7-9
| Ex | Str |
|---|---|
| 65 | 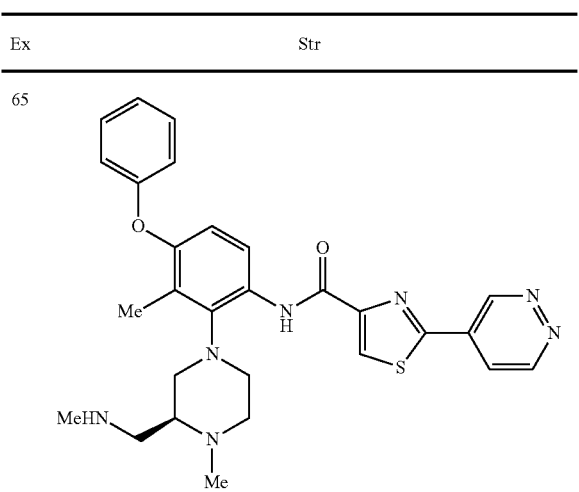 |
| 66 | |
| 67 | |
| 68 | |
TABLE 7-9-continued
| Ex | Str |
|---|---|
| 69 | 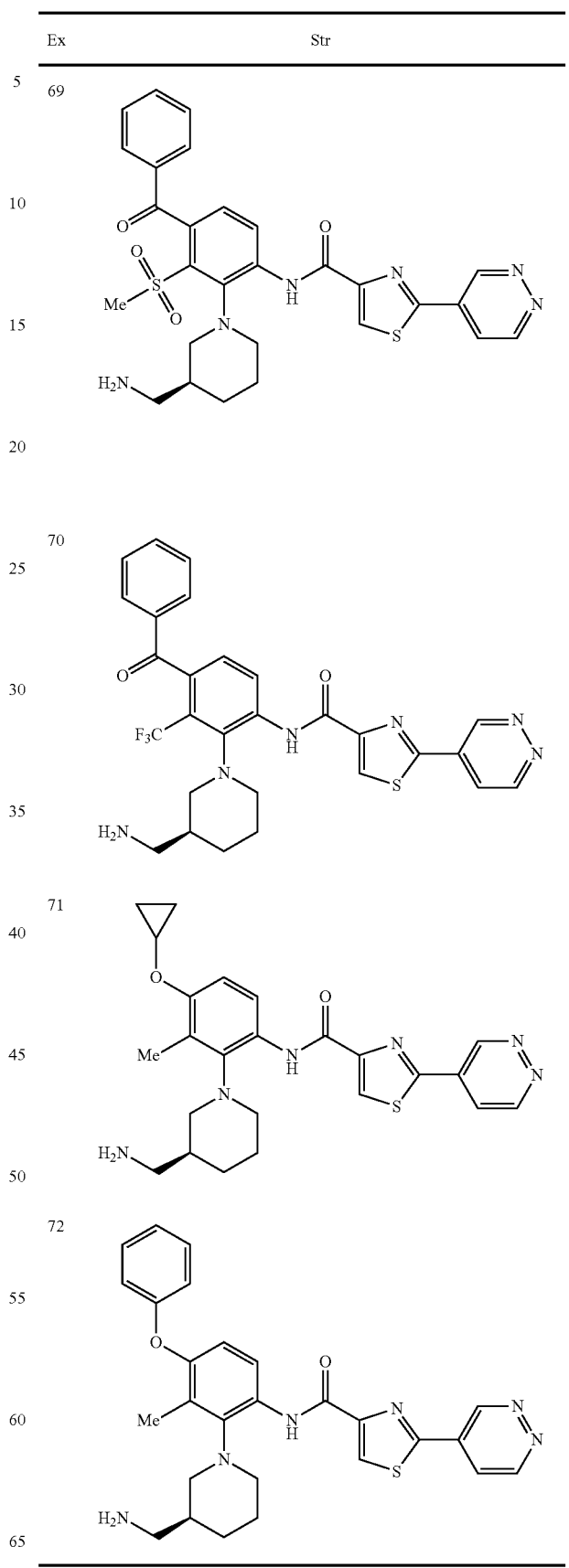 |
| 70 | |
| 71 | |
| 72 | |

TABLE 7-10
| Ex | Str |
|---|---|
| 73 | 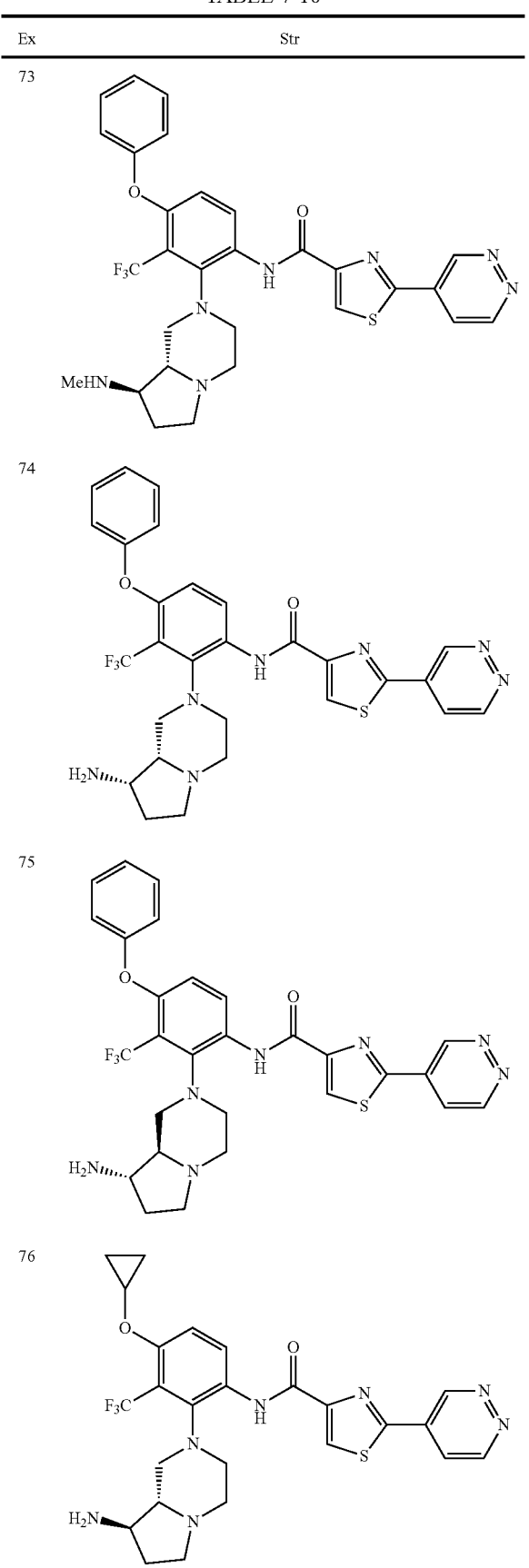 |
| 74 | |
| 75 | |
| 76 | |
TABLE 7-10-continued
| Ex | Str |
|---|---|
| 77 | 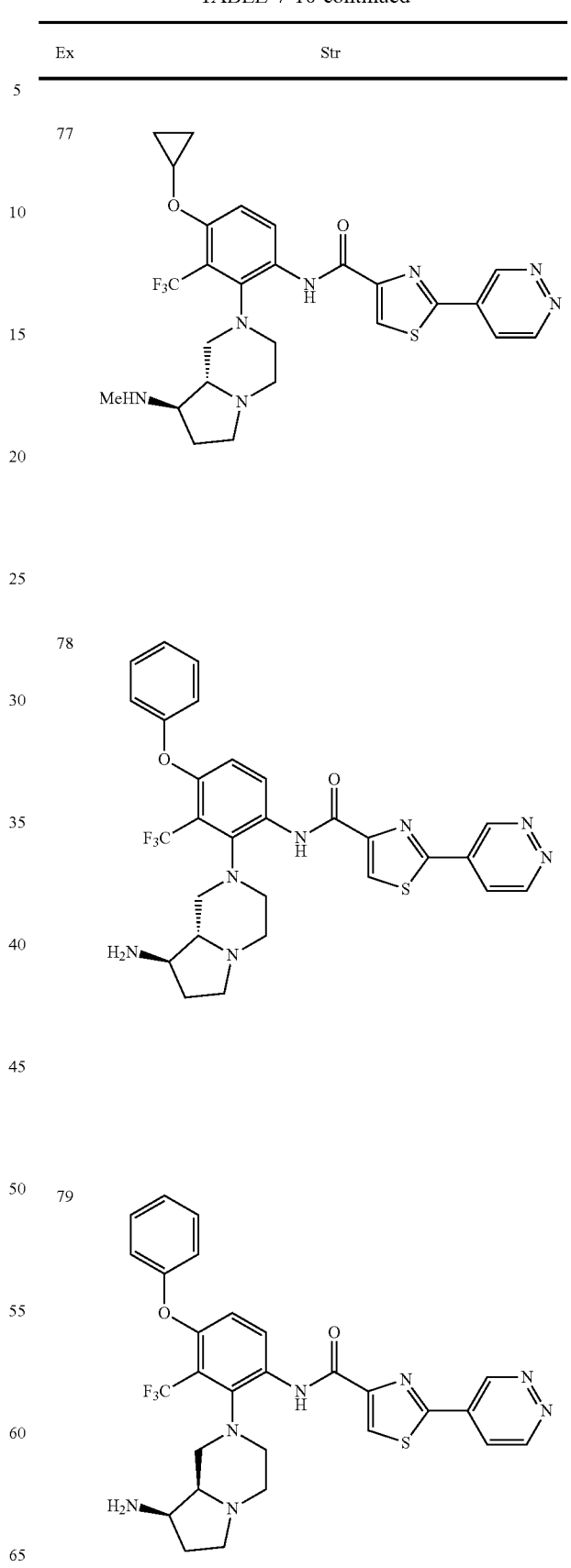 |
| 78 | |
| 79 | |

TABLE 7-10-continued

| Ex | Str |
|---|---|
| 80 | (structure) |

TABLE 7-11

| Ex | Str |
|---|---|
| 81 | (structure) |
| 82 | (structure) |

TABLE 7-11-continued

| Ex | Str |
|---|---|
| 83 | (structure) |
| 84 | (structure) |
| 85 | (structure) |
| 86 | (structure) |

TABLE 7-11-continued

| Ex | Str |
|---|---|
| 87 | (structure: phenoxy-trifluoromethyl-phenyl with pyrrolidinyl-CH2NH2 substituent, N-H amide linked to thiazole, with fumaric acid co-former) |

TABLE 8-1

| Ex | Syn | DAT |
|---|---|---|
| 1 | 1 | ESI+: 611.4 |
| 2 | 1 | ESI+: 604.2 |
| 3 | 1 | ESI+: 568.1 |
| 4 | 1 | ESI+: 532.3 |
| 5 | 1 | ESI+: 536.2 |
| 6 | 6 | ESI+: 584.2 |
| 7 | 6 | ESI+: 569.4 |
| 8 | 6 | ESI+: 570.4 |
| 9 | 9 | ESI+: 555.3 |
|  |  | NMR DMSO-d6(500 MHz): 1.03-1.24 (1H, m), 1.69-1.89 (1H, m), 1.96-2.16 (3H, m), 2.37-2.59 (2H, m), 2.72 (1H, t), 2.92-3.07 (2H, m), 3.12-3.22 (1H, m), 6.93-7.44 (6H, m), 8.19-8.86 (3H, m), 9.47-10.63 (3H, m) |
| 10 | 9 | ESI+: 587.4 |
|  |  | NMR DMSO-d6(500 MHz): 1.09-1.29 (1H, m), 1.61-2.12 (3H, m), 2.37-2.47 (4H, m), 2.65-2.90 (3H, m), 2.99-3.04 (2H, m), 3.22-3.30 (1H, m), 6.98-7.45 (5H, m), 8.16-8.91 (5H, m), 9.52-10.50 (3H, m) |
| 11 | 9 | ESI+: 573.4 |
|  |  | NMR DMSO-d6(500 MHz): 1.02-1.16 (1H, m), 1.70-2.16 (4H, m), 2.34-2.76 (3H, m), 2.94-3.06 (2H, m), 3.11-3.20 (1H, m), 6.74-7.46 (5H, m), 8.19-8.90 (3H, m), 9.46-10.70 (3H, m) |
| 12 | 9 | ESI+: 597.3 |
| 13 | 9 | ESI+: 519.3 |
| 14 | 9 | ESI+: 533.4 |
| 15 | 9 | ESI+: 547.4 |
| 16 | 9 | ESI+: 559.3 |
| 17 | 9 | ESI+: 559.3 |
| 18 | 9 | ESI+: 554.2 |
| 19 | 9 | ESI+: 559.2 |
| 20 | 9 | ESI+: 573.3 |
| 21 | 9 | ESI+: 569.4 |
| 22 | 9 | ESI+: 591.3 |
| 23 | 9 | ESI+: 609.4 |

TABLE 8-2

| Ex | Syn | DAT |
|---|---|---|
| 24 | 9 | ESI+: 523.4 |
| 25 | 9 | ESI+: 557.4 |
| 26 | 9 | ESI+: 571.4 |
| 27 | 9 | ESI+: 557.4 |
| 28 | 9 | ESI+: 539.4 |
| 29 | 9 | ESI+: 571.2 |
| 30 | 9 | ESI+: 571.2 |
| 31 | 9 | ESI+:537.2 |
| 32 | 9 | ESI+:555.3 |

TABLE 8-2-continued

| Ex | Syn | DAT |
|---|---|---|
| 33 | 9 | ESI+: 573.4 |
|  |  | NMR DMSO-d6(500 MHz): 1.02-1.20 (1H, m), 1.71-1.88 (1H, m), 1.96-2.17 (3H, m), 2.36-2.65 (2H, m), 2.73 (1H, t), 2.93-3.08 (2H, m), 3.12-3.19 (1H, m), 6.95-7.45 (5H, m), 8.18-8.84 (3H, m), 9.43-10.61 (3H, m) |
| 34 | 9 | ESI+: 541.2 |
|  |  | NMR DMSO-d6(500 MHz): 1.96-2.17 (4H, m), 2.43-2.60 (2H, m), 3.04 (1H, s), 3.42-3.52 (2H, m), 7.00-7.04 (2H, m), 7.06 (1H, d), 7.12-7.19 (1H, m), 7.37-7.44 (2H, m), 8.18-8.24 (1H, m), 8.56-8.64 (1H, m), 8.79 (1H, s), 9.47-9.50 (1H, m), 9.81-9.84 (1H, m) |
| 35 | 9 | ESI+: 589.3, 591.4 |
| 36 | 9 | ESI+: 603.4, 605.3 |
| 37 | 9 | ESI+: 555.4 |
| 38 | 9 | ESI+: 580.2 |
| 39 | 9 | ESI+: 556.2 |
| 40 | 9 | ESI+: 589.2, 591.2 |
| 41 | 9 | ESI+: 573.3 |
| 42 | 9 | ESI+: 595.4 |
| 43 | 9 | ESI+: 587.3 |
| 44 | 9 | ESI+: 559.4 |
| 45 | 9 | ESI+: 555.4 |
| 46 | 9 | ESI+: 569.4 |
| 47 | 9 | ESI+: 532.4 |
| 48 | 9 | ESI+: 509.2 |

TABLE 8-3

| Ex | Syn | DAT |
|---|---|---|
| 49 | 49 | ESI+: 569.3 |
| 50 | 49 | ESI+: 569.3 |
| 51 | 49 | ESI+: 587.2 |
| 52 | 49 | ESI+: 601.2 |
| 53 | 49 | ESI+: 631.2 |
| 54 | 54 | ESI+: 583.4 |
| 55 | 54 | ESI+: 583.3 |
| 56 | 54 | ESI+: 585.4 |
| 57 | 54 | ESI+: 551.3 |
| 58 | 54 | ESI+: 599.4 |
| 59 | 59 | ESI+: 655.4 |
|  |  | NMR DMSO-d6(500 MHz): 1.69-1.92 (2H, m), 1.99-2.22 (1H, m), 2.30-2.41 (1H, m), 2.83-3.41 (13H, m), 3.55-3.99 (4H, m), 6.97-7.03 (2H, m), 7.06-7.12 (1H, m), 7.14-7.20 (1H, m), 7.38-7.46 (2H, m), 8.24 (1H, d), 8.29-8.34 (1H, m), 8.82-8.83 (1H, m), 9.47-9.52 (1H, m), 9.90-9.96 (1H, m), 10.03-10.13 (2H, m) |
| 60 | 59 | ESI+: 641.4 |
| 61 | 59 | ESI+: 653.4 |
| 62 | 62 | ESI+: 653.4 |
| 63 | 63 | ESI+: 615.2 |
| 64 | 64 | ESI+: 569.3 |

TABLE 8-4

| Ex | Syn | DAT |
|---|---|---|
| 65 | 6 | ESI+: 530.3 |
| 66 | 9 | ESI+: 603.3 |
| 67 | 9 | ESI+: 527.3 |
| 68 | 9 | ESI+: 517.3 |
| 69 | 9 | ESI+: 565.2 |
| 70 | 9 | ESI+: 567.0 |
| 71 | 9 | ESI+: 465.2 |
| 72 | 9 | ESI+: 501.3 |
| 73 | 9 | ESI+: 596.5 |
| 74 | 9 | ESI+: 582.4 |
| 75 | 9 | ESI+: 582.3 |
| 76 | 9 | ESI+: 546.4 |
| 77 | 9 | ESI+: 560.3 |
| 78 | 78 | ESI+: 582.3<br>NMR DMSO-d6(400 MHz): 1.25-1.34 (1H, m), 1.75-2.49 (6H, m), 2.87-3.58 (7H, m), 6.91-7.16 (4H, m), 7.36-7.41 (2H, m), 8.30-8.40 (1H, m), 8.51-8.74 (1H, m), 8.82 (1H, s), 9.41-9.50 (1H, m), 9.94-9.96 (1H, m), 10.13-10.40 (1H, m) |
| 79 | 78 | ESI+: 582.3 |
| 80 | 54 | ESI+: 610.4<br>NMR DMSO-d6(400 MHz): 1.56-1.77 (2H, m), 1.96-2.35 (8H, m), 2.50-2.67 (2H, m), 2.89-3.63 (6H, m), 6.94-7.18 (4H, m), 7.37-7.43 (2H, m), 8.29-8.40 (1H, m), 8.50-8.69 (1H, m), 8.83-8.84 (1H, m), 9.43-9.49 (1H, m), 9.95-9.96 (1H, m), 10.15-10.39 (1H, m) |
| 81 | 54 | ESI+: 610.3 |
| 82 | 54 | ESI+: 574.4 |
| 83 | 83 | ESI+: 587.3<br>NMR DMSO-d6(500 MHz): 1.11-1.26 (1H, m), 1.54-2.12 (3H, m), 2.25-2.45 (4H, m), 2.55-2.84 (3H, m), 2.93-3.30 (3H, m), 6.30 (2H, s), 6.95-7.46 (5H, m), 8.15-8.85 (3H, m), 9.48-10.54 (3H, m)<br>2θ(°) = 7.2, 8.8, 10.4, 10.7, 14.4, 15.1, 20.0, 21.7, 24.0, 26.7 |

TABLE 8-5

| Ex | Syn | DAT |
|---|---|---|
| 84 | 84 | ESI+: 555.4<br>NMR DMSO-d6(500 MHz): 1.09-1.27 (1H, m), 1.54-2.38 (4H, m), 2.61-2.86 (3H, m), 2.93-3.30 (3H, m), 6.34 (2H, s), 6.94-7.44 (6H, m), 8.18-8.85 (3H, m), 9.47-10.60 (3H, m)<br>2θ(°) = 5.4, 9.2, 10.4, 12.0, 14.1, 14.9, 16.4, 21.2, 23.7, 26.3 |
| 85 | 84 | ESI+: 573.3<br>NMR DMSO-d6(500 MHz): 1.13-1.28 (1H, m), 1.55-2.40 (4H, m), 2.61-2.88 (3H, m), 2.93-3.33 (3H, m), 6.33 (2H, s), 6.75-7.46 (5H, m), 8.17-8.89 (3H, m), 9.48-10.63 (3H, m)<br>2θ(°) = 9.3, 9.6, 10.4, 12.0, 13.9, 14.2, 15.2, 16.4, 22.4, 23.8 |
| 86 | 84 | ESI+: 573.3<br>NMR DMSO-d6(500 MHz): 1.09-1.29 (1H, m), 1.53-2.41 (4H, m), 2.61-2.86 (3H, m), 2.93-3.30 (3H, m), 6.33 (2H, s), 6.95-7.46 (5H, m), 8.16-8.87 (3H, m), 9.46-10.60 (3H, m)<br>2θ(°) = 9.3, 10.4, 12.1, 14.2, 14.9, 16.5, 18.0, 18.9, 23.9, 26.6 |
| 87 | 84 | ESI+: 541.3<br>NMR DMSO-d6(500 MHz): 1.92-2.30 (4H, m), 2.60-2.72 (2H, m), 3.05 (1H, br s), 3.47 (1H, br s), 3.62 (1H, br s), 6.41 (2H, s), 7.01-7.05 (2H, m), 7.06-7.14 (1H, m), 7.15-7.20 (1H, m), 7.39-7.45 (2H, m), 8.18-8.25 (1H, m), 8.67-8.80 (1H, m), 8.81 (1H, s), 9.45-9.54 (1H, m), 9.78-9.86 (1H, m)<br>2θ(°) = 6.2, 6.6, 11.0, 13.3, 15.9, 16.6, 17.9, 19.7, 20.3, 25.4 |

TABLE 9

| Reference Example | Str | DAT |
|---|---|---|
| 1 | 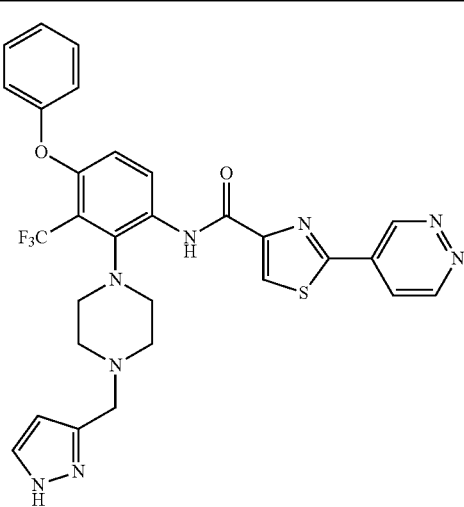 | ESI+: 607.4 |

INDUSTRIAL APPLICABILITY

The compound of the present invention or a salt thereof is useful as a DGK Δ inhibitor, and can be used as an active ingredient of a pharmaceutical composition, for example a pharmaceutical composition for treatment of cancer related to activation of immune cells or cancer having resistance to anti-PD-1 antibody/anti-PD-L1 antibody therapy.

The invention claimed is:

1. The compound of formula (I):

[Chemical Formula 1]

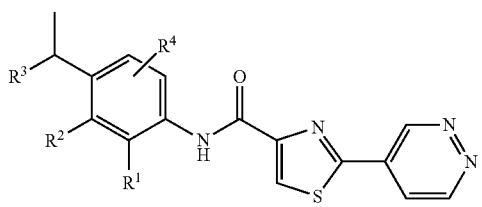

(I)

or a salt thereof, wherein $R^1$ is a group of formula (i), (ii), (iii) (iv) or (v):

[Chemical Formula 2]

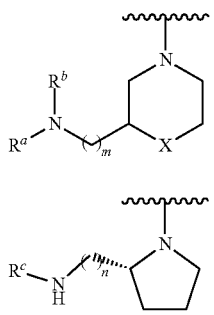

(i)

(ii)

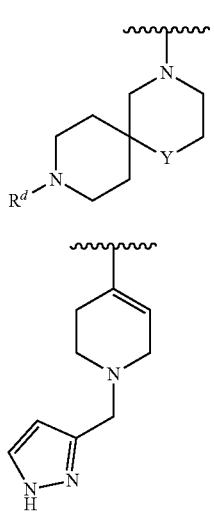

(iii)

(iv)

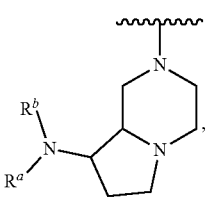

(v)

$R^2$ is a $C_{1-6}$ alkyl, a $C_{3-5}$ cycloalkyl, an —O—($C_{1-6}$ alkyl), methanesulphonyl, a halogeno-$C_{1-6}$ alkyl or a halogen, $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulphonyl and a halogen, ii) a $C_{3-8}$ cycloalkyl optionally substituted with a group selected from the group consisting of a $C_{1-6}$ alkyl and a halogen, iii) a pyridyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulphonyl and a halogen, iv) a pyrazolyl optionally substituted with a group selected from the group consisting of a $C_{1-6}$ alkyl and a halogen, or v) a pyrrolidinyl optionally substituted with a $C_{1-6}$ alkyl, $R^4$ is H or F, L is a bond, CO, $SO_2$, O or NH, X is $CH_2$, O or N-methyl, Y is $CH_2$ or O, $R^a$ is H or methyl, $R^b$ is H, methyl, ethyl or —$(CH_2)_2$O—$CH_3$, $R^c$ is H, methyl or oxetanyl, $R^d$ is H, methyl, —$(CH_2)_2$OH, —$(CH_2)_2$O—$CH_3$ or oxetanyl, m is 1 or 2, and n is 1 or 2.

2. The compound or a salt thereof according to claim 1, wherein $R^2$ is a halogeno-$C_{1-6}$ alkyl or a halogen, L is a bond, O or NH, X is $CH_2$ or N-methyl, $R^c$ is H or methyl, m is 1.

3. The compound or a salt thereof according to claim 2, wherein $R^1$ is a group of formula (i-a), (ii-a), (iii-a) or (v):

[Chemical Formula 3]

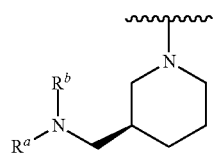

(i-a)

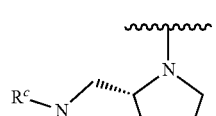

(ii-a)

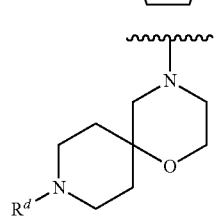

(iii-a)

-continued (v)

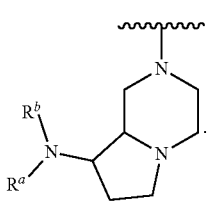

4. The compound or a salt thereof according to claim 3, wherein R³ is a phenyl optionally substituted with a group selected from the group consisting of a C₁₋₆ alkyl and a halogen; or a C₃₋₅ cycloalkyl.

5. The compound or a salt thereof according to claim 4, wherein R² is CF₃, R⁴ is H, R^b is H or methyl, and R^c is H.

6. The compound or a salt thereof according to claim 1, wherein the compound is selected from the group consisting of:
- N-{2-[(3S)-3-(aminomethyl) piperidin-1-yl]-4-phenoxy-3-(trifluoromethyl) phenyl}-2-(pyridazin-4-yl)-1,3-thiazole-4-carboxamide;
- N-{2-[(3S)-3-(aminomethyl) piperidin-1-yl]-4-(3-fluorophenoxy)-3-(trifluoromethyl) phenyl}-2-(pyridazin-4-yl)-1,3-thiazole-4-carboxamide;
- N-{2-[9-(2-methoxyethyl)-1-oxa-4,9-diazaspiro[5.5]undecan-4-yl]-4-phenoxy-3-(trifluoromethyl) phenyl}-2-(pyridazin-4-yl)-1,3-thiazole-4-carboxamide;
- N-{2-[(3S)-3-(aminomethyl) piperidin-1-yl]-4-(2-fluorophenoxy)-3-(trifluoromethyl) phenyl}-2-(pyridazin-4-yl)-1,3-thiazole-4-carboxamide;
- N-[4-(2-fluorophenoxy)-2-{(3S)-3-[(methylamino) methyl]piperidin-1-yl}-3-(trifluoromethyl) phenyl]-2-(pyridazin-4-yl)-1,3-thiazole-4-carboxamide;
- N-{2-[(2R)-2-(aminomethyl) pyrrolidin-1-yl]-4-phenoxy-3-(trifluoromethyl) phenyl}-2-(pyridazin-4-yl)-1,3-thiazole-4-carboxamide;
- N-{2-[(8R,8aS)-8-aminohexahydropyrrolo[1,2-a]pyrazine-2 (1H)-yl]-4-phenoxy-3-(trifluoromethyl) phenyl}-2-(pyridazin-4-yl)-1,3-thiazole-4-carboxamide; and
- N-{2-[(8R,8aS)-8-(dimethylamino) hexahydropyrrolo[1,2-a]pyrazine-2 (1H)-yl]-4-phenoxy-3-(trifluoromethyl) phenyl}-2-(pyridazin-4-yl)-1,3-thiazole-4-carboxamide.

7. The compound or a salt thereof according to claim 1, wherein the compound or a salt thereof is selected from the group consisting of:
- N-{2-[(3S)-3-(aminomethyl) piperidin-1-yl]-4-phenoxy-3-(trifluoromethyl) phenyl}-2-(pyridazin-4-yl)-1,3-thiazole-4-carboxamide mono[(2E)-but-2-enedioate];
- N-{2-[(3S)-3-(aminomethyl) piperidin-1-yl]-4-(3-fluorophenoxy)-3-(trifluoromethyl) phenyl}-2-(pyridazin-4-yl)-1,3-thiazole-4-carboxamide mono[(2E)-but-2-enedioate];
- N-{2-[(3S)-3-(aminomethyl) piperidin-1-yl]-4-(2-fluorophenoxy)-3-(trifluoromethyl) phenyl}-2-(pyridazin-4-yl)-1,3-thiazole-4-carboxamide mono[(2E)-but-2-enedioate];
- N-[4-(2-fluorophenoxy)-2-{(3S)-3-[(methylamino) methyl]piperidin-1-yl}-3-(trifluoromethyl) phenyl]-2-(pyridazin-4-yl)-1,3-thiazole-4-carboxamide mono[(2E)-but-2-enedioate]; and
- N-{2-[(2R)-2-(aminomethyl) pyrrolidin-1-yl]-4-phenoxy-3-(trifluoromethyl) phenyl}-2-(pyridazin-4-yl)-1,3-thiazole-4-carboxamide mono[(2E)-but-2-enedioate].

8. A pharmaceutical composition comprising the compound or a salt thereof according to claim 1.

9. The pharmaceutical composition according to claim 8, which is for treatment of cancer related to activation of immune cells or cancer having resistance to anti-PD-1 antibody/anti-PD-L1 antibody therapy.

10. The compound or a salt thereof of claim 1, wherein said compound has Diacylglycerol kinase ξ inhibitory activity.

11. A method for the treatment of cancer related to activation of immune cells or cancer having resistance to anti-PD-1 antibody/anti-PD-L1 antibody therapy, which comprises administering an effective amount of the compound or a salt thereof according to claim 1 to a subject, wherein the cancer is non-small cell lung cancer, mismatch repair-deficient bowel cancer, or melanoma.

12. The compound or a salt thereof according to claim 1, which is N-{2-[(3S)-3-(aminomethyl) piperidin-1-yl]-4-phenoxy-3-(trifluoromethyl) phenyl}-2-(pyridazin-4-yl)-1,3-thiazole-4-carboxamide.

13. The compound or a salt thereof according to claim 1, which is N-{2-[(3S)-3-(aminomethyl) piperidin-1-yl]-4-phenoxy-3-(trifluoromethyl) phenyl}-2-(pyridazin-4-yl)-1,3-thiazole-4-carboxamide mono[(2E)-but-2-enedioate].

14. The compound or a salt thereof according to claim 1, which is N-{2-[(3S)-3-(aminomethyl) piperidin-1-yl]-4-(3-fluorophenoxy)-3-(trifluoromethyl) phenyl}-2-(pyridazin-4-yl)-1,3-thiazole-4-carboxamide.

15. The compound or a salt thereof according to claim 1, which is N-{2-[(3S)-3-(aminomethyl) piperidin-1-yl]-4-(3-fluorophenoxy)-3-(trifluoromethyl) phenyl}-2-(pyridazin-4-yl)-1,3-thiazole-4-carboxamide mono[(2E)-but-2-enedioate].

16. The compound or a salt thereof according to claim 1, which is N-{2-[(3S)-3-(aminomethyl) piperidin-1-yl]-4-(2-fluorophenoxy)-3-(trifluoromethyl) phenyl}-2-(pyridazin-4-yl)-1,3-thiazole-4-carboxamide.

17. The compound or a salt thereof according to claim 1, which is N-{2-[(3S)-3-(aminomethyl) piperidin-1-yl]-4-(2-fluorophenoxy)-3-(trifluoromethyl) phenyl}-2-(pyridazin-4-yl)-1,3-thiazole-4-carboxamide mono[(2E)-but-2-enedioate].

18. The compound or a salt thereof according to claim 1, which is N-[4-(2-fluorophenoxy)-2-{(3S)-3-[(methylamino) methyl]piperidin-1-yl}-3-(trifluoromethyl) phenyl]-2-(pyridazin-4-yl)-1,3-thiazole-4-carboxamide.

19. The compound or a salt thereof according to claim 1, which is N-[4-(2-fluorophenoxy)-2-{(3S)-3-[(methylamino) methyl]piperidin-1-yl}-3-(trifluoromethyl) phenyl]-2-(pyridazin-4-yl)-1,3-thiazole-4-carboxamide mono[(2E)-but-2-enedioate].

20. The compound or a salt thereof according to claim 1, which is N-{2-[(2R)-2-(aminomethyl) pyrrolidin-1-yl]-4-phenoxy-3-(trifluoromethyl) phenyl}-2-(pyridazin-4-yl)-1,3-thiazole-4-carboxamide.

21. The compound or a salt thereof according to claim 1, which is N-{2-[(2R)-2-(aminomethyl) pyrrolidin-1-yl]-4-phenoxy-3-(trifluoromethyl) phenyl}-2-(pyridazin-4-yl)-1,3-thiazole-4-carboxamide mono[(2E)-but-2-enedioate].

22. A method for the treatment of cancer related to activation of immune cells or cancer having resistance to anti-PD-1 antibody/anti-PD-L1 antibody therapy, which comprises administering an effective amount of the compound or a salt thereof according to claim 1 to a subject, wherein the cancer is non-small cell lung cancer.

23. A method for the treatment of cancer related to activation of immune cells or cancer having resistance to anti-PD-1 antibody/anti-PD-L1 antibody therapy, which comprises administering an effective amount of the compound or a salt thereof according to claim 1 to a subject, wherein the cancer is mismatch repair-deficient bowel cancer.

24. A method for the treatment of cancer related to activation of immune cells or cancer having resistance to anti-PD-1 antibody/anti-PD-L1 antibody therapy, which comprises administering an effective amount of the compound or a salt thereof according to claim 1 to a subject, wherein the cancer is melanoma.

\* \* \* \* \*

UNITED STATES PATENT AND TRADEMARK OFFICE
CERTIFICATE OF CORRECTION

PATENT NO. : 12,227,517 B2
APPLICATION NO. : 17/427426
DATED : February 18, 2025
INVENTOR(S) : Hideyuki Watanabe et al.

Page 1 of 1

It is certified that error appears in the above-identified patent and that said Letters Patent is hereby corrected as shown below:

In the Claims

In Claim 1, Column 153, Line numbers 20-25, should read:

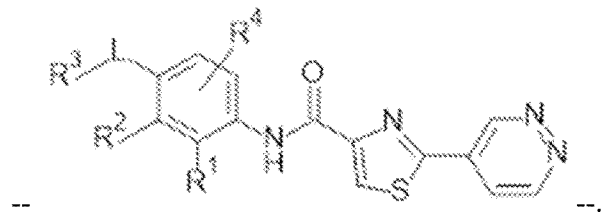

Signed and Sealed this
Twenty-sixth Day of August, 2025

Coke Morgan Stewart
*Acting Director of the United States Patent and Trademark Office*